US012168017B2

(12) United States Patent
Ostrow et al.

(10) Patent No.: US 12,168,017 B2
(45) Date of Patent: *Dec. 17, 2024

(54) D₂O STABILIZED PHARMACEUTICAL FORMULATIONS

(71) Applicant: Sydnexis, Inc., Del Mar, CO (US)

(72) Inventors: Gregory I. Ostrow, San Diego, CA (US); Kenneth J. Widder, Rancho Santa Fe, CA (US); David S. Baker, Carlsbad, CA (US)

(73) Assignee: SYDNEXIS, INC., Del Mar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/335,490

(22) Filed: Jun. 1, 2021

(65) Prior Publication Data

US 2021/0283142 A1 Sep. 16, 2021

Related U.S. Application Data

(63) Continuation of application No. 16/805,612, filed on Feb. 28, 2020, now Pat. No. 11,052,095, which is a continuation of application No. 15/578,202, filed as application No. PCT/US2016/034823 on May 27, 2016, now Pat. No. 11,052,094.

(60) Provisional application No. 62/168,538, filed on May 29, 2015.

(51) Int. Cl.
| | |
|---|---|
| *A61K 31/5575* | (2006.01) |
| *A61K 9/00* | (2006.01) |
| *A61K 9/06* | (2006.01) |
| *A61K 9/08* | (2006.01) |
| *A61K 31/18* | (2006.01) |
| *A61K 31/216* | (2006.01) |
| *A61K 31/565* | (2006.01) |
| *A61K 31/57* | (2006.01) |
| *A61K 47/02* | (2006.01) |
| *A61K 47/34* | (2017.01) |
| *A61K 47/38* | (2006.01) |
| *A61P 27/02* | (2006.01) |

(52) U.S. Cl.
CPC ........ *A61K 31/5575* (2013.01); *A61K 9/0048* (2013.01); *A61K 9/06* (2013.01); *A61K 9/08* (2013.01); *A61K 31/18* (2013.01); *A61K 31/216* (2013.01); *A61K 31/565* (2013.01); *A61K 31/57* (2013.01); *A61K 47/02* (2013.01); *A61K 47/34* (2013.01); *A61K 47/38* (2013.01); *A61P 27/02* (2018.01)

(58) Field of Classification Search
CPC .......................... A61K 31/5575; A61K 9/0048
See application file for complete search history.

(56) References Cited

U.S. PATENT DOCUMENTS

| | | |
|---|---|---|
| 3,863,633 A | 2/1975 | Ryde et al. |
| 4,014,335 A | 3/1977 | Arnold |
| 4,255,415 A | 3/1981 | Chrai et al. |
| 4,382,124 A | 5/1983 | Meitzner et al. |
| 4,474,751 A | 10/1984 | Haslam et al. |
| 4,852,582 A | 8/1989 | Pell |
| 4,938,763 A | 7/1990 | Dunn et al. |
| 4,952,586 A | 8/1990 | Morris et al. |
| 4,968,302 A | 11/1990 | Schluter et al. |
| 5,033,252 A | 7/1991 | Carter |
| 5,052,558 A | 10/1991 | Carter |
| 5,147,647 A | 9/1992 | Darougar |
| 5,249,712 A | 10/1993 | Lontrade et al. |
| 5,259,998 A | 11/1993 | Reich et al. |
| 5,260,000 A | 11/1993 | Nandu et al. |
| 5,323,907 A | 6/1994 | Kalvelage |
| 5,324,519 A | 6/1994 | Dunn et al. |
| 5,490,938 A | 2/1996 | Sawan et al. |
| 5,492,689 A | 2/1996 | Gwaltney, Jr. |
| 5,496,471 A | 3/1996 | Heyl et al. |
| 5,702,716 A | 12/1997 | Dunn et al. |
| 5,710,182 A | 1/1998 | Reunamaki et al. |
| 5,716,952 A | 2/1998 | Woldemussie et al. |
| 5,744,153 A | 4/1998 | Yewey et al. |
| 5,840,770 A | 11/1998 | Hill |
| 5,858,375 A | 1/1999 | Furminger et al. |
| 5,900,360 A | 5/1999 | Welch et al. |
| 5,976,499 A | 11/1999 | Rubenstein et al. |
| 5,990,194 A | 11/1999 | Dunn et al. |

(Continued)

FOREIGN PATENT DOCUMENTS

| | | |
|---|---|---|
| CN | 1323595 A | 11/2001 |
| CN | 1456161 A | 11/2003 |

(Continued)

OTHER PUBLICATIONS

Abak. Pure technology in a bottle. The history of a technological revolution. Laboratoires Thea—12 Rue Louis Bleriot—63017 Clermont Ferrand—France Tel. Retrieved from the Internet: https://www.laboratoires-thea.com/medias/abak_brochure_eng.pdf (pp. 1-53) (Apr. 18, 2011).

Abraham et al. Draize rabbit eye test compatibility with eye irritation thresholds in humans: a quantitative structure-activity relationship analysis. Toxicol Sci 76:384-391 (2003).

Anschel et al., Parenteral Formulation VI: Hydrolytic Degradation of Esters in Parenteral Solutions. Bulletin Of The Parenteral Drug Ass'n 26(6):271-289 (1972).

Atropine Sulfate Ophthalmic Solution, Highlights of Prescribing Information, Revised Jul. 2014.

(Continued)

*Primary Examiner* — Genevieve S Alley
(74) *Attorney, Agent, or Firm* — WILSON SONSINI GOODRICH & ROSATI

(57) ABSTRACT

Provided herein is an ophthalmic composition formulated in deuterated water. Also disclosed herein are methods of treating, ameliorating, or reducing ophthalmic conditions or diseases by administering to an eye of an individual in need thereof an effective amount of an ophthalmic composition as described herein.

20 Claims, 1 Drawing Sheet

(56) References Cited

U.S. PATENT DOCUMENTS

| | | |
|---|---|---|
| 6,139,870 A | 10/2000 | Verrecchia |
| 6,218,428 B1 | 4/2001 | Chynn et al. |
| 6,270,954 B1 | 8/2001 | Welch et al. |
| 6,410,048 B1 | 6/2002 | Fotinos |
| 6,503,497 B2 | 1/2003 | Chowhan et al. |
| 6,720,001 B2 | 4/2004 | Chen et al. |
| 7,691,099 B2 | 4/2010 | Berry |
| 7,858,582 B2 | 12/2010 | Jin et al. |
| 8,333,985 B2 | 12/2012 | Knaack et al. |
| 8,404,271 B2 | 3/2013 | Byrne et al. |
| 8,414,912 B2 | 4/2013 | Ciolino et al. |
| 8,623,400 B2 | 1/2014 | Liu et al. |
| 8,863,998 B2 | 10/2014 | Painchaud et al. |
| 8,980,839 B2 | 3/2015 | Mitra et al. |
| 8,986,266 B2 | 3/2015 | Painchaud et al. |
| 9,087,145 B2 | 7/2015 | Ballou, Jr. et al. |
| 9,238,003 B2 | 1/2016 | Byrne et al. |
| 9,421,199 B2 | 8/2016 | Ostrow et al. |
| 9,463,486 B2 | 10/2016 | Wilkerson et al. |
| 9,498,035 B2 | 11/2016 | Luk et al. |
| 9,539,604 B2 | 1/2017 | Wilkerson et al. |
| 9,770,447 B2 | 9/2017 | Ostrow et al. |
| 9,827,250 B2 | 11/2017 | Chehab et al. |
| 10,076,515 B2 | 9/2018 | Ostrow et al. |
| 10,201,534 B2 | 2/2019 | Ostrow et al. |
| 10,251,875 B2 | 4/2019 | Puri et al. |
| 10,813,923 B1 | 10/2020 | Ostrow et al. |
| 10,842,787 B2 | 11/2020 | Ostrow et al. |
| 10,864,208 B2 | 12/2020 | Ostrow et al. |
| 10,888,557 B2 | 1/2021 | Ostrow et al. |
| 10,940,145 B2 | 3/2021 | Ostrow et al. |
| 10,953,002 B2 | 3/2021 | Ostrow et al. |
| 11,052,094 B2 | 7/2021 | Ostrow et al. |
| 11,052,095 B2 | 7/2021 | Ostrow et al. |
| 11,896,588 B2 | 2/2024 | Ostrow et al. |
| 12,070,466 B2 | 8/2024 | Ostrow et al. |
| 2002/0151598 A1 | 10/2002 | Banerjee et al. |
| 2002/0190079 A1 | 12/2002 | Hamamoto |
| 2002/0193853 A1 | 12/2002 | Worthen et al. |
| 2003/0157187 A1 | 8/2003 | Hunter |
| 2003/0195179 A1 | 10/2003 | Sawa |
| 2004/0136915 A1 | 7/2004 | Dugger, III et al. |
| 2005/0249770 A1 | 11/2005 | Hunter |
| 2005/0251254 A1 | 11/2005 | Brady et al. |
| 2006/0159771 A1 | 7/2006 | Kadrmas et al. |
| 2007/0207192 A1 | 9/2007 | Holl et al. |
| 2007/0254914 A1 | 11/2007 | Wu et al. |
| 2007/0280992 A1 | 12/2007 | Margaron et al. |
| 2008/0021106 A1 | 1/2008 | Petit, II et al. |
| 2008/0027418 A1 | 1/2008 | Berry |
| 2008/0113035 A1 | 5/2008 | Hunter |
| 2008/0153900 A1 | 6/2008 | Hunter |
| 2008/0300316 A1 | 12/2008 | Gant et al. |
| 2009/0137956 A1 | 5/2009 | Souter |
| 2010/0022495 A1 | 1/2010 | Hotamisligil et al. |
| 2010/0196285 A1 | 8/2010 | Bayerl |
| 2010/0256557 A1 | 10/2010 | Lust et al. |
| 2011/0028477 A1 | 2/2011 | Aleo et al. |
| 2011/0076331 A1 | 3/2011 | Bayerl |
| 2012/0001503 A1 | 1/2012 | Owng et al. |
| 2012/0015035 A1 | 1/2012 | Wildsoet et al. |
| 2012/0028910 A1 | 2/2012 | Combal et al. |
| 2012/0064123 A1 | 3/2012 | Sawaya |
| 2012/0135084 A1 | 5/2012 | Bayerl |
| 2012/0143152 A1 | 6/2012 | Hunter et al. |
| 2012/0203161 A1 | 8/2012 | Herekar |
| 2012/0225952 A1 | 9/2012 | Warner et al. |
| 2012/0277694 A1 | 11/2012 | Odrich et al. |
| 2013/0302855 A1 | 11/2013 | Selber et al. |
| 2013/0303502 A1 | 11/2013 | Cavanagh et al. |
| 2014/0011761 A1 | 1/2014 | Hotamisligil et al. |
| 2014/0088199 A1 | 3/2014 | Sharma |
| 2014/0249140 A1 | 9/2014 | Niquet et al. |
| 2014/0336618 A1 | 11/2014 | Wilkerson et al. |
| 2014/0343030 A1 | 11/2014 | Li et al. |
| 2014/0350049 A1 | 11/2014 | Hovnanian et al. |
| 2015/0038473 A1 | 2/2015 | Stein et al. |
| 2015/0065511 A1 | 3/2015 | Horn et al. |
| 2015/0076174 A1 | 3/2015 | Mersmann |
| 2015/0290125 A1 | 10/2015 | Horn et al. |
| 2015/0297800 A1 | 10/2015 | Weikart et al. |
| 2015/0366854 A1 | 12/2015 | Ostrow et al. |
| 2016/0009705 A1 | 1/2016 | Ostrow et al. |
| 2016/0018671 A1 | 1/2016 | Waite et al. |
| 2016/0279663 A1 | 9/2016 | Mersmann |
| 2016/0339007 A1 | 11/2016 | Ostrow et al. |
| 2017/0224531 A1 | 8/2017 | Chauhan et al. |
| 2017/0304152 A1 | 10/2017 | Hernandez |
| 2018/0000950 A1 | 1/2018 | Savel et al. |
| 2018/0193326 A1 | 7/2018 | Ostrow et al. |
| 2018/0325888 A1 | 11/2018 | Puri et al. |
| 2019/0255018 A1 | 8/2019 | Corr et al. |
| 2020/0085813 A1 | 3/2020 | Ostrow et al. |
| 2020/0163951 A1 | 5/2020 | Ouyang et al. |
| 2020/0222369 A1 | 7/2020 | Feinbaum et al. |
| 2020/0306239 A1 | 10/2020 | Ostrow et al. |
| 2020/0338060 A1 | 10/2020 | Ostrow et al. |
| 2020/0345542 A1 | 11/2020 | Ostrow et al. |
| 2021/0059998 A1 | 3/2021 | Ostrow et al. |
| 2021/0393649 A1 | 12/2021 | Ostrow et al. |
| 2022/0265631 A1 | 8/2022 | Ostrow et al. |
| 2022/0265632 A1 | 8/2022 | Ostrow et al. |
| 2022/0378775 A1 | 12/2022 | Ostrow et al. |
| 2022/0409603 A1 | 12/2022 | Ostrow et al. |
| 2022/0409604 A1 | 12/2022 | Ostrow et al. |
| 2022/0409605 A1 | 12/2022 | Ostrow et al. |
| 2023/0041788 A1 | 2/2023 | Ostrow et al. |
| 2023/0091109 A1 | 3/2023 | Ostrow et al. |
| 2023/0092957 A1 | 3/2023 | Ostrow et al. |
| 2023/0093205 A1 | 3/2023 | Ostrow et al. |
| 2023/0381016 A1 | 11/2023 | Ostrow et al. |
| 2024/0139166 A1 | 5/2024 | Ostrow et al. |
| 2024/0165098 A1 | 5/2024 | Ostrow et al. |

FOREIGN PATENT DOCUMENTS

| | | |
|---|---|---|
| CN | 101049287 A | 10/2007 |
| CN | 101327216 A | 12/2008 |
| CN | 101468214 A | 7/2009 |
| DE | 1182388 B | 11/1964 |
| DE | 1518819 B1 | 12/1969 |
| EP | 0332826 A1 | 9/1989 |
| EP | 1998783 B1 | 5/2014 |
| GB | 2293100 A | 3/1996 |
| JP | H01203320 A | 8/1989 |
| JP | 2007308398 A | 11/2007 |
| JP | 2014032404 A | 2/2014 |
| WO | WO-9421298 A1 | 9/1994 |
| WO | WO-9624331 A1 | 8/1996 |
| WO | WO-9716192 A1 | 5/1997 |
| WO | WO-0049990 A2 | 8/2000 |
| WO | WO-02096418 A1 | 12/2002 |
| WO | WO-2008005053 A1 | 1/2008 |
| WO | WO-2008008330 A2 | 1/2008 |
| WO | WO-2010083129 A2 | 7/2010 |
| WO | WO-2011019940 A2 | 2/2011 |
| WO | WO-2011098578 A2 | 8/2011 |
| WO | WO-2011137449 A1 | 11/2011 |
| WO | WO-2012111029 A2 | 8/2012 |
| WO | WO-2012161655 A1 | 11/2012 |
| WO | WO-2013166385 A1 | 11/2013 |
| WO | WO-2013167865 A1 | 11/2013 |
| WO | WO-2014140105 A1 | 9/2014 |
| WO | WO-2014182620 A1 | 11/2014 |
| WO | WO-2015200361 A1 | 12/2015 |
| WO | WO-2016025560 A1 | 2/2016 |
| WO | WO-2016172712 A2 | 10/2016 |
| WO | WO-2016196367 A1 | 12/2016 |
| WO | WO-2017204262 A1 | 11/2017 |
| WO | WO-2018154440 A1 | 8/2018 |
| WO | WO-2018209051 A1 | 11/2018 |
| WO | WO-2019104191 A1 | 5/2019 |

(56) References Cited

FOREIGN PATENT DOCUMENTS

| WO | WO-2020087021 A1 | 4/2020 |
|---|---|---|
| WO | WO-2021126874 A1 | 6/2021 |
| WO | WO-2022169959 A1 | 8/2022 |

OTHER PUBLICATIONS

Atropine Sulfate Ophthalmic Solution, Highlights of Prescribing Information, Revised Jul. 2014, Wayback Machine and Affidavit.
Badaro et al. Retinal biocompatibility of brilliant Blue G with deuterated water for chromovitrectomy. J. Ophthalmic and Vision Research 9(2): 204-209 (2014).
Bender et al., Deuterium Oxide Solvent Isotope Effects in the Nucleophilic Reactions of Phenyl Esters. J. Am. Chem. Soc. 84(4):595-599 (1962).
Berton et al., Stability of Ophthalmic Atropine Solutions for Child Myopia Control. Pharmaceutics 12(8):781 (2020).
Blake et al., Studies with Deuterated Drugs. J. Pharm. Sci. 64(3):367-391 (1975).
Brown et al. The Preservation of Ophthalmic Preparations. J. Soc. Cosmetic Chemists 16:369-393 (1965).
Certified English Translation of CN 101049287A.
Chasin et al. Polyanhdrides for Controlled Drug Delivery. Biopharm pp. 33-46 (1988).
Cheng et al. Water movement in the rabbit eye. Exp. Eye Res. 52:337-339 (1991).
Cheng. Fate of water in the soft contact lens immediately after lens placement onto the cornea. Optometry and Vision Science 68(6):414-417 (1991).
Chia et al., Atropine for the Treatment of Childhood Myopia: Changes after Stopping Atropine 0.01%, 0.1% and 0.5%. Am. J. Ophthalmology 157(2):451-457.e1 (2014).
Chia et al., Atropine for the Treatment of Childhood Myopia: Safety and Efficacy of 0.5%, 0.1%, and 0.01% Doses (Atropine for the Treatment of Myopia 2). Ophthalmology 119(2):347-354 (2012).
Chirieri et al. Investigations concerning the changes induced by deuterium for hydrogen substitution in bioelectric activity of the frog retina. Physiologie 14(2):119-123 (1977).
Chua et al., Atropine for the Treatment of Childhood Myopia. Ophthalmology 113(12):2285-2291 (2006).
Criado et al. Scavenging of photogenerated oxidative species by antimuscarinic drugs: atropine and derivatives. Redoc Rep 7(6):385-394 (2002).
Declaration of Dr. Stephen Byrn, Ph. D., dated Feb. 2, 2021.
Dictionary Of Chemistry (McGraw Hill 2nd ed.) (443 pgs) (2003).
Donnelly et al. Physical Compatibility and Chemical Stability of a Concentrated Solution of Atropine Sulfate (2 mg/mL) for Use as an Antidote in Nerve Agent Casualties. Int'l J. Pharm. Compounding 12(6):550-552 (2008).
Douglas et al. Nanoparticles in Drug Delivery. CRC Crit. Rev. Therap. Drug Carr Syst 3:233-261 (1987).
Driver et al., The Stability of Atropine Sulfate Solutions Stored in Plastic Syringes in the Operating Room. Anesth. Analg. 89:1056-1058 (1999).
Drug Repositioning Bringing New Life To Shelved Assets And Existing Drugs pp. 53-64, 291-343 (Michael J. Barratt & Donald E. Frail eds., 2012).
Fang et al. Prevention of Myopia Onset with 0.025% Atropine in Premyopic Children. Journal of Ocular Pharmacology and Therapeutics 26(4):341-345 (2010).
Filed Application of U.S. Pat. No. 9,421,199, May 29, 2015.
Florence. Chapter 3: Physicochemical properties of drugs in solution. Physiochemical Principles Of Pharmacy pp. 56-92 (4th ed. 2006).
Food Drug Administration Center for Drugs Evaluation Research Guidance For Industry: Drug Stability Guidelines (Dec. 9, 2008).
Foster et al. Deuterium isotope effects in the metabolism of drugs and xenobiotics: implications for drug design. Adv Drug Res 14:1-36 (1985).
Ganea. Heavy water effect on certain energetic processes in retina. Physiologie 6(1):59-62 (1979).
Gant. Using Deuterium in Drug Discovery: Leaving the Label in the Drug. J. Med. Chem. 57(9):3595-3611 (2014).
Garcia-Valldecabres et al. pH Stability of ophthalmic solutions. Optometry 75(3):161-168 (2004).
Garcia-Valldecabres et al. pH Stability of ophthalmic solutions. Optometry 75(3):161-168 (2004) (Abstract only).
Gettings et al. A comparison of low volume, Draize and in vitro eye irritation test data. III. Surfactant-based formulations. Food Chem Toxicol 36(3):209-231 (1998).
Glasoe et al. Use of glass electrodes to measure acidities in deuterium oxide. Journal of Physical Chemistry.64:188-190 (1960).
Guidance for Industry: Q1A (R2) Stability Testing of New Drug Substances and Products. U.S. Department of Health and Human Services, Food and Drug Administration. Retrieved from the internet http://fda.gov/downloads/drugs/guidancecomplianceregulatoryinformation/guideances/ucm073369.pdf (25 pgs.) (Nov. 2013/retrieved Jul. 27, 2016).
Hanson et al., A Mechanistic and Kinetic Study of the E-Ring Hydrolysis and Lactonization of a Novel Phosphoryloxymethyl Prodrug of Camptothecin. Pharm. Research 20(7):1031-1038 (2003).
Hui et al. In vitro release of two anti-muscarinic drugs from soft contact lenses. Clin Ophthalmol 11:1657-1665 (2017).
Januschowski et al. Evaluating retinal toxicity of a new heavy intraocular dye, using a model of perfused and isolated retinal cultures of bovine and human origins. Graefes Arch Clin Exp Ophthalmol. 250:1013-1022 (2012).
Jencks et al. General Base Catalysis of Ester Hydrolysis. J. Am. Chem. Soc. 83(7):1743-50 (1961).
Jeong et al. Biodegradable block copolymers as injectable drug-delivery systems. Nature 388(6645):860-862 (1997).
Jeong et al. Drug release from biodegradable injectable thermosensitive hydrogel of PEG-PLGA-PEG triblock copolymers. J Control Release 63(1-2):155-163 (2000).
Jeong et al. Thermosensitive sol-gel reversible hydrogels. Advanced Drug Delivery Reviews 54:37-51 (2002).
Kirchhoff et al., Analysis of atropine, its degradation products and related substances of natural origin by means of reversed-phase high-performance liquid chromatography. J. Chromatography A 1046:115-120 (2004).
Kondritzer et al. Stability of Atropine in Aqueous Solution. J. Am. Pharm. Ass'n 46(9):531-535 (1957).
Kresge. Solvent Isotope Effect in H2O-D2O Mixtures. Pure Appl. Chem. 8(3-4):243-258 (1964).
Krezel et al. A formula for correlating pKa values determined in D2O and H2O. Journal of Inorganic Chemistry 98:161-166 (2008).
Krumbiegel. Large deuterium isotope effects and their use: a historical review. Isotopes in Environmental and Health Studies 47(1):1-17 (2011).
Kushner et al. Pharmacological uses and perspective of heavy water and deuterated compounds. Canadian Journal of Physiology and Pharmacology 77(2):79-88 (1999).
Lachkar et al. Drug-induced acute angle closure glaucoma. Curr Opin Ophthalmol. 18(2):129-33 (2007).
Lai et al. Rapid transport of large polymeric nanoparticles in fresh undiluted human mucus. PNAS USA 104(5):1482-1487 (2007).
Lallemand et al., Successfully Improving Ocular Drug Delivery Using the Cationic Nanoemulsion. Novasorb, J. Drug Delivery 2012:1-16 (2012).
Lee et al., Prevention of Myopia Progression with 0.05% Atropine Solution. J Ocul Pharmacol Ther. 22(1):41-46 (2006).
Li. Preparation and Quality Control of 0.04% Atropine Sulfate Eye Drops. China Pharmacy 17(2):111-113 (2006) (English Translation).
Lin et al., Formulation and stability of an extemporaneous 0.02% chlorhexidine digluconate ophthalmic solution. J. Formosan Med. Ass'n 114:1162-1169 (2015).
Lund et al. The Kinetics of atropine and apoatropine in aqueous solutions. ACTA Chemica Scandinavica 22:3085-3097 (1968).
McBrien et al., Point-Counterpoint. How does atropine exert its anti-myopia effects? Ophthalmic & Physiol Opt. 33:373-378 (2013).

(56) References Cited

OTHER PUBLICATIONS

McCall et al. Mechanisms of corneal tissue cross-linking in response to treatment with topical riboflavin and long-wavelength ultraviolet radiation (UVA). Investigative Ophthalmology & Visual Science 51(1):129-138 (2010).
Minor et al. One-Proton Solvation Bridge in Intramolecular Carboxylate Catalysis of Ester Hydrolysis. J. Am. Chem. Soc. 95(7):2279-2281 (1973).
NCT02130167. Low Concentration atropine for Myopia Progression in school Children. ClinicalTrials.gov archive (3 pgs) (Jan. 29, 2018).
Nee. The Use Of Deuterium Oxide To Stabilize Pharmaceuticals Against Chemical Degradation. SlideServe—Theophilus Stavros. Retrieved from the Internet: URL:https://www.slideserve.com/theophilus-stavros/the-use-of-deuterium-oxide-to-stabilize-pharmaceuticals-against-chemical-degradation (20 pgs) (Nov. 1, 2014).
Obata et al. Deuterium magnetic resonance imaging of rabbit eye in Vivo. Magnetic Resonance in Medicine.33(4):569-572 (1995).
Obata et al. Deuterium MR in vivo imaging of the rat eye using 2H2O. Acta Radiologica,36:552-555 (1995).
Obridge Koichi. Eyedrop New Insight, eyedrop—common send, common sense—General knowledge, Co. Ltd. Jul. 10, 1997 (pp. 9-14 and 166-121).
Patel et al., Ophthalmic Drug Delivery System: Challenges and Approaches. Systematic Reviews In Pharmacy 1(2):113-120 (2010).
PCT/US2015/037249 International Search Report and Written Opinion dated Sep. 30, 2015.
PCT/US2016/029222 International Search Report and Written Opinion dated Oct. 21, 2016.
PCT/US2016/034823 International Search Report and Written Opinion dated Aug. 23, 2016.
PCT/US2018/062279 International Search Report and Written Opinion dated Feb. 1, 2019.
Pfannkoch. Chapter 3: The Preparation of Buffers and Other Solutions: A Chemist's Perspective. Molecular Biology Problem Solver: A Laboratory Guide pp. 31-47 (Alan S. Gerstein ed., 2001).
U.S. Appl. No. 60/016,502, filed Jun. 24, 2014.
U.S. Appl. No. 62/096,433, filed Dec. 23, 2014.
Rajpal et al., Bromfenac ophthalmic solution for the treatment of postoperative ocular pain and inflammation: safety, efficacy, and patient adherence. Patient Prefer Adherence 8:925-31 (2014).
Richard et al. Effects of sterilizing-grade filters on the physicochemical properties of onion-like vesicles. Int J Pharm 312(1-2):144-150 (2006).
Sadeghi-Hashjin et al. Effects of Selected Antimuscarinic Agents on the Intra-Ocular Pressure in Healthy Rabbits. Journal of Pharmacology and Toxicology 3(5):382-385 (2008).
Schier et al., Preparing for Chemical Terrorism: Stability of Injectable Atropine Sulfate. Acad. Emerg. Med. 11(4):329-334 (2004).
Schowen. Chapter 6: Solvent Hydrogen Isotope Effects, Transition States Of Biochem Processes pp. 25-283 (Richard D. Gandour & Richard L. Schowen eds., 1978).
Sen et al., Role of heavy water in biological sciences with an emphasis on thermostabilization of vaccines. Expert Rev. Vaccines 8(11):1587-1602 (2009).
Shih et al., An intervention trial on efficacy of atropine and multi-focal glasses in controlling myopic progression. Acta Ophthalmologica Scandinavica 79:233-236 (2001).
Shih et al., Effects of Different Concentrations of Atropine on Controlling Myopia in Myopic Children. J Ocul Pharmacol Ther. 15(1):85-90 (1999).
Siegel et al. Stability of procaine in deuterium oxide. J Pharm Sci 53:978-979 (1964).
Sodium Phosphate Dibasic, Anhydrous Material Safety Data Sheet, Scholar Chem. (Jan. 23, 2009).
Sodium phosphate monobasic Safety Data Sheet, Version 1.1, G-BIOSCIS. (Jan. 9, 2012).
Stefanidis et al., General Base Catalysis of Ester Hydrolysis. J. Am. Chem. Soc. 115:6045-6050 (1993).
Susina et al., Effect of Deuterium Oxide on Local Anesthetic Activity of Procaine. J. Pharm. Sci. 51(12):1166-1169 (1962).
Taktak et al. Assay of Pyrogens by Interleukin-6 Release from Monocytic Cell Lines. J. Pharm. Pharmacol. 43:578-582 (1991).
The U. S. Food and Drug Administration has provided regulatory guidance in the publication: Guidance for Industry: Sterile Drug Products Produced by Aseptic Processing. available at: http://www.fda.gov/cder/guidance/5882fn1.htm (Aug. 2003) (63 pgs.).
Timmins. Deuterated drugs; where are we now? Expert Opin. Ther. Pat. 24(10):1067-1075 (2014).
U.S. Pat. No. 10,076,515 Non-Final Rejection Nov. 24, 2017.
U.S. Pat. No. 10,076,515 Notice of Allowance May 24, 2018.
U.S. Pat. No. 10,076,515 Petition for Inter Partes Review dated Mar. 3, 2021 (Case No. IPR2021-00441).
U.S. Pat. No. 10,076,515 Terminal Disclaimer.
U.S. Pat. No. 9,421,199, Interview Summary, Apr. 13, 2016.
U.S. Pat. No. 9,421,199, Non-Final Rejection, Mar. 7, 2016.
U.S. Pat. No. 9,421,199, Notice of Allowance, Jun. 13, 2016.
U.S. Pat. No. 9,421,199 Petition for Inter Partes Review dated Feb. 3, 2021 (Case No. IPR2021-00439).
U.S. Pat. No. 9,421,199, Response to Non-Final Rejection, Apr. 5, 2016.
U.S. Pat. No. 9,770,447, Advisory Action, Apr. 13, 2017.
U.S. Pat. No. 9,770,447, AFCP2.0 Response to Final Office Action Dated and Advisory Action, Apr. 21, 2017.
U.S. Pat. No. 9,770,447, Certificate of Correction.
U.S. Pat. No. 9,770,447, Final Rejection, Jan. 25, 2017.
U.S. Pat. No. 9,770,447, Information Disclosure Statement and International Search Report, Nov. 17, 2016.
U.S. Pat. No. 9,770,447, Non-Final Office Action, Sep. 30, 2016.
U.S. Pat. No. 9,770,447, Notice of Allowance, May 30, 2017.
U.S. Pat. No. 9,770,447 Petition for Inter Partes Review dated Feb. 17, 2021 (Case No. IPR2021-00440).
U.S. Pat. No. 9,770,447, Preliminary Amendment and Response to Notice to File Missing Parts, Aug. 3, 2013.
U.S. Pat. No. 9,770,447, Response to Final Office Action, Mar. 21, 2017.
U.S. Appl. No. 14/859,042 Office Action dated May 18, 2017.
U.S. Appl. No. 14/859,042 Office Action dated Oct. 25, 2016.
U.S. Appl. No. 15/208,537 Office Action dated Jan. 25, 2017.
U.S. Appl. No. 15/208,537 Office Action dated Sep. 30, 2016.
U.S. Appl. No. 15/568,381 Office Action dated Apr. 16, 2020.
U.S. Appl. No. 15/568,381 Office Action dated Apr. 3, 2019.
U.S. Appl. No. 15/568,381 Office Action dated Nov. 22, 2019.
U.S. Appl. No. 15/578,202 Office Action dated Jan. 3, 2020.
U.S. Appl. No. 15/578,202 Office Action dated Jan. 7, 2021.
U.S. Appl. No. 15/578,202 Office Action dated Jun. 1, 2020.
U.S. Appl. No. 15/578,202 Office Action dated Jun. 28, 2019.
U.S. Appl. No. 15/661,816 Office Action dated Nov. 24, 2017.
U.S. Appl. No. 15/895,933 Office Action dated Aug. 9, 2018.
U.S. Appl. No. 16/224,286 Ex Parte Quayle dated Jun. 24, 2020.
U.S. Appl. No. 16/224,286 Office Action dated Dec. 23, 2019.
U.S. Appl. No. 16/677,538 Office Action dated Jan. 13, 2020.
U.S. Appl. No. 16/785,411 Office Action dated Dec. 14, 2020.
U.S. Appl. No. 16/785,411 Office Action dated Jun. 23, 2020.
U.S. Appl. No. 16/785,411 Office Action dated Jun. 28, 2021.
U.S. Appl. No. 16/785,413 Office Action dated Aug. 3, 2020.
U.S. Appl. No. 16/785,416 Office Action dated Aug. 3, 2020.
U.S. Appl. No. 16/785,418 Office Action dated Aug. 3, 2020.
U.S. Appl. No. 16/805,612, Information Disclosure Statement, Mar. 2, 2020.
U.S. Appl. No. 16/805,612 Office Action dated May 15, 2020.
U.S. Appl. No. 16/805,612 Office Action dated Nov. 23, 2020.
U.S. Appl. No. 16/908,417 Office Action dated Aug. 3, 2020.
U.S. Appl. No. 16/908,426 Office Action dated Aug. 18, 2020.
U.S. Appl. No. 16/908,426 Office Action dated Oct. 20, 2020.
Viegas et al. Osmotic behavior of poloxamer 407 and other non-ionic surfactants in aqueous solutions. Int J Pharm 160:157-162 (1998).
Waterman et al., Hydrolysis in Pharmaceutical Formulations. Pharm. Dev. & Tech. 7(2):113-146 (2002).

(56) References Cited

OTHER PUBLICATIONS

Wen. Preparation and Clinical Curative Effects of 0.05% Atropine Sulfate Eye Drops. China Pharmacist 11(2):194-196 (2008) (Certified English Translation).
Winter et al. Studies in solvolysis. Part I. The neutral hydrolysis of some alkyl trifluoroacetates in water and deuterium oxide. Can J. Chem. 46:2887-2894 (1968).
Winter et al. Studies in Solvolysis. Part IV. Substituent and Solvent Isotope Effects in the Solvolysis of a Series of Benzyl Trifluroacetates. Can. J. Chem. 50:1886-90 (1972).
Wu et al., The Long-Term Results of Using Low-Concentration Atropine Eye Drops for Controlling Myopia Progression in Schoolchildren. J Ocul Pharmacol Ther. 27(5):461-466 (2011).
Yarnell. Heavy-Hydrogen Drugs Turn Heads, Again. Chemical & Eng'g News 87(25):36-39 (2009).
Zvirblis et al. Kinetics and Stability of a Multicomponent Organophosphate Antidote Formulation in Glass and Plastic, J. Pharm. Scis. 71(3):321-325 (1982).
Zvirblis et al., The Kinetics of the Hydrolysis of Atropine. J. Am. Pharm. Ass'n 45(7):450-454 (1956).
Akorn Atropine CareTM (Atropine Sulfate Ophthalmic Solution, 1%), Product Label Rev. 06/08.
Akorn Atropine CareTM (atropine sulfate ophthalmic solution), Advertisement Rev. 08/11.
Akorn Atropine CareTM (atropine sulfate ophthalmic solution), NDA 206289 Product Label (Revised Jul. 2014).
Application No. 206289Orig1s000 Summary Review, U.S. FDA Ctr. for Drug Evaluation & Res. (Jul. 18, 2014).
Co-pending U.S. Appl. No. 18/055,940, inventors Ostrow; Gregory I. et al., filed Nov. 16, 2022.
Co-pending U.S. Appl. No. 18/055,945, inventors Ostrow; Gregory I. et al., filed Nov. 16, 2022.
Co-pending U.S. Appl. No. 18/055,949, inventors Ostrow; Gregory I. et al., filed Nov. 16, 2022.
Declaration of Dr. Stephen Byrn, Ph. D., dated Jan. 7, 2022 (U.S. Appl. No. 10/888,557).
Declaration of Dr. Stephen Byrn, Ph. D., dated Jan. 7, 2022 (U.S. Appl. No. 10/940,145).
Declaration of Dr. Stephen Byrn, Ph.D., dated Dec. 29, 2021 (U.S. Appl. No. 10/842,787).
Drugs@FDA: FDA-Approved Drugs: Akorn NDA 206289, U.S. FDA, https://www.accessdata.fda.gov/scripts/cder/daf/index.cfm?event=overview.process&ApplNo=206289.
Fletcher et al. The effect of solution tonicity on the eye. Clin. & Exp. Optom. 76.1:17-21 (1993).
Ganesan et al. Pharmaceutical intervention for myopia control. Expert Rev Ophthalmol 5(6):759-787 (2010).
Howard. Chapter 17: Special Solutions and Suspensions. Ansel's Pharmaceutical Dosage Forms and Drug Delivery Systems. pg. 607 (Dec. 2013).
Mair et al. The Detection of Atropine and Its Degradation Products by Thin-Layer Chromatography. J. Clin. Pharm. 2:101-104 (1977).
Parmar et al. The solution, solid state stability and kinetic investigation in degradation studies of lercanidipine: study of excipients compatibility of lercanidipine. Pharm. Dev. Technol. 17(6):730-740 (2011).
PCT/US2020/065149 International Search Report and Written Opinion dated Mar. 22, 2021.
Rubinson. Practical corrections for p(H,D) measurements in mixed H2O/D2O biological buffers. Anal. Methods 9:2744-2750 (2017).
Schubert et al., Sterility of Anesthetic Multiple-Dose Vials after Opening. Anesthesiology 62:634-636 (1985).
Sharma et al. A quantitative NMR protocol for the simultaneous analysis of atropine and obidoxime in parenteral injection devices. J Pharm Biomed Anal 49(4):1092-1096 (2009).
Taylor et al. A critical appraisal of drug stability testing methods. Pharm. Res. 4(3):177-80 (1987).
Unknown. Modern Physical Organic Chemistry. Notes Chapter 8 (2) Under the isotope effect. Available at https://www.zhihu.com/tardis/sogou/art/163777237 (Edited 2020).
U.S. Pat. No. 10,076,515 Decision Denying Institution of Inter Partes Review dated Nov. 7, 2022 (Case No. IPR2022-00965).
U.S. Pat. No. 10,076,515 File History.
U.S. Pat. No. 10,076,515 Patent Owner's Preliminary Response dated Aug. 11, 2022 (Case No. IPR2022-00965).
U.S. Pat. No. 10,076,515 Petition for Inter Partes Review dated May 3, 2022 (Case No. IPR2022-00965).
U.S. Pat. No. 10,201,534 Decision Denying Institution of Inter Partes Review dated Nov. 7, 2022 (Case No. IPR2022-00966).
U.S. Pat. No. 10,201,534 File History.
U.S. Pat. No. 10,201,534 Patent Owner's Preliminary Response dated Aug. 11, 2022 (Case No. IPR2022-00966).
U.S. Pat. No. 10,201,534 Petition for Inter Partes Review dated May 3, 2022 (Case No. IPR2022-00966).
U.S. Pat. No. 10,251,875 File History.
U.S. Pat. No. 10,842,787 Decision dated Jul. 15, 2022 (Case No. IPR2022-00384).
U.S. Pat. No. 10,842,787 File History.
U.S. Pat. No. 10,842,787 Petition for Inter Partes Review dated Dec. 29, 2021 (Case No. IPR2022-00384).
U.S. Pat. No. 10,888,557 Decision dated Jul. 15, 2022 (Case No. IPR2022-00415).
U.S. Pat. No. 10,888,557 File History.
U.S. Pat. No. 10,888,557 Petition for Inter Partes Review dated Jan. 7, 2022 (Case No. IPR2022-00415).
U.S. Patent No. 10,940,145 Decision dated Jul. 15, 2022 (Case No. IPR2022-00414).
U.S. Patent No. 10,940,145 File History.
U.S. Patent No. 10,940,145 Petition for Inter Partes Review dated Jan. 7, 2022 (Case No. IPR2022-00414).
U.S. Patent No. 9,421,199 Decision Denying Institution of Inter Partes Review dated Nov. 8, 2022 (Case No. IPR2022-00963).
U.S. Pat. No. 9,421,199 File History.
U.S. Pat. No. 9,421,199 Patent Owner's Preliminary Response dated Aug. 11, 2022 (Case No. IPR2022-00963).
U.S. Patent No. 9,421,199 Petition for Inter Partes Review dated May 3, 2022 (Case No. IPR2022-00963).
U.S. Pat. No. 9,770,447 Decision Denying Institution of Inter Partes Review dated Nov. 7, 2022 (Case No. IPR2022-00964).
U.S. Pat. No. 9,770,447 File History.
U.S. Pat. No. 9,770,447 Patent Owner's Preliminary Response dated Aug. 11, 2022 (Case No. IPR2022-00964).
U.S. Pat. No. 9,770,447 Petition for Inter Partes Review dated May 3, 2022 (Case No. IPR2022-00964).
U.S. Appl. No. 16/765,144 Office Action dated Feb. 2, 2023.
U.S. Appl. No. 16/765,144 Office Action dated Mar. 29, 2022.
U.S. Appl. No. 16/765,144 Office Action dated Sep. 2, 2022.
U.S. Appl. No. 16/785,411 Office Action dated Jan. 24, 2022.
U.S. Appl. No. 16/785,411 Office Action dated Sep. 9, 2022.
U.S. Appl. No. 16/908,426 Office Action dated Jan. 24, 2022.
U.S. Appl. No. 16/908,426 Office Action dated Sep. 9, 2022.
U.S. Appl. No. 17/097,930 Office Action dated Jun. 15, 2022.
U.S. Appl. No. 17/894,882 Office Action dated Nov. 9, 2022.
U.S. Appl. No. 17/894,884 Office Action dated Nov. 9, 2022.
U.S. Appl. No. 17/894,885 Office Action dated Nov. 9, 2022.
USP 24 Official Monographs / Atropine, The United States Pharmacopeia 177-180 (2000).
Yam et al. Effect of Low-Concentration Atropine Eyedrops vs Placebo on Myopia Incidence in Children: The LAMP2 Randomized Clinical Trial. JAMA 329(6):472-481 (2023).
Yoshioka et al. Stability of Drugs and Dosage Forms 228 (2007).
Zhou et al. Chapter 5—Drug Stability and Degradation Studies. Developing Solid Oral Dosage Forms Pharmaceutical Theory And Practice 87-124 (Yihong Qiu et al. eds., 2009).
U.S. Appl. No. 16/785,411 Office Action dated Mar. 28, 2023.
U.S. Appl. No. 16/908,426 Office Action dated Mar. 28, 2023.
U.S. Appl. No. 17/894,882 Office Action dated Mar. 14, 2023.
U.S. Appl. No. 17/894,884 Office Action dated Mar. 14, 2023.
U.S. Appl. No. 17/894,885 Office Action dated Mar. 14, 2023.
U.S. Appl. No. 18/055,940 Office Action dated Apr. 26, 2023.
U.S. Appl. No. 18/055,945 Office Action dated May 11, 2023.
U.S. Appl. No. 18/055,949 Office Action dated May 11, 2023.

(56) References Cited

OTHER PUBLICATIONS

Shizhen Wang. Molecular Nuclear Medicine, Peking Union Medical College Press, the 1st Edition, Apr. 2004, p. 417, lines 9-10, published on Apr. 30, 2004.
U.S. Pat. No. 10,842,787 Judgement—Final Written Decision Denying Patent Owner's Motion to Exclude Determining All Challenged Claims Unpatentable 35 USC § 318(a) dated Jul. 13, 2023 (Case No. IPR2022-00384) (Paper No. 37).
U.S. Pat. No. 10,888,557 Judgement—Final Written Decision Denying Patent Owner's Motion to Exclude Determining All Challenged Claims Unpatentable 35 USC § 318(a) dated Jul. 13, 2023 (Case No. IPR2022-00415) (Paper No. 37).
U.S. Pat. No. 10,940,145 Judgement—Final Written Decision Denying Patent Owner's Motion to Exclude Determining All Challenged Claims Unpatentable 35 USC § 318(a) dated Jul. 13, 2023 (Case No. IPR2022-00414) (Paper No. 38).
U.S. Appl. No. 17/335,496 Office Action dated Aug. 7, 2023.
Abelson, Mark B et al. Demystifying Dumulcents. Review of Ophthalmology : pp. 1-4 (2006). Retrieved from Internet URL: https://www.reviewofophthalmology.com/article/demystifying-dumulcents.
Akorn, FDA Drug Label Archive for Atropine Sulfate Solution, NDC code 17478-215-02, available at [dailymed.nlm.nih.gov/dailymed/getArchivalFile.cfm?archive_id=25609] (2010).
Alonso, Maria Jose et al. The Potential of Chitosan in Ocular Drug Delivery. The Journal of Pharmacy and Pharmacology 55(11):1451-1463 (2003).
"Beckman-Coulter", available at www.beckman.com/resources/industry-standards/usp-790 (2021).
Chowhan, Masood, et al., Chapter 28: Essentials of Pharmaceuticals. Ophthalmic Preparations. (pp. 541-552) (2012).
Jiang Qiaoxi. Characteristics and Preparation of Dosage Forms of Ophthalmic Drugs. The Journal of Pharmacy 5(3-4):123-133 (1989).
Kumar, Sampath, et al., Recent Challenges and Advances in Ophthalmic Drug Delivery System. The Pharma Innovation 1:1-15 (2012).
Matthews, Brian, et al., Stability Storage and Testing of Ophthalmic Products for Global Registration. Drug Development and Industrial Pharmacy 26(12):1227-1237 (2000).
PCT/US2022/015092 International Search Report and Written Opinion dated May 30, 2022.
Pramar, Y. Compounding Ophthalmic Liquids. Xavier University of Louisiana, College of Pharmacy, New Orleans, Louisiana : pp. 1-11 (2012).
U.S. Appl. No. 16/785,411 Office Action dated Apr. 2, 2024.
U.S. Appl. No. 16/908,426 Office Action dated Apr. 1, 2024.
U.S. Appl. No. 17/335,496 Office Action dated Mar. 5, 2024.
U.S. Appl. No. 17/721,831 Office Action dated May 28, 2024.
U.S. Appl. No. 18/363,223 Office Action dated Mar. 6, 2024.
Buffer Capacity a an underestimated parameter in prep RP-HPLC. Kromasil ;May 2011. Available at URL: https://www.kromasil.com/notes/? NOTEhexi pp. 1-3.
Halder, Arindam et al. Physiochemical Properties and Cytotoxicity of a Benzalkonium Chloride-free, Micellar Emulsion Ophthalmic Formulation of Latanoprost. Clinical Ophthalmology 14:3057-3064 (2020).
U.S. Appl. No. 16/785,411 Office Action dated Sep. 10, 2024.
U.S. Appl. No. 16/908,426 Office Action dated Sep. 10, 2024.
U.S. Appl. No. 17/721,838 Office Action dated Sep. 5, 2024.

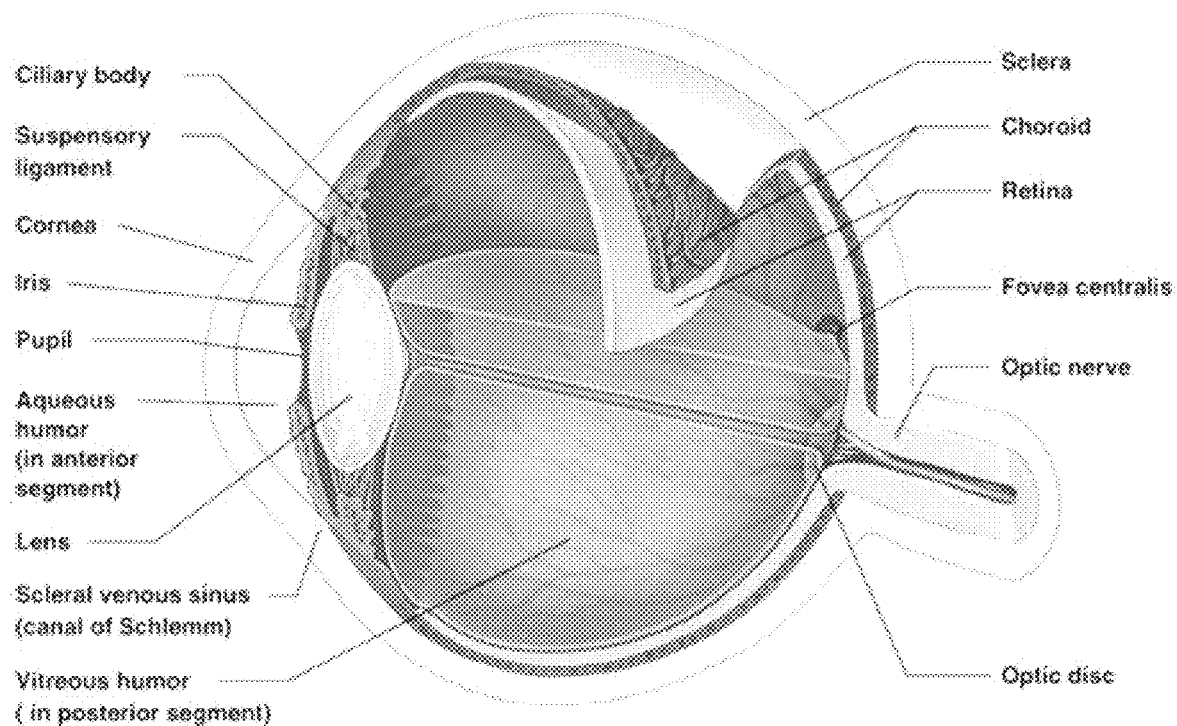

D₂O STABILIZED PHARMACEUTICAL FORMULATIONS

CROSS REFERENCE

This application is a continuation of U.S. application Ser. No. 16/805,612, filed Feb. 28, 2020, which is a continuation of U.S. application Ser. No. 15/578,202, filed Nov. 29, 2017, which is a U.S. National Phase of PCT/US2016/034823, filed May 27, 2016, which claims the benefit of U.S. Provisional Application No. 62/168,538, filed May 29, 2015, all of which are herein incorporated by reference in their entirety.

BACKGROUND OF THE DISCLOSURE

Pharmaceutical formulations have an expiration date which is based on the degradation of the active ingredient.

SUMMARY OF THE DISCLOSURE

Provided herein are $D_2O$ stabilized pharmaceutical compositions and formulations.

According to one aspect, an ophthalmic composition disclosed herein comprises an ophthalmic agent and deuterated water, at a pD of from about 4 to about 8.

According to another aspect, an ophthalmic composition disclosed herein comprises an ophthalmic agent and deuterated water, at a pD of from about 4 to about 8, wherein the ophthalmic agent is not a muscarinic antagonist, and wherein the ophthalmic agent does not extend singlet oxygen lifetime.

In some embodiments, the ophthalmic agent comprises aflibercept (also known as VEGF Trap), ranibizumab, pegaptanib, cyclopentolate, phenylephrine, homatropine, scopolamine, cyclopentolate/phenylephrine, phenylephrine/scopolamine, tropicamide, ketorolac/phenylephrine, hydroxyamphetamine/tropicamide, cysteamine, ocriplasmin, mitomycin, dapiprazole, lidocaine, proparacaine, tetracaine, benoxinate, azithromycin, bacitracin, besifloxacin, boric acid, chloramphenicol, ciprofloxacin, erythromycin, ganciclovir, gatifloxacin, gentamicin, idoxuridine, levofloxacin, moxifloxacin, natamycin, norfloxacin, ofloxacin, bacitracin/polymyxin b, tobramycin, polymyxin b/trimethoprim, povidone iodine, trifluridine, gramicidin/neomycin/polymyxin b, sulfacetamide sodium, sulfisoxazole, bacitracin/neomycin/polymyxin b, oxytetracycline/polymyxin b, phenylephrine/sulfacetamide sodium, vidarabine, bromfenac, nepafenac, ketorolac, cyclosporine, flurbiprofen, suprofen, diclofenac, alcaftadine, azelastine, bepotastine, cromolyn, emedastine, epinastine, ketotifen, levocabastine, lodoxamide, nedocromil, naphazoline, naphazoline/pheniramine, naphazoline/zinc sulfate, olopatadine, oxymetazoline, pemirolast, phenylephrine, phenylephrine/zinc sulfate, tetrahydrozoline, tetrahydrozoline/zinc sulfate, fluorescein, fluorescein/proparacaine, benoxinate/fluorescein, indocyanine green, trypan blue, acetylcholine, apraclonidine, betaxolol, bimatoprost, brimonidine, brinzolamide, brimonidine/brinzolamide, carbachol, carteolol, demecarium bromide, dipivefrin, dorzolamide, dorzolamide/timolol, echothiophate iodide, epinephrine, epinephrine/pilocarpine, latanoprost, levobunolol, levobetaxolol, metipranolol, physostigmine, pilocarpine, tafluprost, timolol, travoprost, unoprostone, artificial tear, dexamethasone, difluprednate, fluocinolone, fluorometholone, loteprednol, medrysone, prednisolone, rimexolone, triamcinolone, fluorometholone/sulfacetamide sodium, dexamethasone/neomycin, dexamethasone/tobramycin, dexamethasone/neomycin/polymyxin b, loteprednol/tobramycin, prednisolone/sulfacetamide sodium, bacitracin/hydrocortisone/neomycin/polymyxin b, hydrocortisone/neomycin/polymyxin b, chloramphenicol/hydrocortisone/polymyxin b, neomycin/polymyxin b/prednisolone, gentamicin/prednisolone, ketorolac/phenylephrine, diphenhydramine, dimenhydrinate, dicyclomine, flavoxate, oxybutynin, tiotropium, hyoscine, scopolomine (L-hyoscine), hydroxyzine, ipratropium, pirenzapine, solifenacin, darifenacin, benzatropine, mebeverine, procyclidine, aclidinium bromide, trihexyphenidyl/benzhexol, tolterodine, or any combinations thereof.

In some embodiments, the ophthalmic composition comprises at least about 80% of the ophthalmic agent based on initial concentration after extended period of time under storage condition. In some embodiments, the ophthalmic composition comprises at least about 85% of the ophthalmic agent based on initial concentration after extended period of time under storage condition. In some embodiments, the ophthalmic composition comprises at least about 90% of the ophthalmic agent based on initial concentration after extended period of time under storage condition. In some embodiments, the ophthalmic composition comprises at least about 95% of the ophthalmic agent based on initial concentration after extended period of time under storage condition. In some embodiments, the ophthalmic composition comprises at least about 97% of the ophthalmic agent based on initial concentration after extended period of time under storage condition. In some embodiments, the ophthalmic composition comprises at least about 98% of the ophthalmic agent based on initial concentration after extended period of time under storage condition. In some embodiments, the ophthalmic composition comprises at least about 99% of the ophthalmic agent based on initial concentration after extended period of time under storage condition.

In some embodiments, the ophthalmic composition has a pD of less than about 8 after extended period of time under storage condition. In some embodiments, the ophthalmic composition has a pD of less than about 7.5 after extended period of time under storage condition. In some embodiments, the ophthalmic composition has a pD of less than about 7 after extended period of time under storage condition. In some embodiments, the ophthalmic composition has a pD of less than about 6.5 after extended period of time under storage condition. In some embodiments, the ophthalmic composition has a pD of less than about 6 after extended period of time under storage condition. In some embodiments, the ophthalmic composition has a pD of less than about 5.5 after extended period of time under storage condition. In some embodiments, the ophthalmic composition has a pD of less than about 5 after extended period of time under storage condition. In some embodiments, the ophthalmic composition has a pD of less than about 4.5 after extended period of time under storage condition. In some embodiments, the ophthalmic composition has a pD of less than about 4 after extended period of time under storage condition.

In some embodiments, the ophthalmic composition has a pD that is about 0.4 unit higher than the measured pH.

In some embodiments, the ophthalmic composition further has a potency of at least 80% after extended period of time under storage condition. In some embodiments, the ophthalmic composition further has a potency of at least 85% after extended period of time under storage condition. In some embodiments, the ophthalmic composition further has a potency of at least 90% after extended period of time under storage condition. In some embodiments, the ophthalmic composition further has a potency of at least 93% after extended period of time under storage condition. In some embodiments, the ophthalmic composition further has a potency of at least 95% after extended period of time under storage condition. In some embodiments, the ophthalmic composition further has a potency of at least 97% after extended period of time under storage condition. In some embodiments, the ophthalmic composition further has a potency of at least 98% after extended period of time under storage condition. In some embodiments, the ophthalmic composition further has a potency of at least 99% after extended period of time under storage condition.

In some embodiments, the extended period of time is about 1 week. In some embodiments, extended period of time is about 2 weeks. In some embodiments, the extended period of time is about 3 weeks. In some embodiments, the extended period of time is about 1 month. In some embodiments, the extended period of time is about 2 months. In some embodiments, the extended period of time is about 3 months. In some embodiments the extended period of time is about 4 months. In some embodiments, the extended period of time is about 5 months. In some embodiments, the extended period of time is about 6 months. In some embodiments, the extended period of time is about 8 months. In some embodiments, the extended period of time is about 10 months. In some embodiments, the extended period of time is about 12 months. In some embodiments, the extended period of time is about 18 months. In some embodiments, the extended period of time is about 24 months. In some embodiments, the extended period of time is about 36 months. In some embodiments, the extended period of time is about 4 years. In some embodiments, the extended period of time is about 5 years.

In some embodiments, the ophthalmic composition comprises a storage condition that has a storage temperature of from about 16° C. to about 30° C. or about 20° C. to about 25° C. In some embodiments, the storage condition has a relative humidity of about 60%. In some embodiments, the ophthalmic composition comprises a storage condition that has a relative humidity of about 75%.

In some embodiments, the ophthalmic composition is in the form of an aqueous solution.

In some embodiments, the ophthalmic agent is present in the formulation at a concentration of from about 0.001 wt % to about 20 wt %.

In some embodiments, the ophthalmic composition further comprises an osmolarity adjusting agent. In some embodiments, the osmolarity adjusting agent is sodium chloride.

In some embodiments the ophthalmic composition further comprises a preservative. In some embodiments, the preservative is selected from benzalkonium chloride, cetrimonium, sodium perborate, stabilized oxychloro complex, Sof-Zia, polyquaternium-1, chlorobutanol, edetate disodium, polyhexamethylene biguanide, or combinations thereof.

In some embodiments, the ophthalmic composition further comprises a buffer agent. In some embodiments, the buffer agent is selected from borates, borate-polyol complexes, phosphate buffering agents, citrate buffering agents, acetate buffering agents, carbonate buffering agents, organic buffering agents, amino acid buffering agents, or combinations thereof.

In some embodiments, the ophthalmic composition further comprises a tonicity adjusting agent. In some embodiments, the tonicity adjusting agent is selected from sodium chloride, sodium nitrate, sodium sulfate, sodium bisulfate, potassium chloride, calcium chloride, magnesium chloride, zinc chloride, potassium acetate, sodium acetate, sodium bicarbonate, sodium carbonate, sodium thiosulfate, magnesium sulfate, disodium hydrogen phosphate, sodium dihydrogen phosphate, potassium dihydrogen phosphate, dextrose, mannitol, sorbitol, dextrose, sucrose, urea, propylene glycol, gly cerin, or a combination thereof.

In some embodiments, the ophthalmic composition is stored in a plastic container.

In some embodiments, the ophthalmic composition has a dose-to-dose ophthalmic agent concentration variation of less than 50%. In some embodiments, the ophthalmic composition has a dose-to-dose ophthalmic agent concentration variation of less than 40%. In some embodiments, the ophthalmic composition has a dose-to-dose ophthalmic agent concentration variation of less than 30%. In some embodiments, the ophthalmic composition has a dose-to-dose ophthalmic agent concentration variation of less than 20%. In some embodiments, the ophthalmic composition has a dose-to-dose ophthalmic agent concentration variation of less than 10%. In some embodiments, the ophthalmic composition has a dose-to-dose ophthalmic agent concentration variation of less than 5%.

In some embodiments, the dose-to-dose ophthalmic agent concentration variation is based on 10 consecutive doses. In some embodiments, the dose-to-dose ophthalmic agent concentration variation is based on 8 consecutive doses. In some embodiments, the dose-to-dose ophthalmic agent concentration variation is based on 5 consecutive doses. In some embodiments, the dose-to-dose ophthalmic agent concentration variation is based on 3 consecutive doses. In some embodiments, the dose-to-dose ophthalmic agent concentration variation is based on 2 consecutive doses.

In some embodiments, the ophthalmic composition has a pD of from about 4 to about 8. In some embodiments, the ophthalmic composition has a pD of from about 4.5 to about 7.5. In some embodiments the ophthalmic composition has a pD of from about 5 to about 7.0. In some embodiments, the ophthalmic composition has a pD of from about 6 to about 7.0.

In some embodiments, the ophthalmic composition further comprises a pD adjusting agent.

In some embodiments, the ophthalmic composition further comprises a pharmaceutically acceptable carrier. In some embodiments, the pharmaceutically acceptable carrier further comprises at least one viscosity-enhancing agent. In some embodiments, the viscosity-enhancing agent is selected from cellulose-based polymers, polyoxyethylene-polyoxypropylene triblock copolymers, dextran-based polymers, polyvinyl alcohol, dextrin, polyvinylpyrrolidone, polyalkylene glycols, chitosan, collagen, gelatin, hyaluronic acid, or combinations thereof.

In some embodiments, the ophthalmic composition comprises less than 60% of $H_2O$. In some embodiments, the ophthalmic composition comprises less than 55% of $H_2O$. In some embodiments, the ophthalmic composition comprises less than 50% of $H_2O$. In some embodiments, the ophthalmic composition comprises less than 45% of $H_2O$. In some embodiments, the ophthalmic composition comprises less than 40% of $H_2O$. In some embodiments, the ophthalmic composition comprises less than 35% of $H_2O$. In some embodiments, the ophthalmic composition comprises less than 30% of $H_2O$. In some embodiments, the ophthalmic composition comprises less than 25% of $H_2O$. In some embodiments, the ophthalmic composition comprises less than 20% of $H_2O$. In some embodiments, the ophthalmic composition comprises less than 15% of $H_2O$.

In some embodiments, the ophthalmic composition comprises less than 10% of $H_2O$. In some embodiments, the ophthalmic composition comprises less than 8% of $H_2O$. In some embodiments, the ophthalmic composition comprises less than 6% of $H_2O$. In some embodiments, the ophthalmic composition comprises less than 5% of $H_2O$. In some embodiments, the ophthalmic composition comprises less than 4% of $H_2O$. In some embodiments, the ophthalmic composition comprises less than 3% of $H_2O$. In some embodiments, the ophthalmic composition comprises less than 2% of $H_2O$. In some embodiments, the ophthalmic composition comprises less than 1% of $H_2O$. In some embodiments, the ophthalmic composition comprises less than 0.5% of $H_2O$. In some embodiments, the ophthalmic composition comprises less than 0.1% of $H_2O$. In some embodiments, the ophthalmic composition comprises 0% of $H_2O$.

In some embodiments, the ophthalmic composition is formulated as an ophthalmic solution for the treatment of an ophthalmic condition or disease.

In some embodiments, the ophthalmic agent is not atropine. In some embodiments, the ophthalmic agent is not atropine sulfate. In some embodiment, the ophthalmic agent is not a muscarinic antagonist.

In some embodiments, the ophthalmic agent is not an alpha-amino-carboxylic acid or an alpha-hydroxy-carboxylic acid. In some embodiments, the ophthalmic agent is not benactyzine hydrochloride.

In some embodiments, the ophthalmic agent quenches photogenerated singlet oxygen species in the composition. In some embodiments, the ophthalmic composition is not saturated with oxygen. In some embodiments, the ophthalmic composition does not comprise a photosensitizer.

In some embodiments, the ophthalmic agent is dissolved in the ophthalmic composition. In some embodiments, the ophthalmic agent is suspended in the ophthalmic composition.

According to another aspect, a method of treating an ophthalmic condition or disease comprises administering to an eye of an individual in need thereof an effective amount of the ophthalmic composition disclosed in the present disclosure. According to another aspect, a method of ameliorating or reducing an ophthalmic condition or disease comprises administering to an eye of an individual in need thereof an effective amount of the ophthalmic composition disclosed in the present disclosure.

In some embodiments, the ophthalmic composition is administered at predetermined time intervals over an extended period of time. In some embodiments, the ophthalmic composition is administered once a day. In some embodiments, the ophthalmic composition is administered once every day. In some embodiments, the ophthalmic composition is administered every other day. In some embodiments, the ophthalmic composition is administered over 1 week, 2 weeks, 1 month, 2 months, 3 months, 6 months, 1 year, 2 years, 3 years, 4 years, 5 years, 6 years, 7 years, 8 years, 9 years, 10 years, 11 years, or 12-15 years. In some embodiments, the ophthalmic composition is administered only once.

In some embodiments, the ophthalmic composition is stored below room temperature prior to first use. In some embodiments, the ophthalmic composition is stored at between about 2° C. to about 10° C. prior to first use. In some embodiments, the ophthalmic composition is stored at between about 4° C. to about 8° C. prior to first use.

In some embodiments the ophthalmic composition is stored at room temperature prior to first use. In some embodiments, the ophthalmic composition is stored at between about 16° C. to about 26° C. prior to first use.

In some embodiments, the ophthalmic composition is stored below room temperature after first use. In some embodiments, the ophthalmic composition is stored at between about 2° C. to about 10° C. after first use. In some embodiments, the ophthalmic composition is stored at between about 4° C. to about 8° C. after first use.

In some embodiments, the ophthalmic composition is stored at room temperature after first use. In some embodiments, the ophthalmic composition is stored at between about 16° C. to about 26° C. after first use.

Other features and technical effects of the methods and compositions described herein will become apparent from the following detailed description. It should be understood, however, that the detailed description and the specific examples, while indicating specific embodiments, are given by way of illustration only.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1 illustrates a conceptual representation of the eye anatomy.

DETAILED DESCRIPTION OF THE DISCLOSURE

The present disclosure recognizes that stability and eye tolerance are parameters to consider when formulating an ophthalmic composition. In some instances, to extend the shelf-life or stability of an ophthalmic composition, the pH of the composition is subsequently reduced. In some instances, the lowered pH reduces or prevents base catalyzed hydrolysis and thereby stabilizes the active agent. However, in some cases, the formulation with the reduced pH leads to poor eye tolerance as the acidic formulation stings the eye, leading to tear production. In such cases, the tears then dilute the composition and/or wash the composition out of the eye, thereby reducing the effectiveness of the ophthalmic composition.

In addition, the present disclosure recognizes that deuterated water stabilizes ophthalmic compositions. In some cases, the deuterated water is a weak acid as compared to $H_2O$, as such deuterated water comprises a lower concentration of the reactive species (e.g., —OD) which in some instances leads to base catalyzed hydrolysis of an active agent in the ophthalmic composition. As such, in some instances compositions comprising deuterated water leads to reduced base catalyzed hydrolysis when compared to compositions comprising $H_2O$. In some instances, deuterated water further lowers the buffering capacity of an ophthalmic composition, leading to less tear reflex in the eye.

Disclosed herein are ophthalmic compositions that comprise an ophthalmic agent and deuterated water, at a pD of from about 4 to about 8. Also disclosed herein are ophthalmic solutions that comprise an ophthalmic agent and deuterated water, at a pD of from about 4 to about 8. Further disclosed herein are methods of treating an ophthalmic condition or disease that comprises administering to an eye of an individual in need thereof an effective amount of an ophthalmic composition or an ophthalmic solution described infra. Additionally disclosed herein are methods of ameliorating or reducing an ophthalmic condition or disease that comprises administering to an eye of an individual in need thereof an effective amount of an ophthalmic composition or an ophthalmic solution described infra.

Ophthalmic Agents

Disclosed herein are pharmaceutical compositions formulated in the presence of deuterated water. As used herein, deuterated water refers to $D_2O$, DHO, heavy water, and/or deuterium oxide. In some instances, the pharmaceutical compositions are ophthalmic compositions containing one or more ophthalmic agents. In some cases, the ophthalmic compositions are formulated as an aqueous solution, gel, or as an ointment.

In some embodiments, the ophthalmic agents used in the ophthalmic compositions are susceptible to degradation through hydrolysis. In some embodiment, the ophthalmic agents used in the ophthalmic compositions are susceptible to degradation through base-catalyzed hydrolysis.

In some embodiments, ophthalmic agents include anti-angiogenic ophthalmic agents, mydriatics, antimydriatic agents, ophthalmic anesthetics, ophthalmic anti-infectives, ophthalmic anti-inflammatory agents, ophthalmic antihistamines and decongestants, ophthalmic diagnostic agents, ophthalmic glaucoma agents, ophthalmic lubricants and irrigation agents, ophthalmic steroids, ophthalmic steroids with anti-infectives, or ophthalmic surgical agents.

In some embodiments, an ophthalmic composition formulated in the presence of deuterated water include anti-angiogenic ophthalmic agents, mydriatics, antimydriatic agents, ophthalmic anesthetics, ophthalmic anti-infectives, ophthalmic anti-inflammatory agents, ophthalmic antihistamines and decongestants, ophthalmic diagnostic agents, ophthalmic glaucoma agents, ophthalmic lubricants and irrigation agents, ophthalmic steroids, ophthalmic steroids with anti-infectives, ophthalmic surgical agents, or combinations thereof.

Anti-angiogenic ophthalmic agents are vascular endothelial growth factor (VEGF) antagonists that prevent generation of new blood vessels by a process termed neovascularization. In some instances, anti-angiogenic ophthalmic agents are used to inhibit neovascularization in age related macular degeneration. In some instances, anti-angiogenic ophthalmic agents are used to treat diabetic macular edema, diabetic retinopathy, or macular edema. In some embodiments, macular edema is a swelling or thickening of the eye's macula, or the region of the eye responsible for central vision. In some embodiments, diabetic retinopathy refers to damages to the blood vessels in the retina. Exemplary anti-angiogenic ophthalmic agents include, but are not limited to, aflibercept (also known as VEGF Trap) (e.g., Eylea), ranibizumab (e.g., Lucentis), or pegaptanib (e.g., Macugen).

In some embodiments, an ophthalmic composition formulated in the presence of deuterated water includes anti-angiogenic ophthalmic agents such as for example aflibercept (also known as VEGF Trap), ranibizumab, or pegaptanib. In some embodiments, an ophthalmic composition formulated in the presence of deuterated water includes aflibercept (also known as VEGF Trap), ranibizumab, pegaptanib, or combinations thereof.

Mydriatic agents are agents that dilate the pupil of the eye. In some instances, mydriatics are used to treat eye dryness, redness, or itching, uveitis, organophosphate poisoning, or inflammary eye conditions such as iritis and cyclitis. Exemplary mydriatic agents include, but are not limited to, cyclopentolate (e.g., Cyclogyl, Ak-Pentolate, Cylate, Ocu-Pentolate, or Pentolair), phenylephrine (e.g., AK-Dilate, AK-Nefrin, Altafrin, Isopto Frin, Mydfrin, Neo-synephrine Ophthalmic, Neofrin, Ocu-Phrin, Prefrin, or Refresh Redness Relief), homatropine (e.g., Homatropaire, Isopto Homatropine), scopolamine (e.g., Isopto Hyoscine), cyclopentolate/phenylephrine (e.g., Cyclomydril), phenylephrine/scopolamine (e.g., Murocoll 2), tropicamide (e.g., Mydral, Ocu-Tropic, or Tropicacyl), ketorolac/phenylephrine (e.g., Omidria), orhydroxyamphetamine/tropicamide (e.g., Paremyd).

In some embodiments, an ophthalmic composition formulated in the presence of deuterated water includes mydriatic agents such as for example cyclopentolate, phenylephrine, homatropine, scopolamine, cyclopentolate/phenylephrine, phenylephrine/scopolamine, tropicamide, ketorolac/phenylephrine, orhydroxyamphetamine/tropicamide. In some embodiments, an ophthalmic composition formulated in the presence of deuterated water includes cyclopentolate, phenylephrine, homatropine, scopolamine, cyclopentolate/phenylephrine, phenylephrine/scopolamine, tropicamide, ketorolac/phenylephrine, hydroxyamphetamine/tropicamide, or combinations thereof. In some embodiments, an ophthalmic composition formulated in the presence of deuterated water does not include atropine, atropine sulfate, noratropine, atropine-N-oxide, tropine, tropic acid, or atropine methonitrate. In some embodiments, an ophthalmic composition formulated in the presence of deuterated water does not include atropine. In some embodiments, an ophthalmic composition formulated in the presence of deuterated water does not include atropine sulfate.

Antimydriatic agents are agents that decrease the size of the pupil. Exemplary antimydriatic agents include, but are not limited to, cysteamine (e.g., Cystaran), ocriplasmin (e.g., Jetrea), mitomycin (e.g., Mitosol), or dapiprazole (e.g., Rev-Eyes).

In some embodiments, an ophthalmic composition formulated in the presence of deuterated water includes antimydriatic agents such as for example cysteamine, ocriplasmin, mitomycin, or dapiprazole. In some embodiments, an ophthalmic composition formulated in the presence of deuterated water includes cysteamine, ocriplasmin, mitomycin, dapiprazole, or combinations thereof.

Ophthalmic anesthetics are local anesthetics that block pain signals at the nerve endings in the eyes. Exemplary ophthalmic anesthetics include, but are not limited to, lidocaine (e.g., Akten), proparacaine (e.g., Alcaine, Ocu-Caine, Ophthetic, or Parcaine), tetracaine (e.g., Altacaine, Opticaine, or TetraVisc), or benoxinate (or oxybuprocaine)(e.g., Novesine, Novesin).

In some embodiments, an ophthalmic composition formulated in the presence of deuterated water includes ophthalmic anesthetics such as for example lidocaine, proparacaine, tetracaine, or benoxinate. In some embodiments, an ophthalmic composition formulated in the presence of deuterated water includes lidocaine, proparacaine, tetracaine, benoxinate, or combinations thereof.

Ophthalmic anti-infectives are ophthalmic formulations that comprise antibiotics and/or antiviral agents. In some embodiments, ophthalmic anti-infectives are used to treat blepharitis, blepharoconjunctivitis, CMV retinitis, conjunctivitis, corneal ulcer, eye dryness or redness. Herpes Simplex dendritic keratitis, Herpetic keratitis, hordeolum, keratitis, keratoconjunctivitis, neonatal conjunctivitis, or trachoma, or are used during surgery. Exemplary ophthalmic anti-infectives include, but are not limited to, azithromycin (e.g., Azasite), bacitracin (e.g., AK-Tracin, Ocu-Tracin), besifloxacin (e.g., Besivance), boric acid (e.g., Collyrium Fresh), chloramphenicol (e.g., AK-Chlor. Chloromycetin ophthalmic, Chloroptic, Ocu-Chlor), ciprofloxacin (e.g., Ciloxan), erythromycin (e.g., Eyemycin, Ilotycin, Roymicin), ganciclovir (e.g., Vitrasert, Zirgan), gatifloxacin (e.g., Zymar, Zymaxid), gentamicin (e.g., Garamycin ophthalmic, Genoptic, Gentacidin, Gentak, Gentasol, Ocu-Mycin), idoxuridine (e.g., Herplex), levofloxacin (e.g., Iquix, Quixin), moxifloxacin (e.g., Vigamox, Moxeza), natamycin (e.g., Natacyn), norfloxacin (e.g., Chibroxin), ofloxacin (e.g., Ocuflox), bacitracin/polymyxin b (e.g., Polysporin ophthalmic, AK-Poly-Bac, Polycin-B, Polytracin ophthalmic), tobramycin (e.g., Tobrex, AK-Tob, Tomycine), polymyxin b/trimethoprim (e.g., Polytrim), povidone iodine (e.g., Betadine ophthalmic solution), trifluridine (e.g., Viroptic), gramicidin/neomycin/polymyxin b (e.g., AK-Spore, AK-Spore ointment, Neocidin ophthalmic solution), sulfacetamide sodium (e.g., AK-Sulf, Bleph-10, Cetamide, Isopto Cetamide), sulfisoxazole (e.g., Gantrisin ophthalmic), bacitracin/neomycin/polymyxin b (e.g., Neocidin, Neocin, Ocu-Spore-B, Ocutricin), oxytetracycline/polymyxin b (e.g., Terak, Tetramycin with Polymyxin B sulfate), phenylephrine/sulfacetamide sodium (e.g., Vasosulf), or vidarabine (e.g., Vira-A).

In some embodiments, an ophthalmic composition formulated in the presence of deuterated water includes ophthalmic anti-infectives such as for example azithromycin, bacitracin, besifloxacin, boric acid, chloramphenicol, ciprofloxacin, erythromycin, ganciclovir, gatifloxacin, gentamicin, idoxuridine, levofloxacin, moxifloxacin, natamycin, norfloxacin, ofloxacin, bacitracin/polymyxin b, tobramycin, polymyxin b/trimethoprim, povidone iodine, trifluridine, gramicidin/neomycin/polymyxin b, sulfacetamide sodium, sulfisoxazole, bacitracin/neomycin/polymyxin b, oxytetracycline/polymyxin b, phenylephrine/sulfacetamide sodium, or vidarabine. In some embodiments, an ophthalmic composition formulated in the presence of deuterated water includes azithromycin, bacitracin, besifloxacin, boric acid, chloramphenicol, ciprofloxacin, erythromycin, ganciclovir, gatifloxacin, gentamicin, idoxuridine, levofloxacin, moxifloxacin, natamycin, norfloxacin, ofloxacin, bacitracin/polymyxin b, tobramycin, polymyxin b/trimethoprim, povidone iodine, trifluridine, gramicidin/neomycin/polymyxin b, sulfacetamide sodium, sulfisoxazole, bacitracin/neomycin/polymyxin b, oxytetracycline/polymyxin b, phenylephrine/sulfacetamide sodium, vidarabine, or combinations thereof.

Ophthalmic anti-inflammatory agents are agents that reduce pain and/or inflammation of the eye. In some embodiments, ophthalmic anti-inflammatory agents are used to treat conjunctivitis, corneal ulcer, keratoconjunctivitis, keratoconjunctivitis sicca, postoperative increased intraocular pressure, postoperative ocular inflammation, or seasonal allergic conjunctivitis. In some embodiments, ophthalmic anti-inflammatory agents are used to inhibit intraoperative miosis. In some instances, ophthalmic anti-inflammatory agents are used during corneal refractive surgery. Exemplary ophthalmic anti-inflammatory agents include, but are not limited to, bromfenac (e.g., Bromday, Xibrom), nepafenac (e.g., Nevanac), ketorolac (e.g., Acular, Acular LS, Acular PF, Acuvail), cyclosporine (e.g., Restasis), flurbiprofen (e.g., Ocufen), suprofen (e.g., Profenal), or diclofenac (e.g., Voltaren ophthalmic).

In some embodiments, an ophthalmic composition formulated in the presence of deuterated water includes ophthalmic anti-inflammatory agents such as for example bromfenac, nepafenac, ketorolac, cyclosporine, flurbiprofen, suprofen, or diclofenac. In some embodiments, an ophthalmic composition formulated in the presence of deuterated water includes bromfenac, nepafenac, ketorolac, cyclosporine, flurbiprofen, suprofen, diclofenac, or combinations thereof.

Ophthalmic antihistamines are antihistamines that block the histamine receptors that cause for example runny eyes, redness, itching, and the like. Ophthalmic decongestants are sympathomimetic agents that relieve redness of the eye. Exemplary ophthalmic antihistamines and decongestants include, but are not limited to, alcaftadine (e.g., Lastacaft), azelastine (e.g., Optivar), bepotastine (e.g., Bepreve), cromolyn (e.g., Opticrom, Crolom), emedastine (e.g., Emadine), epinastine (e.g., Elestat), ketotifen (e.g., Alaway, Zaditor, Claritin Eye, Zyrtec Itchy Eye Drops), levocabastine (e.g., Livostin), lodoxamide (e.g., Alomide), nedocromil (e.g., Alocril), naphazoline (e.g., AK-Con, Albalon, All Clear, Allerest eye drops, Allersol, Clear Eyes, Ocu-Zoline, VasoClear, Vasocon), naphazoline/pheniramine (e.g., Visine-A, Opcon-A, Eye Allergy Relief), naphazoline/zinc sulfate (e.g., Clear Eyes ACR, VasoClear A), olopatadine (e.g., Patanol, Pataday, Pazeo), oxymetazoline (e.g., OcuClear), pemirolast (e.g., Alamast), phenylephrine (e.g., AK-Dilate, AK-Nefrin, Altafrin. Isopto Frin, Mydfrin, Neofrin, Ocu-Phrin, Prefrin, Refresh redness Relief), phenylephrine/zinc sulfate (e.g., Zincfrin), tetrahydrozoline (e.g., Visine original, Altazine, Geneyes, Opti-Clear, Optigene 3), or tetrahydrozoline/zinc sulfate (e.g., Visine totality multi-symptom relief).

In some embodiments, an ophthalmic composition formulated in the presence of deuterated water includes ophthalmic antihistamines and decongestants such as for example alcaftadine, azelastine, bepotastine, cromolyn, emedastine, epinastine, ketotifen, levocabastine, lodoxamide, nedocromil, naphazoline, naphazoline/pheniramine, naphazoline/zinc sulfate, olopatadine, oxymetazoline, pemirolast, phenylephrine, phenylephrine/zinc sulfate, tetrahydrozoline, or tetrahydrozoline/zinc sulfate. In some embodiments, an ophthalmic composition formulated in the presence of deuterated water includes alcaftadine, azelastine, bepotastine, cromolyn, emedastine, epinastine, ketotifen, levocabastine, lodoxamide, nedocromil, naphazoline, naphazoline/pheniramine, naphazoline/zinc sulfate, olopatadine, oxymetazoline, pemirolast, phenylephrine, phenylephrine/zinc sulfate, tetrahydrozoline, tetrahydrozoline/zinc sulfate, or combinations thereof.

Ophthalmic diagnostic agents are fluorescent molecules used for diagnostic fluorescein angiography or angioscopy of the retina and iris vasculature. Exemplary ophthalmic diagnostic agents include, but are not limited to, fluorescein (e.g., AK-Fluor, BioGlo, Ful-Glo), fluorescein/proparacaine (e.g., Flucaine, Fluoracaine), benoxinate/fluorescein (e.g., Flurox), indocyanine green (e.g., IC-Green), or trypan blue (e.g., MembraneBlue, VisinBlue).

In some embodiments, an ophthalmic composition formulated in the presence of deuterated water includes ophthalmic diagnostic agents such as for example fluorescein, fluorescein/proparacaine, benoxinate/fluorescein, indocyanine green, or try pan blue. In some embodiments, an ophthalmic composition formulated in the presence of deuterated water includes fluorescein, fluorescein/proparacaine, benoxinate/fluorescein, indocyanine green, try pan blue, or combinations thereof.

Ophthalmic glaucoma agents are agents that reduce eye pressure in glaucoma. In some instances, ophthalmic glaucoma agents are also used to treat intraocular hypertension, postoperative increased intraocular pressure, or production of miosis. Exemplary ophthalmic glaucoma agents include, but are not limited to, acetylcholine (e.g., Miochol-E), apraclonidine (e.g., Iopidine), betaxolol (e.g., Betoptic, Betoptic S), bimatoprost (e.g., Lumigan), brimonidine (e.g., Alphagan, Alphagan P), brinzolamide (e.g., Azopt), brimonidine/brinzolamide (e.g., Simbrinza), carbachol (e.g., Carbastat, Carboptic, Isopto Carbachol, Miostat), carteolol (e.g., Ocupress), demecarium bromide (e.g., Humorsol Ocumeter), dipivefrin (e.g., Propine), dorzolamide (e.g., Trusopt), dorzolamide/timolol (e.g., Cosopt, Cosopt PF, Combigan), echothiophate iodide (e.g., phospholine iodide), epinephrine (e.g., Epifrin, Epinal, Eppy/N, Glaucon), epinephrine/pilocarpine (e.g., E-Pilo-1, Epilo-2, P1E1, P2E1, P3E1, P4E1, P6E1), latanoprost (e.g., Xalatan), levobunolol (e.g., AK-Beta, Betagan), levobetaxolol (e.g., Betaxon), metipranolol (e.g., OptiPranolol), physostigmine (e.g., Eserine sulfate ophthalmic), pilocarpine (e.g., Isopto Carpine, Ocu-Carpine, Pilopine HS, Pilostat), tafluprost (e.g., Zioptan), timolol (e.g., Betimol, Timoptic Ocudose, Istalol, Timoptic, Timoptic-XE), travoprost (e.g., Travatan, Travatan Z, Izba), or unoprostone (e.g., Rescula).

In some embodiments, an ophthalmic composition formulated in the presence of deuterated water includes ophthalmic glaucoma agents such as for example acetylcholine, apraclonidine, betaxolol, bimatoprost, brimonidine, brinzolamide, brimonidine/brinzolamide, carbachol, carteolol, demecarium bromide, dipivefrin, dorzolamide, dorzolamide/timolol, echothiophate iodide, epinephrine, epinephrine/pilocarpine, latanoprost, levobunolol, levobetaxolol, metipranolol, physostigmine, pilocarpine, tafluprost, timolol, travoprost, or unoprostone. In some embodiments, an ophthalmic composition formulated in the presence of deuterated water includes acetylcholine, apraclonidine, betaxolol, bimatoprost, brimonidine, brinzolamide, brimonidine/brinzolamide, carbachol, carteolol, demecarium bromide, dipivefrin, dorzolamide, dorzolamide/timolol, echothiophate iodide, epinephrine, epinephrine/pilocarpine, latanoprost, levobunolol, levobetaxolol, metipranolol, physostigmine, pilocarpine, tafluprost, timolol, travoprost, unoprostone, or combinations thereof.

In some embodiments, ophthalmic lubricants and irrigation agents are used to treat dry and/or irritated eyes. Exemplary ophthalmic lubricants and irrigation agents include, but are not limited to, artificial tear from Hypotears, System Balance, FreshKote, GenTeal, TheraTears, Lacrisert, Tears Again, Lacri-Lube S.O.P. Systane, Oasis Tears, Artificial Tears, Celluvisc, Clear Eyes CLR, Comfort Tears, Dry Eye Relief, Isopto Tears, Liquitears, Lubricant Eye drops, Lubrifresh PM, Moisture Drops, Murocel, Opti-Free Rewetting Drops, Optive, Puralube Tears, Refresh, Soothe, Sterilube, Tears Naturale, Tears Renew, Ultra Fresh, or Visine Tears. In some embodiments, artificial tear preparations include carboxymethyl cellulose, polyvinyl alcohol, hydroxypropyl methylcellulose, hydroxypropyl cellulose, and hyaluronic acid.

In some embodiments, an ophthalmic composition formulated in the presence of deuterated water includes ophthalmic lubricants and irrigation agents such as for example artificial tear. In some embodiments, an ophthalmic composition formulated in the presence of deuterated water includes artificial tear.

In some embodiments, ophthalmic steroids are used to treat conjunctivitis, cyclitis, diabetic macular edema, eye dryness/redness/itches, eyelash hypotrichosis, iritis, keratitis, macular edema, postoperative ocular inflammation, rosacea, seasonal allergic conjunctivitis, steroid responsive inflammatory conditions, temporal arteritis, uveitis, or vitrectomy. Exemplary ophthalmic steroids include, but are not limited to, dexamethasone (e.g., Ozurdex, AK-Dex, Decadron Ocumeter, Dexasol, Maxidex, Ocu-Dex), difluprednate (e.g., Durezol), fluocinolone (e.g., Retisert, Iluvien), fluorometholone (e.g., FML Forte Liquifilm, Flarex, Fluor-Op. FML, FML S.O.P.), loteprednol (e.g., Alrex, Lotemax), medrysone (e.g., HMS), prednisolone (e.g., AK-Pred, Econopred, Econopred Plus, Inflamase Forte, Inflamase Mild, Omnipred, Pred Forte, Prednisol), rimexolone (e.g., Vexol), or triamcinolone (e.g., Triesence, Trivaris).

In some embodiments, an ophthalmic composition formulated in the presence of deuterated water includes ophthalmic steroids such as for example dexamethasone, difluprednate, fluocinolone, fluorometholone, loteprednol, medrysone, prednisolone, rimexolone, or triamcinolone. In some embodiments, an ophthalmic composition formulated in the presence of deuterated water includes dexamethasone, difluprednate, fluocinolone, fluorometholone, loteprednol, medrysone, prednisolone, rimexolone, triamcinolone, or combinations thereof.

Exemplary ophthalmic steroids with anti-infectives include, but are not limited to, fluorometholone/sulfacetamide sodium (e.g., FML-S Liquifilm), dexamethasone/neomycin (e.g., Neo-Decadron, AK-Neo-Dex, Neo-Decadron Ocumeter, Neo-Dex, Neo-Dexair), dexamethasone/tobramycin (e.g., TobraDex, Tobradex ST), dexamethasone/neomycin/polymyxin b (e.g., Neo-Poly-Dex, Maxitrol, AK-Trol, Dexacidin, Dexacine, Dexasporin, Methadex, Ocu-Trol), loteprednol/tobramycin (e.g., Zylet), prednisolone/sulfacetamide sodium (e.g., Blephamide, Blephamide S.O.P., AK-Cide, Cetapred, Isopto Cetapred, Metimyd, Ocu-Lone C, Vasocidin), bacitracin/hydrocortisone/neomycin/polymyxin b (e.g., Cortisporin Ophthalmic ointment, Cortomycin eye ointment. Neo-Poly-Bac, Neotricin HC, Triple Antibiotic HC ophthalmic ointment), hydrocortisone/neomycin/polymyxin b (e.g., Cortisporin ophthalmic suspension, Cortomycin suspension), chloramphenicol/hydrocortisone/polymyxin b (e.g., Ophthocort), neomycin/polymyxin b/prednisolone (e.g., Poly Pred), or gentamicin/prednisolone (e.g., Pred-G, Pred-G S.O.P.).

In some embodiments, an ophthalmic composition formulated in the presence of deuterated water includes ophthalmic steroids with anti-infectives such as for example fluorometholone/sulfacetamide sodium, dexamethasone/neomycin, dexamethasone/tobramycin, dexamethasone/neomycin/polymyxin b, loteprednol/tobramycin, prednisolone/sulfacetamide sodium, bacitracin/hydrocortisone/neomycin/polymyxin b, hydrocortisone/neomycin/polymyxin b, chloramphenicol/hydrocortisone/polymyxin b, neomycin/polymyxin b/prednisolone, or gentamicin/prednisolone. In some embodiments, an ophthalmic composition formulated in the presence of deuterated water includes fluorometholone/sulfacetamide sodium, dexamethasone/neomycin, dexamethasone/tobramycin, dexamethasone/neomycin/polymyxin b, loteprednol/tobramycin, prednisolone/sulfacetamide sodium, bacitracin/hydrocortisone/neomycin/polymyxin b, hydrocortisone/neomycin/polymyxin b, chloramphenicol/hydrocortisone/polymyxin b, neomycin/polymyxin b/prednisolone, gentamicin/prednisolone, or combinations thereof.

Exemplary ophthalmic surgical agents include, but are not limited to, ketorolac/phenylephrine (e.g., Omidria).

In some embodiments, an ophthalmic composition formulated in the presence of deuterated water includes ophthalmic surgical agents such as for example ketorolac/phenylephrine. In some embodiments, an ophthalmic composition formulated in the presence of deuterated water includes ketorolac/phenylephrine.

In some embodiments, an ophthalmic composition formulated in the presence of deuterated water includes diphenhydramine, dimenhydrinate, dicyclomine, flavoxate, oxybutynin, tiotropium, hyoscine, scopolomine (L-hyoscine), hydroxyzine, ipratropium, pirenzapine, solifenacin, darifenacin, benzatropine, mebeverine, procyclidine, aclidinium bromide, trihexyphenidyl/benzhexol, tolterodine, or a combination thereof.

In some embodiments, an ophthalmic composition formulated in the presence of deuterated water includes aflibercept (also known as VEGF Trap), ranibizumab, pegaptanib, cyclopentolate, phenylephrine, homatropine, scopolamine, cyclopentolate/phenylephrine, phenylephrine/scopolamine, tropicamide, ketorolac/phenylephrine, hydroxyamphetamine/tropicamide, cysteamine, ocriplasmin, mitomycin, dapiprazole, lidocaine, proparacaine, tetracaine, benoxinate, azithromycin, bacitracin, besifloxacin, boric acid, chloramphenicol, ciprofloxacin, erythromycin, ganciclovir, gatifloxacin, gentamicin, idoxuridine, levofloxacin, moxifloxacin, natamycin, norfloxacin, ofloxacin, bacitracin/polymyxin b, tobramycin, polymyxin b/trimethoprim, povidone iodine, trifluridine, gramicidin/neomycin/polymyxin b, sulfacetamide sodium, sulfisoxazole, bacitracin/neomycin/polymyxin b, oxytetracycline/polymyxin b, phenylephrine/sulfacetamide sodium, vidarabine, bromfenac, nepafenac, ketorolac, cyclosporine, flurbiprofen, suprofen, diclofenac, alcaftadine, azelastine, bepotastine, cromolyn, emedastine, epinastine, ketotifen, levocabastine, lodoxamide, nedocromil, naphazoline, naphazoline/pheniramine, naphazoline/zinc sulfate, olopatadine, oxymetazoline, pemirolast, phenylephrine, phenylephrine/zinc sulfate, tetrahydrozoline, tetrahydrozoline/zinc sulfate, fluorescein, fluorescein/proparacaine, benoxinate/fluorescein, indocyanine green, trypan blue, acetylcholine, apraclonidine, betaxolol, bimatoprost, brimonidine, brinzolamide, brimonidine/brinzolamide, carbachol, carteolol, demecarium bromide, dipivefrin, dorzolamide, dorzolamide/timolol, echothiophate iodide, epinephrine, epinephrine/pilocarpine, latanoprost, levobunolol, levobetaxolol, metipranolol, physostigmine, pilocarpine, tafluprost, timolol, travoprost, unoprostone, artificial tear, dexamethasone, difluprednate, fluocinolone, fluorometholone, loteprednol, medrysone, prednisolone, rimexolone, triamcinolone, fluorometholone/sulfacetamide sodium, dexamethasone/neomycin, dexamethasone/tobramycin, dexamethasone/neomycin/polymyxin b, loteprednol/tobramycin, prednisolone/sulfacetamide sodium, bacitracin/hydrocortisone/neomycin/polymyxin b, hydrocortisone/neomycin/polymyxin b, chloramphenicol/hydrocortisone/polymyxin b, neomycin/polymyxin b/prednisolone, gentamicin/prednisolone, ketorolac/phenylephrine, diphenhydramine, dimenhydrinate, dicyclomine, flavoxate, oxybutynin, tiotropium, hyoscine, scopolomine (L-hyoscine), hydroxyzine, ipratropium, pirenzapine, solifenacin, darifenacin, benzatropine, mebeverine, procyclidine, aclidinium bromide, trihexyphenidyl/benzhexol, tolterodine, or any combinations thereof.

Ophthalmic Composition

Provided herein is an ophthalmic composition for the treatment of an ophthalmic disorder or condition in which the ophthalmic composition is formulated with deuterated water. In some aspects, the ophthalmic composition is stable at different temperatures, at different relative humidity, and with a potency of at least 80% relative to the ophthalmic agent. In additional aspects, the ophthalmic composition has a lowered buffering capacity. In such instances, the lowered buffering capacity of the ophthalmic composition when administered into the eye allows the ophthalmic composition to reach physiological pH at a faster rate than compared to an equivalent ophthalmic formulation or solution formulated in $H_2O$.

In some aspects, described herein is an ophthalmic composition that does not have a dose-to-dose variation. In some aspects, described herein is an ophthalmic composition that is stable at different temperatures, at different relative humidity, and with a potency of at least 80% relative to the ophthalmic agent.

In other aspects, described herein include formulating the ophthalmic composition as an ophthalmic gel or an ophthalmic ointment. For example, some ophthalmic gel or an ophthalmic ointment described herein allows desirable dose-to-dose uniformity, increased stability, reduced or limited systemic exposure, or combinations thereof.

Ophthalmic Solution Composition or Formulation

Disclosed herein, in certain embodiments, is an ophthalmic composition formulated as an aqueous solution. In some embodiments, the ophthalmic composition comprises an ophthalmic agent and deuterated water. As used herein, deuterated water refers to $D_2O$, DHO, heavy water, and/or deuterium oxide.

In some embodiments, the composition comprises at least about 80% of the ophthalmic agent for an extended period of time under storage condition. In some embodiments, the composition comprises at least about 81% of the ophthalmic agent for an extended period of time under storage condition. In some embodiments, the composition comprises at least about 82% of the ophthalmic agent for an extended period of time under storage condition. In some embodiments, the composition comprises at least about 83% of the ophthalmic agent for an extended period of time under storage condition. In some embodiments, the composition comprises at least about 84% of the ophthalmic agent for an extended period of time under storage condition. In some embodiments, the composition comprises at least about 85% of the ophthalmic agent for an extended period of time under storage condition. In some embodiments, the composition comprises at least about 86% of the ophthalmic agent for an extended period of time under storage condition. In some embodiments, the composition comprises at least about 87% of the ophthalmic agent for an extended period of time under storage condition. In some embodiments, the composition comprises at least about 88% of the ophthalmic agent for an extended period of time under storage condition. In some embodiments, the composition comprises at least about 89% of the ophthalmic agent for an extended period of time under storage condition. In some embodiments, the composition comprises at least about 90% of the ophthalmic agent for an extended period of time under storage condition. In some embodiments, the composition comprises at least about 91% of the ophthalmic agent for an extended period of time under storage condition. In some embodiments, the composition comprises at least about 92% of the ophthalmic agent for an extended period of time under storage condition. In some embodiments, the composition comprises at least about 93% of the ophthalmic agent for an extended period of time under storage condition. In some embodiments, the composition comprises at least about 94% of the ophthalmic agent for an extended period of time under storage condition. In some embodiments, the composition comprises at least about 95% of the ophthalmic agent for an extended period of time under storage condition. In some embodiments, the composition comprises at least about 96% of the ophthalmic agent for an extended period of time under storage condition. In some embodiments, the composition comprises at least about 97% of the ophthalmic agent for an extended period of time under storage condition. In some embodiments, the composition comprises at least about 98% of the ophthalmic agent for an extended period of time under storage condition. In some embodiments, the composition comprises at least about 99% of the ophthalmic agent for an extended period of time under storage condition. In some embodiments, the composition comprises at least about 99.5% of the ophthalmic agent for an extended period of time under storage condition. In some embodiments, the composition comprises at least about 99.9% of the ophthalmic agent for an extended period of time under storage condition.

In some embodiments, the composition has a potency of at least about 80% after extended period of time under storage condition. In some embodiments, the composition has a potency of at least about 81% after extended period of time under storage condition. In some embodiments, the composition has a potency of at least about 82% after extended period of time under storage condition. In some embodiments, the composition has a potency of at least about 83% after extended period of time under storage condition. In some embodiments, the composition has a potency of at least about 84% after extended period of time under storage condition. In some embodiments, the composition has a potency of at least about 85% after extended period of time under storage condition. In some embodiments, the composition has a potency of at least about 86% after extended period of time under storage condition. In some embodiments, the composition has a potency of at least about 87% after extended period of time under storage condition. In some embodiments, the composition has a potency of at least about 88% after extended period of time under storage condition. In some embodiments, the composition has a potency of at least about 89% after extended period of time under storage condition. In some embodiments, the composition has a potency of at least about 90% after extended period of time under storage condition. In some embodiments, the composition has a potency of at least about 91% after extended period of time under storage condition. In some embodiments, the composition has a potency of at least 92% after extended period of time under storage condition. In some embodiments, the composition has a potency of at least 93% after extended period of time under storage condition. In some embodiments, the composition has a potency of at least 94% after extended period of time under storage condition. In some embodiments, the composition has a potency of at least 95% after extended period of time under storage condition. In some embodiments, the composition has a potency of at least 96% after extended period of time under storage condition. In some embodiments, the composition has a potency of at least 97% after extended period of time under storage condition. In some embodiments, the composition has a potency of at least 98% after extended period of time under storage condition. In some embodiments, the composition has a potency of at least 99% after extended period of time under storage condition.

In some embodiments, the extended period of time is at least 1 week. In some embodiments, the extended period of time is at least 2 weeks. In some embodiments, the extended period of time is at least 3 weeks. In some embodiments, the extended period of time is at least 1 month. In some embodiments, the extended period of time is at least 2 months. In some embodiments, the extended period of time is at least 3 months. In some embodiments, the extended period of time is at least 4 months. In some embodiments, the extended period of time is at least 5 months. In some embodiments, the extended period of time is at least 6 months. In some embodiments, the extended period of time is at least 7 months. In some embodiments, the extended period of time is at least 8 months. In some embodiments, the extended period of time is at least 9 months. In some embodiments, the extended period of time is at least 10 months. In some embodiments, the extended period of time is at least 11 months. In some embodiments, the extended period of time is at least 12 months (i.e. 1 year). In some embodiments, the extended period of time is at least 18 months (i.e. 1.5 years). In some embodiments, the extended period of time is at least 24 months (i.e. 2 years). In some embodiments, the extended period of time is at least 36 months (i.e. 3 years). In some embodiments, the extended period of time is at least 3 years. In some embodiments, the extended period of time is at least 5 years, 6 years, 7 years, 8 years, 9 years, 10 years, 15 years, 30 years, or more.

In some embodiments, the temperature of the storage condition is between about 2° C. and about 70° C. In some embodiments, the temperature of the storage condition is between about 2° C. and about 65° C., about 8° C. and about 65° C. about 10° C. and about 65° C., about 25° C. and about 65° C., about 30° C. and about 60° C., about 35° C. and about 55° C., or about 40° C. and about 50° C. In some embodiments, the temperature of the storage condition is between about 2° C. and about 10° C. In some embodiments, the temperature of the storage condition is between about 20° C. and about 26° C. In some embodiments, the temperature of the storage condition is about 25° C. In some embodiments, the temperature of the storage condition is about 40° C. In some embodiments, the temperature of the storage condition is about 60° C.

In some embodiments, the relative humidity of the storage condition is between about 50% and about 80%, or between about 60% and about 75%. In some embodiments, the relative humidity of the storage condition is about 60%. In some embodiments, the relative humidity of the storage condition is about 75%.

In some embodiments, the composition comprises less than 60% of $H_2O$. In some embodiments, the composition comprises less than 55% of $H_2O$. In some embodiments, the composition comprises less than 50% of $H_2O$. In some embodiments, the composition comprises less than 45% of $H_2O$. In some embodiments, the composition comprises less than 40% of $H_2O$. In some embodiments, the composition comprises less than 35% of $H_2O$. In some embodiments, the composition comprises less than 30% of $H_2O$. In some embodiments, the composition comprises less than 25% of $H_2O$. In some embodiments, the composition comprises less than 20% of $H_2O$. In some embodiments, the composition comprises less than 15% of $H_2O$. In some embodiments, the composition comprises less than 10% of $H_2O$. In some embodiments, the composition comprises less than 9% of $H_2O$. In some embodiments, the composition comprises less than 8% of $H_2O$. In some embodiments, the composition comprises less than 7% of $H_2O$. In some embodiments, the composition comprises less than 6% of $H_2O$.

In some embodiments, the composition comprises from less than 5% of $H_2O$ to less than 0.1% of $H_2O$. In some embodiments, the composition comprises less than 5% of $H_2O$. In some embodiments, the composition comprises less than 4.5% of $H_2O$. In some embodiments, the composition comprises less than 4% of $H_2O$. In some embodiments, the composition comprises less than 3.5% of $H_2O$. In some embodiments, the composition comprises less than 3% of $H_2O$. In some embodiments, the composition comprises less than 2.5% of $H_2O$. In some embodiments, the composition comprises less than 2% of $H_2O$. In some embodiments, the composition comprises less than 1.5% of $H_2O$. In some embodiments, the composition comprises less than 1% of $H_2O$. In some embodiments, the composition comprises less than 0.5% of $H_2O$. In some embodiments, the composition comprises less than 0.4% of $H_2O$. In some embodiments, the composition comprises less than 0.3% of $H_2O$. In some embodiments, the composition comprises less than 0.2% of $H_2O$. In some embodiments, the composition comprises less than 0.1% of $H_2O$. In some embodiments, the composition comprises 0% of $H_2O$.

In some embodiments, the composition has a pD of between about 3 and about 9, about 4 and about 8, about 4.5 and about 7.8, about 5 and about 7.5, or about 5.5 and about 7. In some embodiments, the composition has a pD of less than about 8. In some embodiments, the composition has a pD of less than about 7.9. In some embodiments, the composition has a pD of less than about 7.8. In some embodiments, the composition has a pD of less than about 7.7. In some embodiments, the composition has a pD of less than about 7.6. In some embodiments, the composition has a pD of less than about 7.5. In some embodiments, the composition has a pD of less than about 7.4. In some embodiments, the composition has a pD of less than about 7.3. In some embodiments, the composition has a pD of less than about 7.2. In some embodiments, the composition has a pD of less than about 7.1. In some embodiments, the composition has a pD of less than about 7. In some embodiments, the composition has a pD of less than about 6.9. In some embodiments, the composition has a pD of less than about 6.8. In some embodiments, the composition has a pD of less than about 6.7. In some embodiments, the composition has a pD of less than about 6.6. In some embodiments, the composition has a pD of less than about 6.5. In some embodiments, the composition has a pD of less than about 6.4. In some embodiments, the composition has a pD of less than about 6.3. In some embodiments, the composition has a pD of less than about 6.2. In some embodiments, the composition has a pD of less than about 6.1. In some embodiments, the composition has a pD of less than about 6. In some embodiments, the composition has a pD of less than about 5.9. In some embodiments, the composition has a pD of less than about 5.8. In some embodiments, the composition has a pD of less than about 5.7. In some embodiments, the composition has a pD of less than about 5.6. In some embodiments, the composition has a pD of less than about 5.5. In some embodiments, the composition has a pD of less than about 5.4. In some embodiments, the composition has a pD of less than about 5.3. In some embodiments, the composition has a pD of less than about 5.2. In some embodiments, the composition has a pD of less than about 5.1. In some embodiments, the composition has a pD of less than about 5. In some embodiments, the composition has a pD of less than about 4.9. In some embodiments, the composition has a pD of less than about 4.8. In some embodiments, the composition has a pD of less than about 4.7. In some embodiments, the composition has a pD of less than about 4.6. In some embodiments, the composition has a pD of less than about 4.5. In some embodiments, the composition has a pD of less than about 4.4. In some embodiments, the composition has a pD of less than about 4.3. In some embodiments, the composition has a pD of less than about 4.2. In some embodiments, the composition has a pD of less than about 4.1. In some embodiments, the composition has a pD of less than about 4. In some embodiments, the composition has a pD of less than about 3.9. In some embodiments, the composition has a pD of less than about 3.8. In some embodiments, the composition has a pD of less than about 3.7. In some embodiments, the composition has a pD of less than about 3.6. In some embodiments, the composition has a pD of less than about 3.5.

In some embodiments, the composition comprising deuterated water has a lowered buffering capacity than an equivalent composition comprising $H_2O$. As described elsewhere herein, in some embodiments, the lowered buffering capacity allows the composition comprising deuterated water to normalize to physiological pH at a faster rate than a composition comprising $H_2O$. In some embodiments, the lowered buffering capacity allows the composition to induce less tear reflex than an equivalent composition comprising $H_2O$.

In some instances, the composition comprising deuterated water stabilizes the ophthalmic agent. In some embodiments, this is due to a lower concentration of the reactive species (e.g., —OD) in the $D_2O$ aqueous system compared to the concentration of the reactive species (e.g., —OH) in an equivalent $H_2O$ aqueous system. In some cases, base catalysis leads to the presence of degradant from the ophthalmic agent. In some cases, with a lower concentration of the reactive species that causes degradant formation, the ophthalmic solution is more stable in a $D_2O$ aqueous system than compared to an equivalent $H_2O$ aqueous system. In some embodiments, the ophthalmic composition formulated with deuterated water allows for a more stable ophthalmic composition relative to the ophthalmic composition formulated with $H_2O$.

In some embodiments, the composition comprises less than 20% of major degradant based on the concentration of the ophthalmic agent after extended period of time under storage condition. In some embodiments, the composition comprises less than 15% of major degradant based on the concentration of the ophthalmic agent after extended period of time under storage condition. In some embodiments, the composition comprises less than 10% of major degradant based on the concentration of the ophthalmic agent after extended period of time under storage condition. In some embodiments, the composition comprises less than 5% of major degradant based on the concentration of the ophthalmic agent after extended period of time under storage condition. In some embodiments, the composition comprises less than 2.5% of major degradant based on the concentration of the ophthalmic agent after extended period of time under storage condition. In some embodiments, the composition comprises less than 2.0% of major degradant based on the concentration of the ophthalmic agent after extended period of time under storage condition. In some embodiments, the composition comprises less than 1.5% of major degradant based on the concentration of the ophthalmic agent after extended period of time under storage condition. In some embodiments, the composition comprises less than 1.0% of major degradant based on the concentration of the ophthalmic agent after extended period of time under storage condition. In some embodiments, the composition comprises less than 0.5% of major degradant based on the concentration of the ophthalmic agent after extended period of time under storage condition. In some embodiments, the composition comprises less than 0.4% of major degradant based on the concentration of the ophthalmic agent after extended period of time under storage condition. In some embodiments, the composition comprises less than 0.3% of major degradant based on the concentration of the ophthalmic agent after extended period of time under storage condition. In some embodiments, the composition comprises less than 0.2% of major degradant based on the concentration of the ophthalmic agent after extended period of time under storage condition. In some embodiments, the composition comprises less than 0.1% of major degradant based on the concentration of the ophthalmic agent after extended period of time under storage condition.

In some embodiments, the composition does not extend singlet oxygen lifetime upon irradiation with UV. In some instances, one or more of the ophthalmic agents described herein does not extend singlet oxygen lifetime upon irradiation with UV. In some instances, one or more of the ophthalmic agents described herein is a radical scavenger, which quenches photogenerated singlet oxygen species within the composition. In some instances, one or more of the ophthalmic agents selected from: aflibercept, ranibizumab, pegaptanib, cyclopentolate, phenylephrine, homatropine, scopolamine, cyclopentolate/phenylephrine, phenylephrine/scopolamine, tropicamide, ketorolac/phenylephrine, hydroxyamphetamine/tropicamide, cysteamine, ocriplasmin, mitomycin, dapiprazole, lidocaine, proparacaine, tetracaine, benoxinate, azithromycin, bacitracin, besifloxacin, boric acid, chloramphenicol, ciprofloxacin, erythromycin, ganciclovir, gatifloxacin, gentamicin, idoxuridine, levofloxacin, moxifloxacin, natamycin, norfloxacin, ofloxacin, bacitracin/polymyxin b, tobramycin, polymyxin b/trimethoprim, povidone iodine, trifluridine, gramicidin/neomycin/polymyxin b, sulfacetamide sodium, sulfisoxazole, bacitracin/neomycin/polymyxin b, oxytetracycline/polymyxin b, phenylephrine/sulfacetamide sodium, vidarabine, bromfenac, nepafenac, ketorolac, cyclosporine, flurbiprofen, suprofen, diclofenac, alcaftadine, azelastine, bepotastine, cromolyn, emedastine, epinastine, ketotifen, levocabastine, lodoxamide, nedocromil, naphazoline, naphazoline/pheniramine, naphazoline/zinc sulfate, olopatadine, oxymetazoline, pemirolast, phenylephrine, phenylephrine/zinc sulfate, tetrahydrozoline, tetrahydrozoline/zinc sulfate, fluorescein, fluorescein/proparacaine, benoxinate/fluorescein, indocyanine green, trypan blue, acetylcholine, apraclonidine, betaxolol, bimatoprost, brimonidine, brinzolamide, brimonidine/brinzolamide, carbachol, carteolol, demecarium bromide, dipivefrin, dorzolamide, dorzolamide/timolol, echothiophate iodide, epinephrine, epinephrine/pilocarpine, latanoprost, levobunolol, levobetaxolol, metipranolol, physostigmine, pilocarpine, tafluprost, timolol, travoprost, unoprostone, artificial tear, dexamethasone, difluprednate, fluocinolone, fluorometholone, loteprednol, medrysone, prednisolone, rimexolone, triamcinolone, fluorometholone/sulfacetamide sodium, dexamethasone/neomycin, dexamethasone/tobramycin, dexamethasone/neomycin/polymyxin b, loteprednol/tobramycin, prednisolone/sulfacetamide sodium, bacitracin/hydrocortisone/neomycin/polymyxin b, hydrocortisone/neomycin/polymyxin b, chloramphenicol/hydrocortisone/polymyxin b, neomycin/polymyxin b/prednisolone, gentamicin/prednisolone, ketorolac/phenylephrine, diphenhydramine, dimenhydrinate, dicyclomine, flavoxate, oxybutynin, tiotropium, hyoscine, scopolomine (L-hyoscine), hydroxyzine, ipratropium, pirenzapine, solifenacin, darifenacin, benzatropine, mebeverine, procyclidine, aclidinium bromide, trihexyphenidyl/benzhexol, and tolterodine, does not extend singlet oxygen lifetime upon irradiation with UV or quenches photogenerated singlet oxygen species within the composition. In some cases, the ophthalmic agent is not an alpha-amino-carboxylic acid or an alpha-hydroxy-carboxylic acid. In some cases, the ophthalmic agent is not benactyzine hydrochloride. In some cases, the ophthalmic composition is not saturated with oxygen. In additional cases, the ophthalmic composition does not comprise a photosensitizer.

Ophthalmic Agent Concentration

In some embodiments, the compositions described herein have a concentration of ophthalmic agent between about 0.001% to about 20%, between about 0.005% to about 10%, between about 0.010% to about 5%, between about 0.015% to about 1%, between about 0.020% to about 0.5%, between about 0.025% to about 0.1%, between about 0.030% to about 0.050%, between about 0.035% to about 0.050%, between about 0.040% to about 0.050%, or between about 0.045% to about 0.050% of the ophthalmic agent, or pharmaceutically acceptable prodrug or salt thereof, by weight of the composition. In some instances, the prodrug of the ophthalmic agent is chemically converted into the ophthalmic agent after the administration of the ophthalmic composition. In a non-limiting example, the ophthalmic prodrug has a chemical bond that is cleavable by one or more enzymes in tears. In some embodiments, the ophthalmic agent is aflibercept (also known as VEGF Trap), ranibizumab, pegaptanib, cyclopentolate, phenylephrine, homatropine, scopolamine, cyclopentolate/phenylephrine, phenylephrine/scopolamine, tropicamide, ketorolac/phenylephrine, hydroxyamphetamine/tropicamide, cysteamine, ocriplasmin, mitomycin, dapiprazole, lidocaine, proparacaine, tetracaine, benoxinate, azithromycin, bacitracin, besifloxacin, boric acid, chloramphenicol, ciprofloxacin, erythromycin, ganciclovir, gatifloxacin, gentamicin, idoxuridine, levofloxacin, moxifloxacin, natamycin, norfloxacin, ofloxacin, bacitracin/polymyxin b, tobramycin, polymyxin b/trimethoprim, povidone iodine, trifluridine, gramicidin/neomycin/polymyxin b, sulfacetamide sodium, sulfisoxazole, bacitracin/neomycin/polymyxin b, oxytetracycline/polymyxin b, phenylephrine/sulfacetamide sodium, vidarabine, bromfenac, nepafenac, ketorolac, cyclosporine, flurbiprofen, suprofen, diclofenac, alcaftadine, azelastine, bepotastine, cromolyn, emedastine, epinastine, ketotifen, levocabastine, lodoxamide, nedocromil, naphazoline, naphazoline/pheniramine, naphazoline/zinc sulfate, olopatadine, oxymetazoline, pemirolast, phenylephrine, phenylephrine/zinc sulfate, tetrahydrozoline, tetrahydrozoline/zinc sulfate, fluorescein, fluorescein/proparacaine, benoxinate/fluorescein, indocyanine green, trypan blue, acetylcholine, apraclonidine, betaxolol, bimatoprost, brimonidine, brinzolamide, brimonidine/brinzolamide, carbachol, carteolol, demecarium bromide, dipivefrin, dorzolamide, dorzolamide/timolol, echothiophate iodide, epinephrine, epinephrine/pilocarpine, latanoprost, levobunolol, levobetaxolol, metipranolol, physostigmine, pilocarpine, tafluprost, timolol, travoprost, unoprostone, artificial tear, dexamethasone, difluprednate, fluocinolone, fluorometholone, loteprednol, medrysone, prednisolone, rimexolone, triamcinolone, fluorometholone/sulfacetamide sodium, dexamethasone/neomycin, dexamethasone/tobramycin, dexamethasone/neomycin/polymyxin b, loteprednol/tobramycin, prednisolone/sulfacetamide sodium, bacitracin/hydrocortisone/neomycin/polymyxin b, hydrocortisone/neomycin/polymyxin b, chloramphenicol, hydrocortisone/polymyxin b, neomycin/polymyxin b/prednisolone, gentamicin/prednisolone, ketorolac/phenylephrine, diphenhydramine, dimenhydrinate, dicyclomine, flavoxate, oxybutynin, tiotropium, hyoscine, scopolomine (L-hyoscine), hydroxyzine, ipratropium, pirenzapine, solifenacin, darifenacin, benzatropine, mebeverine, procyclidine, aclidinium bromide, trihexyphenidyl/benzhexol, or tolterodine.

As described herein, the ophthalmic agent includes optically pure stereoisomers, optically enriched stereoisomers, and a racemic mixture of stereoisomers. For example, some ophthalmic compositions disclosed herein includes racemic mixture of D- and L-isomers; and some ophthalmic compositions disclosed herein includes optically enriched in favor of an ophthalmically active L-isomer.

Aqueous Solution Stability

In some embodiments, the composition described herein comprises a buffer. In some embodiments, a buffer is selected from borates, borate-polyol complexes, phosphate buffering agents, citrate buffering agents, acetate buffering agents, carbonate buffering agents, organic buffering agents, amino acid buffering agents, or combinations thereof. In some embodiments, the composition described herein comprises buffer comprising deuterated water. In some embodiments, a deuterated buffer is selected from borates, borate-polyol complexes, phosphate buffering agents, citrate buffering agents, acetate buffering agents, carbonate buffering agents, organic buffering agents, amino acid buffering agents, or combinations thereof, formulated in deuterated water.

In some instances, borates include boric acid, salts of boric acid, other pharmaceutically acceptable borates, and combinations thereof. In some cases, borates include boric acid, sodium borate, potassium borate, calcium borate, magnesium borate, manganese borate, and other such borate salts.

As used herein, the term polyol includes any compound having at least one hydroxyl group on each of two adjacent carbon atoms that are not in trans configuration relative to each other. In some cases, the polyols are linear or cyclic, substituted or unsubstituted, or mixtures thereof, so long as the resultant complex is water soluble and pharmaceutically acceptable. In some instances, examples of polyol include sugars, sugar alcohols, sugar acids and uronic acids. In some cases, polyols include, but are not limited to: mannitol, glycerin, xylitol and sorbitol.

In some embodiments, phosphate buffering agents include phosphoric acid; alkali metal phosphates such as disodium hydrogen phosphate, sodium dihydrogen phosphate, trisodium phosphate, dipotassium hydrogen phosphate, potassium dihydrogen phosphate, and tripotassium phosphate; alkaline earth metal phosphates such as calcium phosphate, calcium hydrogen phosphate, calcium dihydrogen phosphate, monomagnesium phosphate, dimagnesium phosphate (magnesium hydrogen phosphate), and trimagnesium phosphate; ammonium phosphates such as diammonium hydrogen phosphate and ammonium dihydrogen phosphate; or a combination thereof. In some instances, the phosphate buffering agent is an anhydride. In some instances, the phosphate buffering agent is a hydrate.

In some embodiments, borate-polyol complexes include those described in U.S. Pat. No. 6,503,497. In some instances, the borate-polyol complexes comprise borates in an amount of from about 0.01 to about 2.0% w/v, and one or more polyols in an amount of from about 0.01% to about 5.0% w/v.

In some cases, citrate buffering agents include citric acid and sodium citrate.

In some instances, acetate buffering agents include acetic acid, potassium acetate, and sodium acetate.

In some instances, carbonate buffering agents include sodium bicarbonate and sodium carbonate.

In some cases, organic buffering agents include Good's Buffer, such as for example 2-(N-morpholino)ethanesulfonic acid (MES), N-2-Acetamido)iminodiacetic acid, N-(Carbamoylmethyl)iminodiacetic acid (ADA), piperazine-N,N'-bis(2-ethanesulfonic acid (PIPES), N-(2-acetamido)-2-aminoethanesulfonic acid (ACES), β-Hydroxy-4-morpholinepropanesulfonic acid, 3-Morpholino-2-hydroxypropanesulfonic acid (MOPSO), cholamine chloride, 3-(N-morpholino)propansulfonic acid (MOPS), N,N-bis(2-hydroxyethyl)-2-aminoethanesulfonic acid (BES), 2-[(2-Hydroxy-1,1-bis(hydroxymethyl)ethyl)amino]ethanesulfonic acid (TES), 4-(2-hydroxyethyl)-1-piperazineethanesulfonic acid (HEPES), 3-(N, N-Bis[2-hydroxyethyl]amino)-2-hydroxypropanesulfonic acid (DIPSO), acetamidoglycine, 3-{[1,3-Dihydroxy-2-(hydroxymethyl)-2-propanyl]amino}-2-hydroxy-1-propanesulfonic acid (TAPSO), piperazine-1,4,-bis (2-hydroxypropanesulphonic acid) (POPSO), 4-(2-hydroxyethyl)piperazine-1-(2-hydroxypropanesulfonic acid) hydrate (HEPPSO), 3-[4-(2-hydroxyethyl)-1-piperazinyl]propanesulfonic acid (HEPPS), tricine, glycinamide, bicine or N-tris(hydroxymethyl)methyl-3-aminopropanesulfonic acid sodium (TAPS); glycine; and diethanolamine (DEA).

In some cases, amino acid buffering agents include taurine, aspartic acid and its salts (e.g., potassium salts, etc), E-aminocaproic acid, and the like.

In some instances, the composition described herein further comprises a tonicity adjusting agent. Tonicity adjusting agent is an agent introduced into a preparation such as an ophthalmic composition to reduce local irritation by preventing osmotic shock at the site of application. In some instances, buffer solution and/or a pD adjusting agent that broadly maintains the ophthalmic solution at a particular ion concentration and pD are considered as tonicity adjusting agents. In some cases, tonicity adjusting agents include various salts, such as halide salts of a monovalent cation. In some cases, tonicity adjusting agents include mannitol, sorbitol, dextrose, sucrose, urea, and glycerin. In some instances, suitable tonicity adjustors comprise sodium chloride, sodium nitrate, sodium sulfate, sodium bisulfate, potassium chloride, calcium chloride, magnesium chloride, zinc chloride, potassium acetate, sodium acetate, sodium bicarbonate, sodium carbonate, sodium thiosulfate, magnesium sulfate, disodium hydrogen phosphate, sodium dihydrogen phosphate, potassium dihydrogen phosphate, dextrose, mannitol, sorbitol, dextrose, sucrose, urea, propylene glycol, glycerin, or a combination thereof.

In some instances, the concentration of the tonicity adjusting agent in a composition described herein is between about 0.5% and about 2.0%. In some instances, the concentration of the tonicity adjusting agent in a composition described herein is between about 0.7% and about 1.8%, about 0.8% and about 1.5%, or about 1% and about 1.3%. In some instances, the concentration of the tonicity adjusting agent is about 0.6%, 0.7%, 0.8%, 0.9%, 1.0%, 1.1%, 1.2%, 1.3%, 1.4%, 1.5%, 1.6%, 1.7%, 1.8%, or 1.9%. In some cases, the percentage is a weight percentage.

In some cases, the composition described herein further comprises a pD adjusting agent. In some cases, the pD adjusting agent used is an acid or a base. In some embodiments, the base is oxides, hydroxides, carbonates, bicarbonates and the likes. In some cases, the oxides are metal oxides such as calcium oxide, magnesium oxide and the likes; hydroxides are of alkali metals and alkaline earth metals such as sodium hydroxide, potassium hydroxide, calcium hydroxide and the likes or their deuterated equivalents, and carbonates are sodium carbonate, sodium bicarbonates, potassium bicarbonates and the likes. In some cases, the acid is mineral acid and organic acids such as hydrochloric acid, nitric acid, phosphoric acid, acetic acid, citric acid, fumaric acid, malic acid tartaric acid and the likes or their deuterated equivalents. In some instances, the pD adjusting agent includes, but is not limited to, acetate, bicarbonate, ammonium chloride, citrate, phosphate, pharmaceutically acceptable salts thereof and combinations or mixtures thereof. In some embodiments, the pD adjusting agent comprises DCl and NaOD.

In some instances, the composition has a pD of between about 3 and about 9, about 4 and about 8, about 4.5 and about 7.8, about 5 and about 7.5, or about 5.5 and about 7. In some embodiments, the composition has a pD of less than about 8. In some embodiments, the composition has a pD of less than about 7.9. In some embodiments, the composition has a pD of less than about 7.8. In some embodiments, the composition has a pD of less than about 7.7. In some embodiments, the composition has a pD of less than about 7.6. In some embodiments, the composition has a pD of less than about 7.5. In some embodiments, the composition has a pD of less than about 7.4. In some embodiments, the composition has a pD of less than about 7.3. In some embodiments, the composition has a pD of less than about 7.2. In some embodiments, the composition has a pD of less than about 7.1. In some embodiments, the composition has a pD of less than about 7. In some embodiments, the composition has a pD of less than about 6.9. In some embodiments, the composition has a pD of less than about 6.8. In some embodiments, the composition has a pD of less than about 6.7. In some embodiments, the composition has a pD of less than about 6.6. In some embodiments, the composition has a pD of less than about 6.5. In some embodiments, the composition has a pD of less than about 6.4. In some embodiments, the composition has a pD of less than about 6.3. In some embodiments, the composition has a pD of less than about 6.2. In some embodiments, the composition has a pD of less than about 6.1. In some embodiments, the composition has a pD of less than about 6. In some embodiments, the composition has a pD of less than about 5.9. In some embodiments, the composition has a pD of less than about 5.8. In some embodiments, the composition has a pD of less than about 5.7. In some embodiments, the composition has a pD of less than about 5.6. In some embodiments, the composition has a pD of less than about 5.5. In some embodiments, the composition has a pD of less than about 5.4. In some embodiments, the composition has a pD of less than about 5.3. In some embodiments, the composition has a pD of less than about 5.2. In some embodiments, the composition has a pD of less than about 5.1. In some embodiments, the composition has a pD of less than about 5. In some embodiments, the composition has a pD of less than about 4.9. In some embodiments, the composition has a pD of less than about 4.8. In some embodiments, the composition has a pD of less than about 4.7. In some embodiments, the composition has a pD of less than about 4.6. In some embodiments, the composition has a pD of less than about 4.5. In some embodiments, the composition has a pD of less than about 4.4. In some embodiments, the composition has a pD of less than about 4.3. In some embodiments, the composition has a pD of less than about 4.2. In some embodiments, the composition has a pD of less than about 4.1. In some embodiments, the composition has a pD of less than about 4. In some embodiments, the composition has a pD of less than about 3.9. In some embodiments, the composition has a pD of less than about 3.8. In some embodiments, the composition has a pD of less than about 3.7. In some embodiments, the composition has a pD of less than about 3.6. In some embodiments, the composition has a pD of less than about 3.5. In some embodiments, the pD is the pD of the composition after extended period of time under storage condition.

In some instances, the composition has an initial pD of between about 3 and about 9, about 4 and about 8, about 4.5 and about 7.8, about 5 and about 7.5, or about 5.5 and about 7. In some embodiments, the composition has an initial pD of about 8. In some embodiments, the composition has an initial pD of about 7.9. In some embodiments, the composition has an initial pD of about 7.8. In some embodiments, the composition has an initial pD of about 7.7. In some embodiments, the composition has an initial pD of about 7.6. In some embodiments, the composition has an initial pD of about 7.5. In some embodiments, the composition has an initial pD of about 7.4. In some embodiments, the composition has an initial pD of about 7.3. In some embodiments, the composition has an initial pD of about 7.2. In some embodiments, the composition has an initial pD of about 7.1. In some embodiments, the composition has an initial pD of about 7. In some embodiments, the composition has an initial pD of about 6.9. In some embodiments, the composition has an initial pD of about 6.8. In some embodiments, the composition has an initial pD of about 6.7. In some embodiments, the composition has an initial pD of about 6.6. In some embodiments, the composition has an initial pD of about 6.5. In some embodiments, the composition has an initial pD of about 6.4. In some embodiments, the composition has an initial pD of about 6.3. In some embodiments, the composition has an initial pD of about 6.2. In some embodiments, the composition has an initial pD of about 6.1. In some embodiments, the composition has an initial pD of about 6. In some embodiments, the composition has an initial pD of about 5.9. In some embodiments, the composition has an initial pD of about 5.8. In some embodiments, the composition has an initial pD of about 5.7. In some embodiments, the composition has an initial pD of about 5.6. In some embodiments, the composition has an initial pD of about 5.5. In some embodiments, the composition has an initial pD of about 5.4. In some embodiments, the composition has an initial pD of about 5.3. In some embodiments, the composition has an initial pD of about 5.2. In some embod iments, the composition has an initial pD of about 5.1. In some embodiments, the composition has an initial pD of about 5. In some embodiments, the composition has an initial pD of about 4.9. In some embodiments, the composition has an initial pD of about 4.8. In some embodiments, the composition has an initial pD of about 4.7. In some embodiments, the composition has an initial pD of about 4.6. In some embodiments, the composition has an initial pD of about 4.5. In some embodiments, the composition has an initial pD of about 4.4. In some embodiments, the composition has an initial pD of about 4.3. In some embodiments, the composition has an initial pD of about 4.2. In some embodiments, the composition has an initial pD of about 4.1. In some embodiments, the composition has an initial pD of about 4. In some embodiments, the composition has an initial pD of about 3.9. In some embodiments, the composition has an initial pD of about 3.8. In some embodiments, the composition has an initial pD of about 3.7. In some embodiments, the composition has an initial pD of about 3.6. In some embodiments, the composition has an initial pD of about 3.5.

In some embodiments, the pD of the composition described herein is associated with the stability of the composition. In some embodiments, a stable composition comprises a pD of between about 3 and about 9, about 4 and about 8, about 4.5 and about 7.8, about 5 and about 7.5, or about 5.5 and about 7. In some embodiments, a stable composition comprises a pD of less than about 8. In some embodiments, a stable composition comprises a pD of less than about 7.9. In some embodiments, a stable composition comprises a pD of less than about 7.8. In some embodiments, a stable composition comprises a pD of less than about 7.7. In some embodiments, a stable composition comprises a pD of less than about 7.6. In some embodiments, a stable composition comprises a pD of less than about 7.5. In some embodiments, a stable composition comprises a pD of less than about 7.4. In some embodiments, a stable composition comprises a pD of less than about 7.3. In some embodiments, a stable composition comprises a pD of less than about 7.2. In some embodiments, a stable composition comprises a pD of less than about 7.1. In some embodiments, a stable composition comprises a pD of less than about 7. In some embodiments, a stable composition comprises a pD of less than about 6.9. In some embodiments, a stable composition comprises a pD of less than about 6.8. In some embodiments, a stable composition comprises a pD of less than about 6.7. In some embodiments, a stable composition comprises a pD of less than about 6.6. In some embodiments, a stable composition comprises a pD of less than about 6.5. In some embodiments, a stable composition comprises a pD of less than about 6.4. In some embodiments, a stable composition comprises a pD of less than about 6.3. In some embodiments, a stable composition comprises a pD of less than about 6.2. In some embodiments, a stable composition comprises a pD of less than about 6.1. In some embodiments, a stable composition comprises a pD of less than about 6. In some embodiments, a stable composition comprises a pD of less than about 5.9. In some embodiments, a stable composition comprises a pD of less than about 5.8. In some embodiments, a stable composition comprises a pD of less than about 5.7. In some embodiments, a stable composition comprises a pD of less than about 5.6. In some embodiments, a stable composition comprises a pD of less than about 5.5. In some embodiments, a stable composition comprises a pD of less than about 5.4. In some embodiments, a stable composition comprises a pD of less than about 5.3. In some embodiments, a stable composition comprises a pD of less than about 5.2. In some embodiments, a stable composition comprises a pD of less than about 5.1. In some embodiments, a stable composition comprises a pD of less than about 5. In some embodiments, a stable composition comprises a pD of less than about 4.9. In some embodiments, a stable composition comprises a pD of less than about 4.8. In some embodiments, a stable composition comprises a pD of less than about 4.7. In some embodiments, a stable composition comprises a pD of less than about 4.6. In some embodiments, a stable composition comp rises a pD of less than about 4.5. In some embodiments, a stable composition comprises a pD of less than about 4.4. In some embodiments, a stable composition comprises a pD of less than about 4.3. In some embodiments, a stable composition comprises a pD of less than about 4.2. In some embodiments, a stable composition comprises a pD of less than about 4.1. In some embodiments, a stable composition comprises a pD of less than about 4. In some embodiments, a stable composition comprises a pD of less than about 3.9. In some embodiments, a stable composition comprises a pD of less than about 3.8. In some embodiments, a stable composition comprises a pD of less than about 3.7. In some embodiments, a stable composition comprises a pD of less than about 3.6. In some embodiments, a stable composition comprises a pD of less than about 3.5.

As described elsewhere herein, in some instances, the $D_2O$ aqueous system stabilizes an ophthalmic composition. In some embodiments, this is due to a lower concentration of the reactive species (e.g., —OD) in the $D_2O$ aqueous system compared to the concentration of the reactive species (e.g., —OH) in an equivalent $H_2O$ aqueous system. In some instances, the concentration of the reactive species (e.g., —OD) in the $D_2O$ aqueous system is about one third less than the concentration of the reactive species (e.g., —OH) in the equivalent $H_2O$ aqueous system. In some cases, this is due to a lower or smaller dissociation constant of $D_2O$ than $H_2O$. For example, the $K_a(H_2O)$ is $1 \times 10^{-4}$, whereas the $K_a(D_2O)$ is $1 \times 10^{-1}$. As such, $D_2O$ is a weaker acid than $H_2O$. In some cases, base catalyzed hydrolysis leads to the presence of a degradant from the ophthalmic agent. In some cases, with a lower concentration of the reactive species that causes degradant formation, the ophthalmic solution is more stable in a $D_2O$ aqueous system than compared to an equivalent $H_2O$ aqueous system. In some embodiments, the ophthalmic composition formulated with deuterated water allows for a more stable ophthalmic composition relative to the ophthalmic composition formulated with $H_2O$.

In some embodiments, the presence of deuterated water shifts the pKa of the buffer. In some embodiments, the presence of deuterated water allows for the ophthalmic composition to simulate the stability of a lower pH system. In some instances, the buffer capacity of the ophthalmic composition is lowered, thereby allowing a faster shift in pH. In some instances, the lowered buffering capacity of the ophthalmic composition when administered into the eye allows the ophthalmic composition to reach physiological pH at a faster rate than compared to an ophthalmic composition formulated in $H_2O$. In some instances, the ophthalmic composition formulated with deuterated water allows for a lower tear production, or less tear reflex in the eye, in comparison with an ophthalmic composition formulated with $H_2O$.

In some instances, the composition described herein further comprises a disinfecting agent. In some cases, disinfecting agents include polymeric biguanides, polymeric quaternary ammonium compounds, chlorites, bisbiguanides, chlorite compounds (e.g. potassium chlorite, sodium chlorite, calcium chlorite, magnesium chlorite, or mixtures thereof), and a combination thereof.

In some instances, the composition described herein further comprises a preservative. In some cases, a preservative is added at a concentration to a composition described herein to prevent the growth of or to destroy a microorganism introduced into the composition. In some instances, microorganisms refer to bacteria (e.g. *Proteus mirabilis, Serratia marcescens*), virus (e.g. Herpes simplex virus, herpes zoster virus), fungus (e.g. fungi from the genus *Fusarium*), yeast (e.g. *Candida albicans*), parasites (e.g. Plasmodium spp., Gnathostoma spp.), protozoan (e.g. *Giardia* lamblia), nematodes (e.g. Onchocercus *volvulus*), worm (e.g. Dirofilaria *immitis*), and/or amoeba (e.g. Acanthamoeba).

In some instances, the concentration of the preservative is between about 0,0001% and about 1%, about 0.001% and about 0.8%, about 0.004% and about 0.5%, about 0.008% and about 0.1%, and about 0.01% and about 0.08%. In some cases, the concentration of the preservatives is about 0.001%, 0.002%, 0.003%, 0.004%, 0.005%, 0.006%, 0.008%, 0.009%, 0.009%, 0.01%, 0.015%, 0.02%, 0.025%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9% or 1.0%.

In some embodiments, the preservative is selected from benzalkonium chloride, cetrimonium, sodium perborate, stabilized oxy chloro complex, SofZia (Alcon), polyquaternium-1, chlorobutanol, edetate disodium, and polyhexamethylene biguanide.

In some embodiments, the composition described herein is stored in a plastic container. In some embodiments, the material of the plastic container comprises high density polyethylene (HDPE), low density polyethylene(LDPE), polyethylene terephthalate (PET), polyvinyl chloride (PVC), polyproylene (PP), polystyrene (PS), fluorine treated HDPE, post consumer resin (PCR), K-resine (SBC), or bioplastic. In some embodiments, the material of the plastic container comprises LDPE.

In some embodiments, the composition described herein is stored in a plastic container. In some embodiments, the composition stored in a plastic container has a pD of between about 3 and about 9, about 4 and about 8, about 4.5 and about 7.9, or about 4.9 and about 7.5. In some embodiments, the composition stored in a plastic container has a pD of less than about 8. In some embodiments, the composition stored in a plastic container has a pD of less than about 7.9. In some embodiments, the composition stored in a plastic container has a pD of less than about 7.8. In some embodiments, the composition stored in a plastic container has a pD of less than about 7.7. In some embodiments, the composition stored in a plastic container has a pD of less than about 7.6. In some embodiments, the composition stored in a plastic container has a pD of less than about 7.5. In some embodiments, the composition stored in a plastic container has a pD of less than about 7.4. In some embodiments, the composition stored in a plastic container has a pD of less than about 7.3. In some embodiments, the composition stored in a plastic container has a pD of less than about 7.2. In some embodiments, the composition stored in a plastic container has a pD of less than about 7.1. In some embodiments, the composition stored in a plastic container has a pD of less than about 7. In some embodiments, the composition stored in a plastic container has a pD of less than about 6.9. In some embodiments, the composition stored in a plastic container has a pD of less than about 6.8. In some embodiments, the composition stored in a plastic container has a pD of less than about 6.7. In some embodiments, the composition stored in a plastic container has a pD of less than about 6.6. In some embodiments, the composition stored in a plastic container has a pD of less than about 6.5. In some embodiments, the composition stored in a plastic container has a pD of less than about 6.4. In some embodiments, the composition stored in a plastic container has a pD of less than about 6.3. In some embodiments, the composition stored in a plastic container has a pD of less than about 6.2. In some embodiments, the composition stored in a plastic container has a pD of less than about 6.1. In some embodiments, the composition stored in a plastic container has a pD of less than about 6. In some embodiments, the composition stored in a plastic container has a pD of less than about 5.9. In some embodiments, the composition stored in a plastic container has a pD of less than about 5.8. In some embodiments, the composition stored in a plastic container has a pD of less than about 5.7. In some embodiments, the composition stored in a plastic container has a pD of less than about 5.6. In some embodiments, the composition stored in a plastic container has a pD of less than about 5.5. In some embodiments, the composition stored in a plastic container has a pD of less than about 5.4. In some embodiments, the composition stored in a plastic container has a pD of less than about 5.3. In some embodiments, the composition stored in a plastic container has a pD of less than about 5.2. In some embodiments, the composition stored in a plastic container has a pD of less than about 5.1. In some embodiments, the composition stored in a plastic container has a pD of less than about 5. In some embodiments, the composition stored in a plastic container has a pD of less than about 4.9. In some embodiments, the composition stored in a plastic container has a pD of less than about 4.8. In some embodiments, the composition stored in a plastic container has a pD of less than about 4.7. In some embodiments, the composition stored in a plastic container has a pD of less than about 4.6. In some embodiments, the composition stored in a plastic container has a pD of less than about 4.5. In some embodiments, the composition stored in a plastic container has a pD of less than about 4.4. In some embodiments, the composition stored in a plastic container has a pD of less than about 4.3. In some embodiments, the composition stored in a plastic container has a pD of less than about 4.2. In some embodiments, the composition stored in a plastic container has a pD of less than about 4.1. In some embodiments, the composition stored in a plastic container has a pD of less than about 4. In some embodiments, the composition stored in a plastic container has a pD of less than about 3.9. In some embodiments, the composition stored in a plastic container has a pD of less than about 3.8. In some embodiments, the composition stored in a plastic container has a pD of less than about 3.7. In some embodiments, the composition stored in a plastic container has a pD of less than about 3.6. In some embodiments, the composition stored in a plastic container has a pD of less than about 3.5.

In some embodiments, the composition stored in a plastic container has a potency of at least 80% after extended period of time under storage condition. In some embodiments, the composition stored in a plastic container has a potency of at least 85% after extended period of time under storage condition. In some embodiments, the composition stored in a plastic container has a potency of at least 90% after extended period of time under storage condition. In some embodiments, the composition stored in a plastic container has a potency of at least 93% after extended period of time under storage condition. In some embodiments, the composition stored in a plastic container has a potency of at least 95% after extended period of time under storage condition. In some embodiments, the composition stored in a plastic container has a potency of at least 97% after extended period of time under storage condition. In some embodiments, the composition stored in a plastic container has a potency of at least 98% after extended period of time under storage condition. In some embodiments, the composition stored in a plastic container has a potency of at least 99% after extended period of time under storage condition. In some instances, the storage condition comprises a temperature of about 2° C., 4° C., 8° C. 10° C., 15° C., 20° C., about 25° C., about 40° C., or about 60° C. In some instances, the extended period of time is at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, at least 24 months, at least 36 months, at least 3 years, at least 4 years, at least 5 years, or more.

In some embodiments, the composition stored in a plastic container has a potency of at least 80% at a temperature of about 25° C., about 40° C., or about 60° C. In some embodiments, the composition stored in a plastic container has a potency of at least 85% at a temperature of about 25° C., about 40° C., or about 60° C. In some embodiments, the composition stored in a plastic container has a potency of at least 90% at a temperature of about 25° C., about 40° C., or about 60° C. In some embodiments, the composition stored in a plastic container has a potency of at least 93% at a temperature of about 25° C., about 40° C., or about 60° C. In some embodiments, the composition stored in a plastic container has a potency of at least 95% at a temperature of about 25° C., about 40° C., or about 60° C. In some embodiments, the composition stored in a plastic container has a potency of at least 97% at a temperature of about 25° C., about 40° C., or about 60° C. In some embodiments, the composition stored in a plastic container has a potency of at least 98% at a temperature of about 25° C., about 40° C., or about 60° C. In some embodiments, the composition stored in a plastic container has a potency of at least 99% at a temperature of about 25° C. about 40° C., or about 60° C.

In some embodiments, the composition stored in a plastic container has a potency of at least 80% for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, at least 24 months, at least 36 months, at least 3 years, at least 4 years, at least 5 years, or more. In some embodiments, the composition stored in a plastic container has a potency of at least 85% for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, at least 24 months, at least 36 months, at least 3 years, at least 4 years, at least 5 years, or more. In some embodiments, the composition stored in a plastic container has a potency of at least 90% for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, at least 24 months, at least 36 months, at least 3 years, at least 4 years, at least 5 years, or more. In some embodiments, the composition stored in a plastic container has a potency of at least 93% for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, at least 24 months, at least 36 months, at least 3 years, at least 4 years, at least 5 years, or more. In some embodiments, the composition stored in a plastic container has a potency of at least 95% for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, at least 24 months, at least 36 months, at least 3 years, at least 4 years, at least 5 years, or more. In some embodiments, the composition stored in a plastic container has a potency of at least 97% for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, at least 24 months, at least 36 months, at least 3 years, at least 4 years, at least 5 years, or more. In some embodiments, the composition stored in a plastic container has a potency of at least 98% for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, at least 24 months, at least 36 months, at least 3 years, at least 4 years, at least 5 years, or more. In some embodiments, the composition stored in a plastic container has a potency of at least 99% for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, at least 24 months, at least 36 months, at least 3 years, at least 4 years, at least 5 years, or more.

In some embodiments, the composition stored in a plastic container comprises less than 20% of primary degradant based on the concentration of the ophthalmic agent after extended period of time under storage condition. In some embodiments, the composition stored in a plastic container comprises less than 15% of primary degradant based on the concentration of the ophthalmic agent after extended period of time under storage condition. In some embodiments, the composition stored in a plastic container comprises less than 10% of primary degradant based on the concentration of the ophthalmic agent after extended period of time under storage condition. In some embodiments, the composition stored in a plastic container comprises less than 5% of primary degradant based on the concentration of the ophthalmic agent after extended period of time under storage condition.

In some embodiments, the composition stored in a plastic container comprises fromless than 2.5% of primary degradant to less than 0.1% of primary degradant based on the concentration of the ophthalmic agent after extended period of time under storage condition. In some embodiments, the composition stored in a plastic container comprises less than 2.5% of primary degradant based on the concentration of the ophthalmic agent after extended period of time under storage condition. In some embodiments, the composition stored in a plastic container comprises less than 2.0% of primary degradant based on the concentration of the ophthalmic agent after extended period of time under storage condition. In some embodiments, the composition stored in a plastic container comprises less than 1.5% of primary degradant based on the concentration of the ophthalmic agent after extended period of time under storage condition. In some embodiments, the composition stored in a plastic container comprises less than 1.0% of primary degradant based on the concentration of the ophthalmic agent after extended period of time under storage condition. In some embodiments, the composition stored in a plastic container comprises less than 0.5% of primary degradant based on the concentration of the ophthalmic agent after extended period of time under storage condition. In some embodiments, the composition stored in a plastic container comprises less than 0.4% of primary degradant based on the concentration of the ophthalmic agent after extended period of time under storage condition. In some embodiments, the composition stored in a plastic container comprises less than 0.3% of primary degradant based on the concentration of the ophthalmic agent after extended period of time under storage condition. In some embodiments, the composition stored in a plastic container comprises less than 0.2% of primary degradant based on the concentration of the ophthalmic agent after extended period of time under storage condition. In some embodiments, the composition stored in a plastic container comprises less than 0.1% of primary degradant based on the concentration of the ophthalmic agent after extended period of time under storage condition. In some instances, the storage condition comprises a temperature of about 25° C., about 40° C., or about 60° C. In some instances, the extended period of time is at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, at least 24 months, at least 36 months, at least 3 years, at least 4 years, at least 5 years, or more.

In some embodiments, the composition stored in a plastic container comprises less than 20% of primary degradant based on the concentration of the ophthalmic agent at a temperature of about 25° C., about 40° C., or about 60° C. In some embodiments, the composition stored in a plastic container comprises less than 15% of primary degradant based on the concentration of the ophthalmic agent at a temperature of about 25° C., about 40° C., or about 60° C. In some embodiments, the composition stored in a plastic container comprises less than 10% of primary degradant based on the concentration of the ophthalmic agent at a temperature of about 25° C. about 40° C., or about 60° C. In some embodiments, the composition stored in a plastic container comprises less than 5% of primary degradant based on the concentration of the ophthalmic agent at a temperature of about 25° C., about 40° C., or about 60° C.

In some embodiments, the composition stored in a plastic container comprises from less than 2.5% of primary degradant to less than 0.1% of primary degradant based on the concentration of the ophthalmic agent at a temperature of about 25° C., about 40°, or about 60° C. In some embodiments, the composition stored in a plastic container comprises less than 2.5% of primary degradant based on the concentration of the ophthalmic agent at a temperature of about 25° C., about 40° C., or about 60° C. In some embodiments, the composition stored in a plastic container comprises less than 2.0% of primary degradant based on the concentration of the ophthalmic agent at a temperature of about 25° C., about 40° C., or about 60° C. In some embodiments, the composition stored in a plastic container comprises less than 1.5% of primary degradant based on the concentration of the ophthalmic agent at a temperature of about 25° C., about 40° C., or about 60° C. In some embodiments, the composition stored in a plastic container comprises less than 1.0% of primary degradant based on the concentration of the ophthalmic agent at a temperature of about 25° C., about 40° C., or about 60° C. In some embodiments, the composition stored in a plastic container comprises less than 0.5% of primary degradant based on the concentration of the ophthalmic agent at a temperature of about 25° C., about 40° C., or about 60° C. In some embodiments, the composition stored in a plastic container comprises less than 0.4% of primary degradant based on the concentration of the ophthalmic agent at a temperature of about 25° C., about 40° C., or about 60° C. In some embodiments, the composition stored in a plastic container comprises less than 0.3% of primary degradant based on the concentration of the ophthalmic agent at a temperature of about 25° C., about 40° C., or about 60° C. In some embodiments, the composition stored in a plastic container comprises less than 0.2% of primary degradant based on the concentration of the ophthalmic agent at a temperature of about 25° C., about 40° C., or about 60° C. In some embodiments, the composition stored in a plastic container comprises less than 0.1% of primary degradant based on the concentration of the ophthalmic agent at a temperature of about 25° C., about 40° C., or about 60° C.

In some embodiments, the composition stored in a plastic container comprises less than 20% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container comprises less than 15% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container comprises less than 10% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container comprises less than 5% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months.

In some embodiments, the composition stored in a plastic container comprises from less than 2.5% of primary degradant to less than 0.1% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container comprises less than 2.5% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container comprises less than 2.0% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container comprises less than 1.5% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container comprises less than 1.0% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container comprises less than 0.5% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container comprises less than 0.4% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container comprises less than 0.3% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container comprises less than 0.2% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container comprises less than 0.1% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months.

In some embodiments, the composition described herein is stored in a glass container. In some embodiments, the glass container is a glass vial, such as for example, a type I, type II or type III glass vial. In some embodiments, the glass container is a type I glass vial. In some embodiments, the type I glass vial is a borosilicate glass vial.

In some embodiments, the composition stored in a glass container has a pD of higher than about 7. In some embodiments, the composition stored in a glass container has a pD of higher than about 7.5. In some embodiments, the composition stored in a glass container has a pD of higher than about 8. In some embodiments, the composition stored in a glass container has a pD of higher than about 8.5. In some embodiments, the composition stored in a glass container has a pD of higher than about 9.

In some embodiments, the composition stored in a glass container has a potency of less than 60% at a temperature of about 25° C., about 40° C., or about 60° C. In some embodiments, the composition stored in a glass container has a potency of less than 60% for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, at least 24 months, at least 36 months, at least 3 years, at least 4 years, at least 5 years, or more.

In some embodiments, the composition stored in a glass container is less stable than a composition stored in a plastic container.

In some embodiments, the composition is stored under in the dark. In some instances, the composition is stored in the presence of light. In some instances, the light is indoor light, room light, or sun light. In some instances, the composition is stable while stored in the presence of light.

In some embodiments, the composition described herein is formulated as an aqueous solution. In some embodiments, the aqueous solution is a stable aqueous solution. In some instances, the aqueous solution is stored in a plastic container as described above. In some instances, the aqueous solution is not stored in a glass container. In some instances, the aqueous solution is stored in the dark. In some instances, the aqueous solution is stored in the presence of light. In some instances, the aqueous solution is stable in the presence of light.

In a specific embodiment, the ophthalmically acceptable formulations alternatively comprise a cyclodextrin. Cyclodextrins are cyclic oligosaccharides containing 6, 7, or 8 glucopyranose units, referred to as α-cyclodextrin, β-cyclodextrin, or γ-cyclodextrin respectively. Cyclodextrins have a hydrophilic exterior, which enhances water-soluble, and a hydrophobic interior which forms a cavity. In an aqueous environment, hydrophobic portions of other molecules often enter the hydrophobic cavity of cyclodextrin to form inclusion compounds. Additionally, cyclodextrins are also capable of other types of nonbonding interactions with molecules that are not inside the hydrophobic cavity. Cyclodextrins have three free hydroxyl groups for each glucopyranose unit, or 18 hydroxyl groups on α-cyclodextrin, 21 hydroxyl groups on β-cyclodextrin, and 24 hydroxyl groups on γ-cyclodextrin. In some cases, one or more of these hydroxyl groups are reacted with any of a number of reagents to form a large variety of cyclodextrin derivatives, including hydroxypropyl ethers, sulfonates, and sulfoalkylethers. Shown below is the structure of β-cyclodextrin and the hydroxypropyl-β-cyclodextrin (HPβCD).

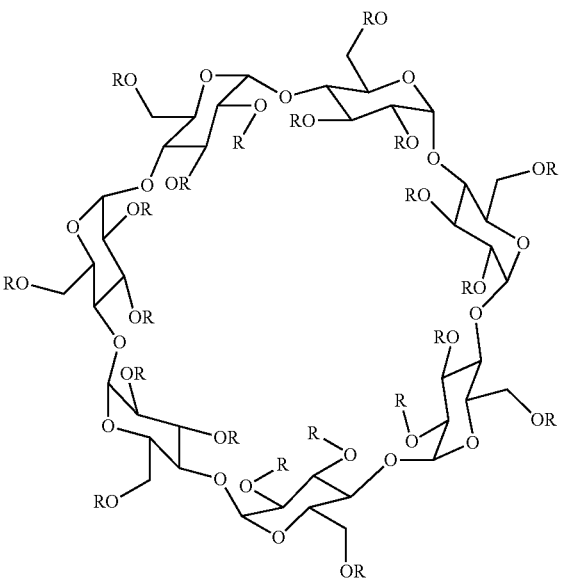

R = H
β-cyclodextrin

R = CH$_2$CH(OH)CH$_3$
hydroxypropyl β-cyclodextrin

In some embodiments, the use of cyclodextrins in the pharmaceutical compositions described herein improves the solubility of the drug. Inclusion compounds are involved in many cases of enhanced solubility; however other interactions between cyclodextrins and insoluble compounds also improves solubility. Hydroxypropyl-β-cyclodextrin (HPβCD) is commercially available as a pyrogen free product. It is a nonhygroscopic white powder that readily dissolves in water. HPβCD is thermally stable and does not degrade at neutral pH. Thus, cyclodextrins improve the solubility of a therapeutic agent in a composition or formulation. Accordingly, in some embodiments, cyclodextrins are included to increase the solubility of the ophthalmically acceptable ophthalmic agents within the formulations described herein. In other embodiments, cyclodextrins in addition serve as controlled release excipients within the formulations described herein.

By way of example only, cyclodextrin derivatives for use include α-cyclodextrin. β-cyclodextrin, γ-cyclodextrin, hydroxyethyl-β-cyclodextrin, hydroxypropyl-γ-cyclodextrin, sulfated β-cyclodextrin, sulfated α-cyclodextrin, sulfobutyl ether β-cyclodextrin.

The concentration of the cyclodextrin used in the compositions and methods disclosed herein varies according to the physiochemical properties, pharmacokinetic properties, side effect or adverse events, formulation considerations, or other factors associated with the therapeutically ophthalmic agent, or a salt or prodrug thereof, or with the properties of other excipients in the composition. Thus, in certain circumstances, the concentration or amount of cyclodextrin used in accordance with the compositions and methods disclosed herein will vary, depending on the need. When used, the amount of cyclodextrins needed to increase solubility of the ophthalmic agent and/or function as a controlled release excipient in any of the formulations described herein is selected using the principles, examples, and teachings described herein.

Other stabilizers that are useful in the ophthalmically acceptable formulations disclosed herein include, for example, fatty acids, fatty alcohols, alcohols, long chain fatty acid esters, long chain ethers, hydrophilic derivatives of fatty acids, polyvinyl pyrrolidones, polyvinyl ethers, polyvinyl alcohols, hydrocarbons, hydrophobic polymers, moisture-absorbing polymers, and combinations thereof. In some embodiments, amide analogues of stabilizers are also used. In further embodiments, the chosen stabilizer changes the hydrophobicity of the formulation, improves the mixing of various components in the formulation, controls the moisture level in the formula, or controls the mobility of the phase.

In other embodiments, stabilizers are present in sufficient amounts to inhibit the degradation of the ophthalmic agent. Examples of such stabilizing agents, include, but are not limited to: glycerol, methionine, monothioglycerol, EDTA, ascorbic acid, polysorbate 80, polysorbate 20, arginine, heparin, dextran sulfate, cyclodextrins, pentosan polysulfate and other heparinoids, divalent cations such as magnesium and zinc, or combinations thereof.

Additional useful stabilization agents for ophthalmically acceptable formulations include one or more anti-aggregation additives to enhance stability of ophthalmic formulations by reducing the rate of protein aggregation. The anti-aggregation additive selected depends upon the nature of the conditions to which the ophthalmic agents are exposed. For example, certain formulations undergoing agitation and thermal stress require a different anti-aggregation additive than a formulation undergoing lyophilization and reconstitution. Useful anti-aggregation additives include, by way of example only, urea, guanidinium chloride, simple amino acids such as glycine or arginine, sugars, polyalcohols, polysorbates, polymers such as polyethylene gly col and dextrans, alkyl saccharides, such as alkyl glycoside, and surfactants.

Other useful formulations optionally include one or more ophthalmically acceptable antioxidants to enhance chemical stability where required. Suitable antioxidants include, by way of example only, ascorbic acid, methionine, sodium thiosulfate and sodium metabisulfite. In one embodiment, antioxidants are selected from metal chelating agents, thiol containing compounds and other general stabilizing agents.

Still other useful compositions include one or more ophthalmically acceptable surfactants to enhance physical stability or for other purposes. Suitable nonionic surfactants include, but are not limited to, polyoxyethylene fatty acid glycerides and vegetable oils, e.g., polyoxyethylene (60) hydrogenated castor oil, and polyoxyethylene alkylethers and alkylphenyl ethers, e.g., octoxynol 10, octoxynol 40.

In some embodiments, the ophthalmically acceptable pharmaceutical formulations described herein are stable with respect to compound degradation (e.g. less than 30% degradation, less than 25% degradation, less than 20% degradation, less than 15% degradation, less than 10% degradation, less than 8% degradation, less than 5% degradation, less than 3% degradation, less than 2% degradation, or less than 5% degradation) over a period of any of at least about 1 day, at least about 2 days, at least about 3 days, at least about 4 day s, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 3 months, at least about 4 months, at least about 5 months, at least about 6 months, at least about 12 months, at least about 18 months, at least about 24 months, at least about 36 months, at least about 3 years, at least about 4 years, at least about 5 years, or at least about 10 years under storage conditions (e.g. room temperature). In other embodiments, the formulations described herein are stable with respect to compound degradation over a period of at least about 1 week. Also described herein are formulations that are stable with respect to compound degradation over a period of at least about 1 month.

In other embodiments, an additional surfactant (co-surfactant) and/or buffering agent is combined with one or more of the pharmaceutically acceptable vehicles previously described herein so that the surfactant and/or buffering agent maintains the product at an optimal pD for stability. Suitable co-surfactants include, but are not limited to: a) natural and synthetic lipophilic agents, e.g., phospholipids, cholesterol, and cholesterol fatty acid esters and derivatives thereof; b) nonionic surfactants, which include for example, polyoxyethylene fatty alcohol esters, sorbitan fatty acid esters (Spans), polyoxyethylene sorbitan fatty acid esters (e.g., polyoxyethylene (20)sorbitan monooleate (Tween 80), polyoxyethylene(20)sorbitan monostearate (Tween 60), polyoxyethylene (20) sorbitan monolaurate (Tween 20) and other Tweens, sorbitan esters, glycerol esters, e.g., Myrj and glycerol triacetate (triacetin), polyethylene glycols, cetyl alcohol, cetostearyl alcohol, stearyl alcohol, polysorbate 80, poloxamers, poloxamines, polyoxyethylene castor oil derivatives (e.g., Cremophor® RH40, Cremphor A25, Cremphor A20, Cremophor® EL) and other Cremophors, sulfosuccinates, alkyl sulphates (SLS); PEG glyceryl fatty acid esters such as PEG-8 glyceryl caprylate/caprate (Labrasol), PEG-4 glyceryl caprylate/caprate (Labrafac Hydro WL 1219), PEG-32 glyceryl laurate (Gelucire 444/14), PEG-6 glyceryl mono oleate (Labrafil M 1944 CS), PEG-6 glyceryl linoleate (Labrafil M 2125 CS); propylene glycol mono- and di-fatty acid esters, such as propylene glycol laurate, propylene glycol caprylate/caprate; Brij® 700, ascorbyl-6-palmitate, stearylamine, sodium lauryl sulfate, polyoxethylenegly cerol triiricinoleate, and any combinations or mixtures thereof; c) anionic surfactants include, but are not limited to, calcium carboxymethylcellulose, sodium carboxymethylcellulose, sodium sulfosuccinate, dioctyl, sodium alginate, alkyl poly oxy ethylene sulfates, sodium lauryl sulfate, triethanolamine stearate, potassium laurate, bile salts, and any combinations or mixtures thereof; and d) cationic surfactants such as cetyltrimethylammonium bromide, and lauryldimethylbenzyl-ammonium chloride.

In a further embodiment, when one or more co-surfactants are utilized in the ophthalmically acceptable formulations of the present disclosure, they are combined, e.g., with a pharmaceutically acceptable vehicle and is present in the final formulation, e.g., in an amount ranging from about 0.1% to about 20%, from about 0.5% to about 10%.

In one embodiment, the surfactant has an HLB value of 0 to 20. In additional embodiments, the surfactant has an HLB value of 0 to 3, of 4 to 6, of 7 to 9, of 8 to 18, of 13 to 15, of 10 to 18.

pD

In some embodiments, the pD of a composition described herein is adjusted (e.g., by use of a buffer and/or a pD adjusting agent) to an ophthalmically compatible pD range of from about 3 and about 9, about 4 to about 8, about 4.5 to about 7.5, or about 5 to about 7. In some embodiments, the ophthalmic composition has a pD of from about 5.0 to about 7.0. In some embodiments, the ophthalmic composition has a pD of from about 5.5 to about 7.0. In some embodiments, the ophthalmic composition has a pD of from about 6.0 to about 7.0.

In some embodiments, useful formulations include one or more pD adjusting agents or buffering agents. Suitable pD adjusting agents or buffers include, but are not limited to acetate, bicarbonate, ammonium chloride, citrate, phosphate, deuterated forms of acetate, bicarbonate, ammonium chloride, citrate, phosphate, pharmaceutically acceptable salts thereof and combinations or mixtures thereof. In some embodiments, the pD adjusting agents or buffers include deuterated hydrochloric acid (DCl), deuterated sodium hydroxide (NaOD), deuterated acetic acid (CD$_3$COOD), or deuterated citric acid (C$_6$D$_8$O$_7$).

In one embodiment, when one or more buffers are utilized in the formulations of the present disclosure, they are combined, e.g., with a pharmaceutically acceptable vehicle and are present in the final formulation, e.g., in an amount ranging from about 0.1% to about 20%, from about 0.5% to about 10%. In certain embodiments of the present disclosure, the amount of buffer included in the gel formulations are an amount such that the pD of the gel formulation does not interfere with the body's natural buffering system.

In one embodiment, diluents are also used to stabilize compounds because they provide a more stable environment. Salts dissolved in buffered solutions (which also provide pD control or maintenance) are utilized as diluents in the art, including, but not limited to a phosphate buffered saline solution.

In some embodiments, the pD is calculated according to the formula disclosed in Glasoe et al., "Use of glass electrodes to measure acidities in deuterium oxide," J. Physical Chem. 64(1): 188-190 (1960). In some embodiment, the pD is calculated as pD=pH*+0.4, in which pH* is the measured or observed pH of the ophthalmic composition formulated in a solution comprising deuterated water (e.g., D$_2$O).

In some embodiments, the ophthalmic aqueous, gel, or ointment composition described herein has a pD of between about 3 and about 9, about 4 and about 8, between about 4.5 and about 8, between about 4.9 and about 7.9, between about 5.4 and about 7.9, between about 5.9 and about 7.9, between about 6.4 and about 7.9, or between about 7.4 and about 7.9. In some embodiments, the ophthalmic aqueous, gel, or ointment composition described herein has a pD of between about 4.5-7.5, between about 5.0 and about 7.5, between about 5.5 and about 7.5, between about 6.0 and about 7.5, or between about 7.0 and about 7.5. In some embodiments, the ophthalmic aqueous, gel, or ointment composition described herein has a pD of between about 4.5-7.0, between about 5.0 and about 7.0, between about 5.5 and about 7.0, between about 6.0 and about 7.0, or between about 6.5 and about 7.0. In some embodiments, the ophthalmic aqueous, gel, or ointment composition described herein has a pD of between about 4.9-7.4, between about 5.4 and about 7.4, between about 5.9 and about 7.4, between about 6.4 and about 7.4, or between about 6.9 and about 7.4. In some embodiments, the ophthalmic aqueous, gel, or ointment composition described herein has a pD of between about 4.5-6.5, between about 5.0 and about 6.5, between about 5.5 and about 6.5, or between about 6.0 and about 6.5. In some embodiments, the ophthalmic aqueous, gel, or ointment composition described herein has a pD of between about 4.9-6.9, between about 5.4 and about 6.9, between about 5.9 and about 6.9, or between about 6.4 and about 6.9. In some embodiments, the ophthalmic aqueous, gel, or ointment composition described herein has a pD of between about 4.5-6.0, between about 5.0 and about 6.0, or between about 5.5 and about 6.0. In some embodiments, the ophthalmic aqueous, gel, or ointment composition described herein has a pD of between about 4.9-6.4, between about 5.4 and about 6.4, or between about 5.9 and about 6.4. In some embodiments, the ophthalmic aqueous, gel, or ointment composition described herein has a pD of between about 4.5-5.5, or between about 5.0 and about 5.5. In some embodiments, the ophthalmic aqueous, gel, or ointment composition described herein has a pD of between about 4.9-5.9, or between about 5.4 and about 5.9. In some embodiments, the ophthalmic aqueous, gel, or ointment composition described herein has a pD of between about 4.5-5.0. In some embodiments, the ophthalmic aqueous, gel, or ointment composition described herein has a pD of between about 4.9-5.4.

In some embodiments, the ophthalmic composition is an ophthalmic aqueous composition. In some instances, the ophthalmic aqueous composition has a pD of between about 3 and about 9, about 4 and about 8, about 4.5 and about 7.8, about 5 and about 7.5, or about 5.5 and about 7. In some embodiments, the ophthalmic aqueous composition has a pD of about 8. In some embodiments, the ophthalmic aqueous composition has a pD of about 7.9. In some embodiments, the ophthalmic aqueous composition has a pD of about 7.8. In some embodiments, the ophthalmic aqueous composition has a pD of about 7.7. In some embodiments, the ophthalmic aqueous composition has a pD of about 7.6. In some embodiments, the ophthalmic aqueous composition has a pD of about 7.5. In some embodiments, the ophthalmic aqueous composition has a pD of about 7.4. In some embodiments, the ophthalmic aqueous composition has a pD of about 7.3. In some embodiments, the ophthalmic aqueous composition has a pD of about 7.2. In some embodiments, the ophthalmic aqueous composition has a pD of about 7.1. In some embodiments, the ophthalmic aqueous composition has a pD of about 7. In some embodiments, the ophthalmic aqueous composition has a pD of about 6.9. In some embodiments, the ophthalmic aqueous composition has a pD of about 6.8. In some embodiments, the ophthalmic aqueous composition has a pD of about 6.7. In some embodiments, the ophthalmic aqueous composition has a pD of about 6.6. In some embodiments, the ophthalmic aqueous composition has a pD of about 6.5. In some embodiments, the ophthalmic aqueous composition has a pD of about 6.4. In some embodiments, the ophthalmic aqueous composition has a pD of about 6.3. In some embodiments, the ophthalmic aqueous composition has a pD of about 6.2. In some embodiments, the ophthalmic aqueous composition has a pD of about 6.1. In some embodiments, the ophthalmic aqueous composition has a pD of about 6. In some embodiments, the ophthalmic aqueous composition has a pD of about 5.9. In some embodiments, the ophthalmic aqueous composition has a pD of about 5.8. In some embodiments, the ophthalmic aqueous composition has a pD of about 5.7. In some embodiments, the ophthalmic aqueous composition has a pD of about 5.6. In some embodiments, the ophthalmic aqueous composition has a pD of about 5.5. In some embodiments, the ophthalmic aqueous composition has a pD of about 5.4. In some embodiments, the ophthalmic aqueous composition has a pD of about 5.3. In some embodiments, the ophthalmic aqueous composition has a pD of about 5.2. In some embodiments, the ophthalmic aqueous composition has a pD of about 5.1. In some embodiments, the ophthalmic aqueous composition has a pD of about 5. In some embodiments, the ophthalmic aqueous composition has a pD of about 4.9. In some embodiments, the ophthalmic aqueous composition has a pD of about 4.8. In some embodiments, the ophthalmic aqueous composition has a pD of about 4.7. In some embodiments, the ophthalmic aqueous composition has a pD of about 4.6. In some embodiments, the ophthalmic aqueous composition has a pD of about 4.5. In some embodiments, the ophthalmic aqueous composition has a pD of about 4.4. In some embodiments, the ophthalmic aqueous composition has a pD of about 4.3. In some embodiments, the ophthalmic aqueous composition has a pD of about 4.2. In some embodiments, the ophthalmic aqueous composition has a pD of about 4.1. In some embodiments, the ophthalmic aqueous composition has a pD of about 4. In some embodiments, the ophthalmic aqueous composition has a pD of about 3.9. In some embodiments, the ophthalmic aqueous composition has a pD of about 3.8. In some embodiments, the ophthalmic aqueous composition has a pD of about 3.7. In some embodiments, the ophthalmic aqueous composition has a pD of about 3.6. In some embodiments, the ophthalmic aqueous composition has a pD of about 3.5. In some embodiments, the pD is an initial pD of the ophthalmic aqueous composition. In some embodiments, the pD is the pD of the ophthalmic aqueous composition after extended period of time under storage condition.

In some instances, the ophthalmic aqueous composition has an initial pD of between about 3 and about 9, about 4 and about 8, about 4.5 and about 7.8, about 5 and about 7.5, or about 5.5 and about 7. In some embodiments, the ophthalmic aqueous composition has an initial pD of about 8. In some embodiments, the ophthalmic aqueous composition has an initial pD of about 7.9. In some embodiments, the ophthalmic aqueous composition has an initial pD of about 7.8. In some embodiments, the ophthalmic aqueous composition has an initial pD of about 7.7. In some embodiments, the ophthalmic aqueous composition has an initial pD of about 7.6. In some embodiments, the ophthalmic aqueous composition has an initial pD of about 7.5. In some embodiments, the ophthalmic aqueous composition has an initial pD of about 7.4. In some embodiments, the ophthalmic aqueous composition has an initial pD of about 7.3. In some embodiments, the ophthalmic aqueous composition has an initial pD of about 7.2. In some embodiments, the ophthalmic aqueous composition has an initial pD of about 7.1. In some embodiments, the ophthalmic aqueous composition has an initial pD of about 7. In some embodiments, the ophthalmic aqueous composition has an initial pD of about 6.9. In some embodiments, the ophthalmic aqueous composition has an initial pD of about 6.8. In some embodiments, the ophthalmic aqueous composition has an initial pD of about 6.7. In some embodiments, the ophthalmic aqueous composition has an initial pD of about 6.6. In some embodiments, the ophthalmic aqueous composition has an initial pD of about 6.5. In some embodiments, the ophthalmic aqueous composition has an initial pD of about 6.4. In some embodiments, the ophthalmic aqueous composition has an initial pD of about 6.3. In some embodiments, the ophthalmic aqueous composition has an initial pD of about 6.2. In some embodiments, the ophthalmic aqueous composition has an initial pD of about 6.1. In some embodiments, the ophthalmic aqueous composition has an initial pD of about 6. In some embodiments, the ophthalmic aqueous composition has an initial pD of about 5.9. In some embodiments, the ophthalmic aqueous composition has an initial pD of about 5.8. In some embodiments, the ophthalmic aqueous composition has an initial pD of about 5.7. In some embodiments, the ophthalmic aqueous composition has an initial pD of about 5.6. In some embodiments, the ophthalmic aqueous composition has an initial pD of about 5.5. In some embodiments, the ophthalmic aqueous composition has an initial pD of about 5.4. In some embodiments, the ophthalmic aqueous composition has an initial pD of about 5.3. In some embodiments, the ophthalmic aqueous composition has an initial pD of about 5.2. In some embodiments, the ophthalmic aqueous composition has an initial pD of about 5.1. In some embodiments, the ophthalmic aqueous composition has an initial pD of about 5. In some embodiments, the ophthalmic aqueous composition has an initial pD of about 4.9. In some embodiments, the ophthalmic aqueous composition has an initial pD of about 4.8. In some embodiments, the ophthalmic aqueous composition has an initial pD of about 4.7. In some embodiments, the ophthalmic aqueous composition has an initial pD of about 4.6. In some embodiments, the ophthalmic aqueous composition has an initial pD of about 4.5. In some embodiments, the ophthalmic aqueous composition has an initial pD of about 4.4. In some embodiments, the ophthalmic aqueous composition has an initial pD of about 4.3. In some embodiments, the ophthalmic aqueous composition has an initial pD of about 4.2. In some embodiments, the ophthalmic aqueous composition has an initial pD of about 4.1. In some embodiments, the ophthalmic aqueous composition has an initial pD of about 4. In some embodiments, the ophthalmic aqueous composition has an initial pD of about 3.9. In some embodiments, the ophthalmic aqueous composition has an initial pD of about 3.8. In some embodiments, the ophthalmic aqueous composition has an initial pD of about 3.7. In some embodiments, the ophthalmic aqueous composition has an initial pD of about 3.6. In some embodiments, the ophthalmic aqueous composition has an initial pD of about 3.5.

In some instances, the ophthalmic aqueous composition has a pD of between about 3 and about 9, about 4 and about 8, about 4.5 and about 7.8, about 5 and about 7.5, or about 5.5 and about 7. In some embodiments, the ophthalmic aqueous composition has a pD of less than about 8. In some embodiments, the ophthalmic aqueous composition has a pD of less than about 7.9. In some embodiments, the ophthalmic aqueous composition has a pD of less than about 7.8. In some embodiments, the ophthalmic aqueous composition has a pD of less than about 7.7. In some embodiments, the ophthalmic aqueous composition has a pD of less than about 7.6. In some embodiments, the ophthalmic aqueous composition has a pD of less than about 7.5. In some embodiments, the ophthalmic aqueous composition has a pD of less than about 7.4. In some embodiments, the ophthalmic aqueous composition has a pD of less than about 7.3. In some embodiments, the ophthalmic aqueous composition has a pD of less than about 7.2. In some embodiments, the ophthalmic aqueous composition has a pD of less than about 7.1. In some embodiments, the ophthalmic aqueous composition has a pD of less than about 7. In some embodiments, the ophthalmic aqueous composition has a pD of less than about 6.9. In some embodiments, the ophthalmic aqueous composition has a pD of less than about 6.8. In some embodiments, the ophthalmic aqueous composition has a pD of less than about 6.7. In some embodiments, the ophthalmic aqueous composition has a pD of less than about 6.6. In some embodiments, the ophthalmic aqueous composition has a pD of less than about 6.5. In some embodiments, the ophthalmic aqueous composition has a pD of less than about 6.4. In some embodiments, the ophthalmic aqueous composition has a pD of less than about 6.3. In some embodiments, the ophthalmic aqueous composition has a pD of less than about 6.2. In some embodiments, the ophthalmic aqueous composition has a pD of less than about 6.1. In some embodiments, the ophthalmic aqueous composition has a pD of less than about 6. In some embodiments, the ophthalmic aqueous composition has a pD of less than about 5.9. In some embodiments, the ophthalmic aqueous composition has a pD of less than about 5.8. In some embodiments, the ophthalmic aqueous composition has a pD of less than about 5.7. In some embodiments, the ophthalmic aqueous composition has a pD of less than about 5.6. In some embodiments, the ophthalmic aqueous composition has a pD of less than about 5.5. In some embodiments, the ophthalmic aqueous composition has a pD of less than about 5.4. In some embodiments, the ophthalmic aqueous composition has a pD of less than about 5.3. In some embodiments, the ophthalmic aqueous composition has a pD of less than about 5.2. In some embodiments, the ophthalmic aqueous composition has a pD of less than about 5.1. In some embodiments, the ophthalmic aqueous composition has a pD of less than about 5. In some embodiments, the ophthalmic aqueous composition has a pD of less than about 4.9. In some embodiments, the ophthalmic aqueous composition has a pD of less than about 4.8. In some embodiments, the ophthalmic aqueous composition has a pD of less than about 4.7. In some embodiments, the ophthalmic aqueous composition has a pD of less than about 4.6. In some embodiments, the ophthalmic aqueous composition has a pD of less than about 4.5. In some embodiments, the ophthalmic aqueous composition has a pD of less than about 4.4. In some embodiments, the ophthalmic aqueous composition has a pD of less than about 4.3. In some embodiments, the ophthalmic aqueous composition has a pD of less than about 4.2. In some embodiments, the ophthalmic aqueous composition has a pD of less than about 4.1. In some embodiments, the ophthalmic aqueous composition has a pD of less than about 4. In some embodiments, the ophthalmic aqueous composition has a pD of less than about 3.9. In some embodiments, the ophthalmic aqueous composition has a pD of less than about 3.8. In some embodiments, the ophthalmic aqueous composition has a pD of less than about 3.7. In some embodiments, the ophthalmic aqueous composition has a pD of less than about 3.6. In some embodiments, the ophthalmic aqueous composition has a pD of less than about 3.5. In some embodiments, the pD is the pD of the ophthalmic aqueous composition after extended period of time under storage condition.

In some embodiments, the pD of the ophthalmic aqueous composition described herein is associated with the stability of the ophthalmic aqueous composition. In some embodiments, a stable composition comprises a pD of between about 3 and about 9, about 4 and about 8, about 4.5 and about 7.8, about 5 and about 7.5, or about 5.5 and about 7. In some embodiments, a stable composition comprises a pD of less than about 8. In some embodiments, a stable composition comprises a pD of less than about 7.9. In some embodiments, a stable composition comprises a pD of less than about 7.8. In some embodiments, a stable composition comprises a pD of less than about 7.7. In some embodiments, a stable composition comprises a pD of less than about 7.6. In some embodiments, a stable composition comprises a pD of less than about 7.5. In some embodiments, a stable composition comprises a pD of less than about 7.4. In some embodiments, a stable composition comprises a pD of less than about 7.3. In some embodiments, a stable composition comprises a pD of less than about 7.2. In some embodiments, a stable composition comprises a pD of less than about 7.1. In some embodiments, a stable composition comprises a pD of less than about 7. In some embodiments, a stable composition comprises a pD of less than about 6.9. In some embodiments, a stable composition comprises a pD of less than about 6.8. In some embodiments, a stable composition comprises a pD of less than about 6.7. In some embodiments, a stable composition comprises a pD of less than about 6.6. In some embodiments, a stable composition comprises a pD of less than about 6.5. In some embodiments, a stable composition comprises a pD of less than about 6.4. In some embodiments, a stable composition comprises a pD of less than about 6.3. In some embodiments, a stable composition comprises a pD of less than about 6.2. In some embodiments, a stable composition comprises a pD of less than about 6.1. In some embodiments, a stable composition comprises a pD of less than about 6. In some embodiments, a stable composition comprises a pD of less than about 5.9. In some embodiments, a stable composition comprises a pD of less than about 5.8. In some embodiments, a stable composition comprises a pD of less than about 5.7. In some embodiments, a stable composition comprises a pD of less than about 5.6. In some embodiments, a stable composition comprises a pD of less than about 5.5. In some embodiments, a stable composition comprises a pD of less than about 5.4. In some embodiments, a stable composition comprises a pD of less than about 5.3. In some embodiments, a stable composition comprises a pD of less than about 5.2. In some embodiments, a stable composition comprises a pD of less than about 5.1. In some embodiments, a stable composition comprises a pD of less than about 5. In some embodiments, a stable composition comprises a pD of less than about 4.9. In some embodiments, a stable composition comprises a pD of less than about 4.8. In some embodiments, a stable composition comprises a pD of less than about 4.7. In some embodiments, a stable composition comprises a pD of less than about 4.6. In some embodiments, a stable composition comprises a pD of less than about 4.5. In some embodiments, a stable composition comprises a pD of less than about 4.4. In some embodiments, a stable composition comprises a pD of less than about 4.3. In some embodiments, a stable composition comprises a pD of less than about 4.2. In some embodiments, a stable composition comprises a pD of less than about 4.1. In some embodiments, a stable composition comprises a pD of less than about 4. In some embodiments, a stable composition comprises a pD of less than about 3.9. In some embodiments, a stable composition comprises a pD of less than about 3.8. In some embodiments, a stable composition comprises a pD of less than about 3.7. In some embodiments, a stable composition comprises a pD of less than about 3.6. In some embodiments, a stable composition comprises a pD of less than about 3.5.

In some embodiments, the $D_2O$ aqueous system stabilizes an ophthalmic agent. In some embodiments, this is due to a lower concentration of the reactive species (e.g., —OD) in the $D_2O$ aqueous system compared to the concentration of the reactive species (e.g., —OH) in an equivalent $H_2O$ aqueous system. In some instances, the concentration of the reactive species (e.g., —OD) in the $D_2O$ aqueous system is about one third less than the concentration of the reactive species (e.g., —OH) in the equivalent $H_2O$ aqueous system. In some cases, this is due to a lower or smaller dissociation constant of $D_2O$ than $H_2O$. For example, the $K_a(H_2O)$ is $1\times10^{-14}$, whereas the $K_a(D_2O)$ is $1\times10^{-1}$. As such, $D_2O$ is a weaker acid than $H_2O$. In some cases, base catalysis leads to the presence of a degradant from the ophthalmic agent. In some cases, with a lower concentration of the reactive species that causes degradant formation, the ophthalmic solution is more stable in a $D_2O$ aqueous system than compared to an equivalent $H_2O$ aqueous system. In some embodiments, the ophthalmic composition formulated with deuterated water allows for a more stable ophthalmic composition relative to the ophthalmic composition formulated with $H_2O$.

In some embodiments, the presence of deuterated water shifts the pKa of the buffer. In some embodiments, the presence of deuterated water allows for the ophthalmic composition to simulate the stability of a lower pH system. In some instances, the buffer capacity of the ophthalmic composition is lowered, thereby allowing a faster shift in pH. In some instances, the lowered buffering capacity of the ophthalmic composition when administered into the eye allows the ophthalmic composition to reach physiological pH at a faster rate than compared to an ophthalmic composition formulated in $H_2O$. In some instances, the ophthalmic composition formulated with deuterated water allows for a lower tear production, or less tear reflex in the eye, in comparison with an ophthalmic composition formulated with $H_2O$.

In some embodiment, the ophthalmic gel or ointment composition described herein has a pD of about 3.5, about 3.6, about 3.7, about 3.8, about 3.9, about 4, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, or about 7.9.

In some embodiment, the pD of the ophthalmic aqueous, gel, or ointment composition described herein is suitable for sterilization (e.g., by filtration or aseptic mixing or heat treatment and/or autoclaving (e.g., terminal sterilization)) of ophthalmic formulations described herein. As used in in the present disclosure, the term "aqueous composition" includes compositions that are based on $D_2O$.

In some embodiments, the pharmaceutical formulations described herein are stable with respect to pD over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 18 months, at least about 24 months, at least about 3 years, at least about 4 years, at least about 5 years, at least about 6 years, at least about 7 years, at least about 8 years, at least about 9 years, at least about 10 years, at least about 15 years, at least about 20 years, at least about 30 years, or more. In other embodiments, the formulations described herein are stable with respect to pD over a period of at least about 1 week. In other embodiments, the formulations described herein are stable with respect to pD over a period of at least about 2 weeks. In other embodiments, the formulations described herein are stable with respect to pD over a period of at least about 3 weeks. In other embodiments, the formulations described herein are stable with respect to pD over a period of at least about 1 month. Also described herein are formulations that are stable with respect to pD over a period of at least about 2 months, at least about 3 months, at least about 4 months, at least about 5 months, at least about 6 months, at least about 12 months, at least about 18 months, at least about 2 years, or more.

Aqueous Solution Dose-To-Dose Uniformity

Typical ophthalmic aqueous solutions are packaged in eye drop bottles and administered as drops. For example, a single administration (i.e. a single dose) of an ophthalmic aqueous solution includes a single drop, two drops, three drops or more into the eyes of the patient. In some embodiments, one dose of the ophthalmic aqueous solution described herein is one drop of the aqueous solution composition from the eye drop bottle.

In some cases, described herein include ophthalmic aqueous compositions which provide a dose-to-dose uniform concentrations. In some instances, the dose-to-dose uniform concentration does not preset significant variations of drug content from one dose to another. In some instances, the dose-to-dose uniform concentration does provide consistent drug content from one dose to another.

In some embodiments, the composition has a dose-to-dose ophthalmic agent concentration variation of less than 50%. In some embodiments, the composition has a dose-to-dose ophthalmic agent concentration variation of less than 40%. In some embodiments, the composition has a dose-to-dose ophthalmic agent concentration variation of less than 30%. In some embodiments, the composition has a dose-to-dose ophthalmic agent concentration variation of less than 20%. In some embodiments, the composition has a dose-to-dose ophthalmic agent concentration variation of less than 10%. In some embodiments, the composition has a dose-to-dose ophthalmic agent concentration variation of less than 5%.

In some embodiments, the dose-to-dose ophthalmic agent concentration variation is based on 10 consecutive doses. In some embodiments, the dose-to-dose ophthalmic agent concentration variation is based on 8 consecutive doses. In some embodiments, the dose-to-dose ophthalmic agent concentration variation is based on 5 consecutive doses. In some embodiments, the dose-to-dose ophthalmic agent concentration variation is based on 3 consecutive doses. In some embodiments, the dose-to-dose ophthalmic agent concentration variation is based on 2 consecutive doses.

A nonsettling formulation should not require shaking to disperse drug uniformly. A "no-shake" formulation is potentially advantageous over formulations that require shaking for the simple reason that patients' shaking behavior is a major source of variability in the amount of drug dosed. It has been reported that patients often times do not or forget to shake their ophthalmic compositions that requires shaking before administering a dose, despite the instructions to shake that were clearly marked on the label. On the other hand, even for those patients who do shake the product, it is normally not possible to determine whether the shaking is adequate in intensity and/or duration to render the product uniform. In some embodiments, the ophthalmic gel compositions and ophthalmic ointment compositions described herein are "no-shake" formulations that maintained the dose-to-dose uniformity described herein.

To evaluate the dose-to-dose uniformity, drop bottles or tubes containing the ophthalmic aqueous compositions, the ophthalmic gel compositions, or ophthalmic ointment compositions are stored upright for a minimum of 12 hours prior to the start of the test. To simulate the recommended dosing of these products, predetermined number of drops or strips are dispensed from each commercial bottles or tubes at predetermined time intervals for an extended period of time or until no product was left in the bottle or tube. All drops and strips are dispensed into tared glass vials, capped, and stored at room temperature until analysis. Concentrations of an ophthalmic agent in the expressed drops are determined using a reverse-phase HPLC method.

Aqueous Solution Viscosity

In some embodiments, the composition has a Brookfield RVDV viscosity of from about 10 to about 50,000 cps at about 20° C. and sheer rate of $1s^{-1}$. In some embodiments, the composition has a Brookfield RVDV viscosity of from about 100 to about 40,000 cps at about 20° C. and sheer rate of $1s^{-1}$. In some embodiments, the composition has a Brookfield RVDV viscosity of from about 500 to about 30,000 cps at about 20° C. and sheer rate of $1s^{-1}$. In some embodiments, the composition has a Brookfield RVDV viscosity of from about 1000 to about 20,000 cps at about 20° C. and sheer rate of $1s^{-1}$. In some embodiments, the composition has a Brookfield RVDV viscosity of from about 2000 to about 10,000 cps at about 20° C. and sheer rate of $1s^{-1}$. In some embodiments, the composition has a Brookfield RVDV viscosity of from about 4000 to about 8000 cps at about 20° C. and sheer rate of $1s^{-1}$.

In some embodiments, the ophthalmic aqueous formulation contains a viscosity enhancing agent sufficient to provide a viscosity of between about 500 and 50,000 centipoise, between about 750 and 50,000 centipoise; between about 1000 and 50,000 centipoise; between about 1000 and 40000 centipoise; between about 2000 and 30,000 centipoise; between about 3000 and 20,000 centipoise; between about 4000 and 10,000 centipoise, or between about 5000 and 8000 centipoise.

In some embodiments, the compositions described herein are low viscosity compositions at body temperature. In some embodiments, low viscosity compositions contain from about 1% to about 10% of a viscosity enhancing agent (e.g., gelling components such as polyoxyethylene-polyoxypropylene copolymers). In some embodiments, low viscosity compositions contain from about 2% to about 10% of a viscosity enhancing agent (e.g., gelling components such as polyoxyethylene-polyoxypropylene copolymers). In some embodiments, low viscosity compositions contain from about 5% to about 10% of a viscosity enhancing agent (e.g., gelling components such as polyoxyethylene-polyoxypropylene copolymers). In some embodiments, low viscosity compositions are substantially free of a viscosity enhancing agent (e.g., gelling components such as polyoxyethylene-polyoxypropylene copolymers). In some embodiments, a low viscosity ophthalmic agent composition described herein provides an apparent viscosity of from about 100 cP to about 10,000 cP. In some embodiments, a low viscosity ophthalmic agent composition described herein provides an apparent viscosity of from about 500 cP to about 10,000 cP. In some embodiments, a low viscosity ophthalmic agent composition described herein provides an apparent viscosity of from about 1000 cP to about 10,000 cP.

Osmolarity

In some embodiments, a composition disclosed herein is formulated in order to not disrupt the ionic balance of the eye. In some embodiments, a composition disclosed herein has an ionic balance that is the same as or substantially the same as the eye. In some embodiments, a composition disclosed herein does not does not disrupt the ionic balance of the eye.

As used herein, "practical osmolarity/osmolality" or "deliverable osmolarity/osmolality" means the osmolarity/osmolality of a composition as determined by measuring the osmolarity/osmolality of the ophthalmic agent and all excipients except the gelling and/or the thickening agent (e.g., polyoxyethylene-polyoxypropylene copolymers, carboxymethylcellulose or the like). The practical osmolarity of a composition disclosed herein is measured by a suitable method, e.g., a freezing point depression method as described in Viegas et. al., Int. J. Pharm., 1998, 160, 157-162. In some instances, the practical osmolarity of a composition disclosed herein is measured by vapor pressure osmometry (e.g., vapor pressure depression method) that allows for determination of the osmolarity of a composition at higher temperatures. In some instances, vapor pressure depression method allows for determination of the osmolarity of a composition comprising a gelling agent (e.g., a thermoreversible polymer) at a higher temperature wherein the gelling agent is in the form of a gel.

In some embodiments, the osmolarity at a target site of action (e.g., the eye) is about the same as the delivered osmolarity of a composition described herein. In some embodiments, a composition described herein has a deliverable osmolarity of about 150 mOsm/L to about 500 mOsm/L, about 250 mOsm/L to about 500 mOsm/L, about 250 mOsm/L to about 350 mOsm/L, about 280 mOsm/L to about 370 mOsm/L or about 250 mOsm/L to about 320 mOsm/L.

The practical osmolality of an ophthalmic composition disclosed herein is from about 100 mOsm/kg to about 1000 mOsm/kg, from about 200 mOsm/kg to about 800 mOsm/kg, from about 250 mOsm/kg to about 500 mOsm/kg, or from about 250 mOsm/kg to about 320 mOsm/kg, or from about 250 mOsm/kg to about 350 mOsm/kg or from about 280 mOsm/kg to about 320 mOsm/kg. In some embodiments, a composition described herein has a practical osmolarity of about 100 mOsm/L to about 1000 mOsm/L, about 200 mOsm/L to about 800 mOsm/L, about 250 mOsm/L to about 500 mOsm/L, about 250 mOsm/L to about 350 mOsm/L, about 250 mOsm/L to about 320 mOsm/L, or about 280 mOsm/L to about 320 mOsm/L.

In some embodiments, suitable tonicity adjusting agents include, but are not limited to any pharmaceutically acceptable sugar, salt or any combinations or mixtures thereof, such as, but not limited to dextrose, glycerin, mannitol, sorbitol, sodium chloride, and other electrolytes. In some instances, the tonicity adjusting agent is selected from sodium chloride, sodium nitrate, sodium sulfate, sodium bisulfate, potassium chloride, calcium chloride, magnesium chloride, zinc chloride, potassium acetate, sodium acetate, sodium bicarbonate, sodium carbonate, sodium thiosulfate, magnesium sulfate, disodium hydrogen phosphate, sodium dihydrogen phosphate, potassium dihydrogen phosphate, dextrose, mannitol, sorbitol, dextrose, sucrose, urea, propylene glycol, glycerin, or a combination thereof.

In some embodiment, the ophthalmic compositions described herein include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Sterility

In some embodiments, the compositions are sterilized. Included within the embodiments disclosed herein are means and processes for sterilization of a pharmaceutical composition disclosed herein for use in humans. The goal is to provide a safe pharmaceutical product, relatively free of infection causing micro-organisms. The U. S. Food and Drug Administration has provided regulatory guidance in the publication "Guidance for Industry: Sterile Drug Products Produced by Aseptic Processing" available at:

http://www.fda.gov/cder/guidance/5882fnl.htm, which is incorporated herein by reference in its entirety.

As used herein, sterilization means a process used to destroy or remove microorganisms that are present in a product or packaging. Any suitable method available for sterilization of objects and compositions is used. Available methods for the inactivation of microorganisms include, but are not limited to, the application of extreme heat, lethal chemicals, or gamma radiation. In some embodiments, a process for the preparation of an ophthalmic formulation comprises subjecting the formulation to a sterilization method selected from heat sterilization, chemical sterilization, radiation sterilization or filtration sterilization. The method used depends largely upon the nature of the device or composition to be sterilized. Detailed descriptions of many methods of sterilization are given in Chapter 40 of Remington. The Science and Practice of Pharmacy published by Lippincott, Williams & Wilkins, and is incorporated by reference with respect to this subject matter.

Filtration

Filtration sterilization is a method used to remove but not destroy microorganisms from solutions. Membrane filters are used to filter heat-sensitive solutions. Such filters are thin, strong, homogenous polymers of mixed cellulosic esters (MCE), polyvinylidene fluoride (PVF; also known as PVDF), or poly tetrafluoroethylene (PTFE) and have pore sizes ranging from 0.1 to 0.22 µm. Solutions of various characteristics are optionally filtered using different filter membranes. For example, PVF and PTFE membranes are well suited to filtering organic solvents while aqueous solutions are filtered through PVF or MCE membranes. Filter apparatus are available for use on many scales ranging from the single point-of-use disposable filter attached to a syringe up to commercial scale filters for use in manufacturing plants. The membrane filters are sterilized by autoclave or chemical sterilization. Validation of membrane filtration systems is performed following standardized protocols (Microbiological Evaluation of Filters for Sterilizing Liquids, Vol 4, No. 3. Washington, D.C. Health Industry Manufacturers Association, 1981) and involve challenging the membrane filter with a known quantity (ca. $10^7/cm^2$) of unusually small microorganisms, such as Brevundimonas diminuta (ATCC 19146).

Pharmaceutical compositions are optionally sterilized by passing through membrane filters. Formulations comprising nanoparticles (U.S. Pat. No. 6,139,870) or multilamellar vesicles (Richard et al., International Journal of Pharmaceutics (2006), 312(1-2):144-50) are amenable to sterilization by filtration through 0.22 µm filters without destroying their organized structure.

In some embodiments, the methods disclosed herein comprise sterilizing the formulation (or components thereof) by means of filtration sterilization. In ophthalmic gel compositions that includes thermosetting polymers, filtration is carried out below (e.g. about 5° C.) the gel temperature (Tgel) of a formulation described herein and with viscosity that allows for filtration in a reasonable time using a peristaltic pump (e.g. below a theoretical value of 100 cP).

Accordingly, provided herein are methods for sterilization of ophthalmic formulations that prevent degradation of polymeric components (e.g., thermosetting and/or other viscosity enhancing agents) and/or the ophthalmic agent during the process of sterilization. In some embodiments, degradation of the ophthalmic agent is reduced or eliminated through the use of specific pD ranges for buffer components and specific proportions of viscosity enhancing agents in the formulations. In some embodiments, the choice of an appropriate viscosity enhancing agents or thermosetting polymer allows for sterilization of formulations described herein by filtration. In some embodiments, the use of an appropriate thermosetting polymer or other viscosity enhancing agents in combination with a specific pD range for the formulation allows for high temperature sterilization of formulations described with substantially no degradation of the therapeutic agent or the polymeric excipients. An advantage of the methods of sterilization provided herein is that, in certain instances, the formulations are subjected to terminal sterilization via autoclaving without any loss of the ophthalmic agent and/or excipients and/or viscosity enhancing agents during the sterilization step and are rendered substantially free of microbes and/or pyrogens.

Radiation Sterilization

One advantage of radiation sterilization is the ability to sterilize many types of products without heat degradation or other damage. The radiation commonly employed is beta radiation or alternatively, gamma radiation from a $^{60}Co$ source. The penetrating ability of gamma radiation allows its use in the sterilization of many product types, including solutions, compositions and heterogeneous mixtures. The germicidal effects of irradiation arise from the interaction of gamma radiation with biological macromolecules. This interaction generates charged species and free-radicals. Subsequent chemical reactions, such as rearrangements and cross-linking processes, result in the loss of normal function for these biological macromolecules. The formulations described herein are also optionally sterilized using beta irradiation.

Sterilization by Heat

Many methods are available for sterilization by the application of high heat. One method is through the use of a saturated steam autoclave. In this method, saturated steam at a temperature of at least 121° C. is allowed to contact the object to be sterilized. The transfer of heat is either directly to the microorganism, in the case of an object to be sterilized, or indirectly to the microorganism by heating the bulk of an aqueous solution to be sterilized. This method is widely practiced as it allows flexibility, safety and economy in the sterilization process.

Microorganisms

In some embodiments, the compositions are substantially free of microorganisms. Acceptable bioburden or sterility levels are based on applicable standards that define therapeutically acceptable compositions, including but not limited to United States Pharmacopeia Chapters <1111> et seq. For example, acceptable sterility (e.g., bioburden) levels include about 10 colony forming units (cfu) per gram of formulation, about 50 cfu per gram of formulation, about 100 cfu per gram of formulation, about 500 cfu per gram of formulation or about 1000 cfu per gram of formulation. In some embodiments, acceptable bioburden levels or sterility for formulations include less than 10 cfu/mL, less than 50 cfu/mL, less than 500 cfu/mL or less than 1000 cfu/mL microbial agents. In addition, acceptable bioburden levels or sterility include the exclusion of specified objectionable microbiological agents. By way of example, specified objectionable microbiological agents include but are not limited to *Escherichia coli* (*E. coli*). *Salmonella* sp., *Pseudomonas aeruginosa* (*P. aeruginosa*) and/or other specific microbial agents.

An important component of the sterility assurance quality control, quality assurance and validation process is the method of sterility testing. Sterility testing, by way of example only, is performed by two methods. The first is direct inoculation wherein a sample of the composition to be tested is added to growth medium and incubated for a period of time up to 21 days. Turbidity of the growth medium indicates contamination. Drawbacks to this method include the small sampling size of bulk materials which reduces sensitivity, and detection of microorganism growth based on a visual observation. An alternative method is membrane filtration sterility testing. In this method, a volume of product is passed through a small membrane filter paper. The filter paper is then placed into media to promote the growth of microorganisms. This method has the advantage of greater sensitivity as the entire bulk product is sampled. The commercially available Millipore Steritest sterility testing system is optionally used for determinations by membrane filtration sterility testing. For the filtration testing of creams or ointments Steritest filter system No. TLHVSL210 are used. For the filtration testing of emulsions or viscous products Steritest filter system No. TLAREM210 or TDAREM210 are used. For the filtration testing of pre-filled syringes Steritest filter system No. TTHASY210 are used. For the filtration testing of material dispensed as an aerosol or foam Steritest filter system No. TTHVA210 are used. For the filtration testing of soluble powders in ampoules or vials Steritest filter system No. TTHADA210 or TTHADV210 are used.

Testing for *E. coli* and *Salmonella* includes the use of lactose broths incubated at 30-35° C. for 24-72 hours, incubation in MacConkey and/or EMB agars for 18-24 hours, and/or the use of Rappaport medium. Testing for the detection of *P. aeruginosa* includes the use of NAC agar. United States Pharmacopeia Chapter <62> further enumerates testing procedures for specified objectionable microorganisms.

In certain embodiments, the ophthalmic formulation described herein has less than about 60 colony forming units (CFU), less than about 50 colony forming units, less than about 40 colony forming units, or less than about 30 colony forming units of microbial agents per gram of formulation. In certain embodiments, the ophthalmic formulations described herein are formulated to be isotonic with the eye.

Endotoxins

An additional aspect of the sterilization process is the removal of by-products from the killing of microorganisms (hereinafter. "Product"). The process of depyrogenation removes pyrogens from the sample. Pyrogens are endotoxins or exotoxins which induce an immune response. An example of an endotoxin is the lipopolysaccharide (LPS) molecule found in the cell wall of gram-negative bacteria. While sterilization procedures such as autoclaving or treatment with ethylene oxide kill the bacteria, the LPS residue induces a proinflammatory immune response, such as septic shock. Because the molecular size of endotoxins vary widely, the presence of endotoxins is expressed in "endotoxin units" (EU). One EU is equivalent to 100 picograms of *E. coli* LPS. In some cases, humans develop a response to as little as 5 EU/kg of body weight. The bioburden (e.g., microbial limit) and/or sterility (e.g., endotoxin level) is expressed in any units as recognized in the art. In certain embodiments, ophthalmic compositions described herein contain lower endotoxin levels (e.g. <4 EU/kg of body weight of a subject) when compared to conventionally acceptable endotoxin levels (e.g., 5 EU/kg of body weight of a subject). In some embodiments, the ophthalmic formulation has less than about 5 EU/kg of body weight of a subject. In other embodiments, the ophthalmic formulation has less than about 4 EU/kg of body weight of a subject. In additional embodiments, the ophthalmic formulation has less than about 3 EU/kg of body weight of a subject. In additional embodiments, the ophthalmic formulation has less than about 2 EU/kg of body weight of a subject.

In some embodiments, the ophthalmic formulation has less than about 5 EU/kg of formulation. In other embodiments, the ophthalmic formulation has less than about 4 EU/kg of formulation. In additional embodiments, the ophthalmic formulation has less than about 3 EU/kg of formulation. In some embodiments, the ophthalmic formulation has less than about 5 EU/kg Product. In other embodiments, the ophthalmic formulation has less than about 1 EU/kg Product. In additional embodiments, the ophthalmic formulation has less than about 0.2 EU/kg Product. In some embodiments, the ophthalmic formulation has less than about 5 EU/g of unit or Product. In other embodiments, the ophthalmic formulation has less than about 4 EU/g of unit or Product. In additional embodiments, the ophthalmic formulation has less than about 3 EU/g of unit or Product. In some embodiments, the ophthalmic formulation has less than about 5 EU/mg of unit or Product. In other embodiments, the ophthalmic formulation has less than about 4 EU/mg of unit or Product. In additional embodiments, the ophthalmic formulation has less than about 3 EU/mg of unit or Product. In certain embodiments, ophthalmic formulations described herein contain from about 1 to about 5 EU/mL of formulation. In certain embodiments, ophthalmic formulations described herein contain from about 2 to about 5 EU/mL of formulation, from about 3 to about 5 EU/mL of formulation, or from about 4 to about 5 EU/mL of formulation.

In certain embodiments, ophthalmic compositions described herein contain lower endotoxin levels (e.g. <0.5 EU/mL of formulation) when compared to conventionally acceptable endotoxin levels (e.g., 0.5 EU/mL of formulation). In some embodiments, the ophthalmic formulation has less than about 0.5 EU/mL of formulation. In other embodiments, the ophthalmic formulation has less than about 0.4

EU/mL of formulation. In additional embodiments, the ophthalmic formulation has less than about 0.2 EU/mL of formulation.

Pyrogen detection, by way of example only, is performed by several methods. Suitable tests for sterility include tests described in United States Pharmacopoeia (USP)<71> Sterility Tests (23rd edition, 1995). The rabbit pyrogen test and the Limulus amebocyte lysate test are both specified in the United States Pharmacopeia Chapters <85> and <151> (USP23/NF 18, Biological Tests, The United States Pharmacopeial Convention, Rockville, MD, 1995). Alternative pyrogen assays have been developed based upon the monocyte activation-cytokine assay. Uniform cell lines suitable for quality control applications have been developed and have demonstrated the ability to detect pyrogenicity in samples that have passed the rabbit pyrogen test and the Limulus amebocyte lysate test (Taktak et al, J. Pharm. Pharmacol. (1990), 43:578-82). In an additional embodiment, the ophthalmic formulation is subject to depyrogenation. In a further embodiment, the process for the manufacture of the ophthalmic formulation comprises testing the formulation for pyrogenicity. In certain embodiments, the formulations described herein are substantially free of pyrogens.

Ophthalmic Agent-Mucus Penetrating Particle (MPP) Composition

Mucus-penetrating particles (MPPs) are particles that rapidly traverse mucus (e.g. human mucus). In some cases, MPPs comprise of a nanoparticle with a particle size of between about 200 nm and 500 nm. In some instances, the nanoparticle is further coated with a mucus penetrating agent. In some instances, a composition described herein is formulated with MPPs for mucus penetration. In some instances, an ophthalmic composition described herein is formulated with MPPs for mucus penetration. In some embodiments, an ophthalmic agent includes aflibercept (also known as VEGF Trap), ranibizumab, pegaptanib, cyclopentolate, phenylephrine, homatropine, scopolamine, cyclopentolate/phenylephrine, phenylephrine/scopolamine, tropicamide, ketorolac/phenylephrine, hydroxyamphetamine/tropicamide, cysteamine, ocriplasmin, mitomycin, dapiprazole, lidocaine, proparacaine, tetracaine, benoxinate, azithromycin, bacitracin, besifloxacin, boric acid, chloramphenicol, ciprofloxacin, erythromycin, ganciclovir, gatifloxacin, gentamicin, idoxuridine, levofloxacin, moxifloxacin, natamycin, norfloxacin, ofloxacin, bacitracin/polymyxin b, tobramycin, polymyxin b/trimethoprim, povidone iodine, trifluridine, gramicidin/neomycin/polymyxin b, sulfacetamide sodium, sulfisoxazole, bacitracin/neomycin/polymyxin b, oxytetracycline/polymyxin b, phenylephrine/sulfacetamide sodium, vidarabine, bromfenac, nepafenac, ketorolac, cyclosporine, flurbiprofen, suprofen, diclofenac, alcaftadine, azelastine, bepotastine, cromolyn, emedastine, epinastine, ketotifen, levocabastine, lodoxamide, nedocromil, naphazoline, naphazoline/pheniramine, naphazoline/zinc sulfate, olopatadine, oxymetazoline, pemirolast, phenylephrine, phenylephrine/zinc sulfate, tetrahydrozoline, tetrahydrozoline (zinc sulfate, fluorescein, fluorescein/proparacaine, benoxinate/fluorescein, indocyanine green, trypan blue, acetylcholine, apraclonidine, betaxolol, bimatoprost, brimonidine, brinzolamide, brimonidine/brinzolamide, carbachol, carteolol, demecarium bromide, dipivefrin, dorzolamide, dorzolamide/timolol, echothiophate iodide, epinephrine, epinephrine/pilocarpine, latanoprost, levobunolol, levobetaxolol, metipranolol, physostigmine, pilocarpine, tafluprost, timolol, travoprost, unoprostone, artificial tear, dexamethasone, difluprednate, fluocinolone, fluorometholone, loteprednol, medrysone, prednisolone, rimexolone, triamcinolone, fluorometholone/sulfacetamide sodium, dexamethasone/neomycin, dexamethasone/tobramycin, dexamethasone/neomycin/polymyxin b, loteprednol/tobramycin, prednisolone/sulfacetamide sodium, bacitracin/hydrocortisone/neomycin/polymyxin b, hydrocortisone/neomycin/polymyxin b, chloramphenicol/hydrocortisone/polymyxin b, neomycin/polymyxin b/prednisolone, gentamicin/prednisolone, ketorolac/phenylephrine, diphenhydramine, dimenhydrinate, dicyclomine, flavoxate, oxybutynin, tiotropium, hyoscine, scopolomine (L-hyoscine), hydroxyzine, ipratropium, pirenzapine, solifenacin, darifenacin, benzatropine, mebeverine, procyclidine, aclidinium bromide, trihexyphenidyl/benzhexol, tolterodine, or any combinations thereof. In a non-limiting example, the MMPs for use in the disclosed composition is obtained from Kala Pharmaceuticals, Inc. (100 Beaver Street #201, Waltham, MA 02453).

In some embodiments, the nanoparticle comprises of any suitable material, such as an organic material, an inorganic material, a polymer, or combinations thereof. In some instances, the nanoparticle comprises of inorganic material, such as for example, a metal (e.g., Ag, Au, Pt, Fe, Cr, Co. Ni, Cu. Zn, and other transition metals), a semiconductor (e.g., silicon, silicon compounds and alloys, cadmium selenide, cadmium sulfide, indium arsenide, and indium phosphide), or an insulator (e.g., ceramics such as silicon oxide). In some instances, the nanoparticle comprises organic materials such as a synthetic polymer and/or a natural polymer. Examples of synthetic polymers include non-degradable polymers such as polymethacrylate and degradable polymers such as polylactic acid, polyglycolic acid and copolymers thereof. Examples of natural polymers include hyaluronic acid, chitosan, and collagen.

In some embodiments, the nanoparticle is coated with a mucus penetrating agent. In some instances, the mucus penetrating agent comprises any suitable material, such as a hydrophobic material, a hydrophilic material, and/or an amphiphilic material. In some instances, the mucus penetrating agent is a polymer. In some instances, the polymer a synthetic polymer (i.e., a polymer not produced in nature). In other embodiments, the polymer is a natural polymer (e.g., a protein, polysaccharide, rubber). In certain embodiments, the polymer is a surface active polymer. In certain embodiments, the polymer is a non-ionic polymer. In certain embodiments, the polymer is a non-ionic block copolymer. In some embodiments, the polymer is a diblock copolymer, a triblock copolymer, e.g., e.g., where one block is a hydrophobic polymer and another block is a hydrophilic polymer. In some instances, the polymer is charged or uncharged.

Additional examples of suitable polymers include, but are not limited to, polyamines, polyethers, polyamides, polyesters, poly carbamates, polyureas, polycarbonates, polystyrenes, polyimides, polysulfones, polyurethanes, poly acetylenes, polyethylenes, polyethyleneimines, polyisocyanates, polyacrylates, polymethacrylates, poly acrylonitriles, and polyarylates. Non-limiting examples of specific polymers include poly(caprolactone)(PCL), ethylene vinyl acetate polymer (EVA), poly(lactic acid)(PLA), poly(L-lactic acid) (PLLA), poly(glycolic acid)(PGA), poly(lactic acid-co-glycolic acid)(PLGA), poly(L-lactic acid-co-glycolic acid) (PLLGA), poly(D, L-lactide)(PDLA), poly(L-lactide) (PLLA), poly(D, L-lactide-co-caprolactone), poly(D, L-lactide-co-caprolactone-co-glycolide), poly(D, L-lactide-co-PEO-co-D, L-lactide), poly(D, L-lactide-co-PPO-co-D, L-lactide), polyalkyl cyanoacrylate, polyurethane, poly-L- lysine (PLL), hydroxypropyl methacrylate (HPMA), poly (ethylene glycol), poly-L-glutamic acid, poly(hydroxy acids), polyanhydrides, polyorthoesters, poly(ester amides), poly amides, poly(ester ethers), polycarbonates, polyalkylenes such as polyethylene and polypropylene, polyalkylene glycols such as poly(ethyleneglycol)(PEG), polyalkylene oxides (PEO), polyalkylene terephthalates such as poly(ethyleneterephthalate), polyvinyl alcohols (PVA), polyvinyl ethers, polyvinyl esters such as poly(vinyl acetate), polyvinyl halides such as poly(vinyl chloride) (PVC), poly vinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate)(PMMA), poly(ethyl(meth) acrylate), poly(butyl(meth)acrylate), poly(isobutyl(meth) acrylate), poly(hexyl(meth)acrylate), poly(isodecyl(meth) acrylate), poly(lauryl(meth)acrylate), poly(phenyl(meth) acrylate), poly(methyl acrylate), poly(isopropyl acrylate), poly(isobutyl acrylate), poly(octadecyl acrylate)(jointly referred to herein as "polyacrylic acids"), and copolymers and mixtures thereof, polydioxanone and its copolymers, polyhydroxyalkanoates, polypropylene fumarate), poly oxymethylene, poloxamers, poly(ortho)esters, poly(butyric acid), poly(valeric acid), poly(lactide-co-caprolactone), and trimethylene carbonate, polyvinylpyrrolidone.

In some cases, an ophthalmic agent is present in the MPP formulation at a concentration of between about 0.001 wt % and about 20 wt %, between about 0.01% to about 15%, between about 0.05% to about %10, between about 0.1% to about 5%, or between about 0.5% to about 10% of the ophthalmic agent, or pharmaceutically acceptable prodrug or salt thereof, by weight of the composition. In some instances, additional agents such as buffers, pD adjusting agents, and/or preservatives are formulated in the MPP formulation.

In some instances, ophthalmic agent-MPP composition is formulated using any suitable method. In some embodiments, a milling process is used to reduce the size of a solid material to form particles in the micrometer to nanometer size range. Dry and wet milling processes such as jet milling, cryo-milling, ball milling, media milling, and homogenization are known and are used in methods described herein. Generally, in a wet milling process, a suspension of the material to be used as the nanoparticle is mixed with milling media with or without excipients to reduce particle size. Dry milling is a process wherein the material to be used as the nanoparticle is mixed with milling media with or without excipients to reduce particle size. In a cryo-milling process, a suspension of the material to be used as the nanoparticle is mixed with milling media with or without excipients under cooled temperatures.

In some embodiments, any suitable grinding medium is used for milling. In some embodiments, a ceramic and/or polymeric material and/or a metal is used. Examples of suitable materials include zirconium oxide, silicon carbide, silicon oxide, silicon nitride, zirconium silicate, yttrium oxide, glass, alumina, alpha-alumina, aluminum oxide, polystyrene, poly(methyl methacrylate), titanium, steel. In some embodiments, a grinding medium has any suitable size. For example, the grinding medium has an average diameter of at least about 0.1 mm, at least about 0.2 mm, at least about 0.5 mm, at least about 0.8 mm, at least about 1 mm, at least about 2 mm, or at least about 5 mm. In some cases, the grinding medium has an average diameter of less than or equal to about 5 mm, less than or equal to about 2 mm, less than or equal to about 1 mm, less than or equal to about 0.8, less than or equal to about 0.5 mm, or less than or equal to about 0.2 mm. Combinations of the above-referenced ranges are also possible (e.g., an average diameter of at least about 0.5 millimeters and less than or equal to about 1 mm). Other ranges are also possible.

In some embodiments, any suitable solvent is used for milling. In some instances, the choice of solvent depends on factors such as the solid material being milled, the particular type of stabilizer/mucus penetrating agent being used (e.g., one that renders the particle mucus penetrating), the grinding material be used, among other factors. Suitable solvents include ones that do not substantially dissolve the solid material or the grinding material, but dissolve the stabilizer/mucus penetrating agent to a suitable degree. Non-limiting examples of solvents include water, buffered solutions, other aqueous solutions, alcohols (e.g., ethanol, methanol, butanol), and mixtures thereof that optionally include other components such as pharmaceutical excipients, polymers, pharmaceutical agents, salts, preservative agents, viscosity modifiers, tonicity modifier, taste masking agents, antioxidants, pD modifier, and other pharmaceutical excipients. In other embodiments, an organic solvent is used. In some embodiments, a pharmaceutical agent has any suitable solubility in these or other solvents, such as a solubility in one or more of the ranges described above for aqueous solubility or for solubility in a coating solution.

In some instances, a MPP is a MPP as described in WO2013/166385. In some instances, a MPP is a MPP as described in Lai et al., "Rapid transport of large polymeric nanoparticles in fresh undiluted human mucus," *PNAS* 104 (5):1482-1487 (2007). In some instances, an ophthalmic agent-MPP composition is formulated using a method as described in WO2013/166385. In some instances, an ophthalmic agent-MPP composition is formulated using a method as described in Lai et al., "Rapid transport of large polymeric nanoparticles in fresh undiluted human mucus," *PNAS* 104(5):1482-1487 (2007).

Ophthalmic Gel Composition

Gels have been defined in various ways. For example, the United States Pharmacopoeia defines gels as semisolid systems consisting of either suspensions made up of small inorganic particles or large organic molecules interpenetrated by a liquid. Gels include a single-phase or a two-phase system. A single-phase gel consists of organic macromolecules distributed uniformly throughout a liquid in such a manner that no apparent boundaries exist between the dispersed macromolecules and the liquid. Some single-phase gels are prepared from synthetic macromolecules (e.g., carbomer) or from natural gums, (e.g., tragacanth). In some embodiments, single-phase gels are generally aqueous, but will also be made using alcohols and oils. Two-phase gels consist of a network of small discrete particles.

In some embodiments, gels are also classified as being hydrophobic or hydrophilic. In certain embodiments, the base of a non-limiting example of a hydrophobic gel includes a liquid paraffin with polyethylene or fatty oils gelled with colloidal silica, or aluminum or zinc soaps. In contrast, the base of a non-limiting example of a hydrophilic gel includes water, glycerol, or propylene glycol gelled with a suitable gelling agent (e.g., tragacanth, starch, cellulose derivatives, carboxy vinylpolymers, and magnesium-aluminum silicates). In certain embodiments, the rheology of the compositions disclosed herein is pseudo plastic, plastic, thixotropic, or dilatant.

In some embodiments, the ophthalmic composition is an ophthalmic gel, and wherein the ophthalmically acceptable carrier comprises deuterated water and at least one viscosity-enhancing agent. In some embodiments, the viscosity-enhancing agent is selected from cellulose-based polymers, polyoxyethylene-polyoxypropylene triblock copolymers, dextran-based polymers, polyvinyl alcohol, dextrin, polyvinylpyrrolidone, polyalkylene glycols, chitosan, collagen, gelatin, hyaluronic acid, or combinations thereof.

In some embodiment, the ophthalmic gel composition described herein is a semi-solid or id in a gelled state before it is topically administered (e.g. at room temperature). For example, suitable viscosity-enhancing agents for such gels include by way of example only, gelling agents and suspending agents. In one embodiment, the enhanced viscosity formulation does not include a buffer. In other embodiments, the enhanced viscosity formulation includes a pharmaceutically acceptable buffer. Sodium chloride or other tonicity agents are optionally used to adjust tonicity, if necessary.

By way of example only, the ophthalmically acceptable viscosity agent includes hydroxypropyl methylcellulose, hydroxyethyl cellulose, polyvinylpyrrolidone, carboxymethyl cellulose, polyvinyl alcohol, sodium chondroitin sulfate, sodium hyaluronate. Other viscosity enhancing agents compatible with the targeted ocular site include, but are not limited to, acacia (gum arabic), agar, aluminum magnesium silicate, sodium alginate, sodium stearate, bladderwrack, bentonite, carbomer, carrageenan, Carbopol, xanthan, cellulose, microcrystalline cellulose (MCC), ceratonia, chitin, carboxymethylated chitosan, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxy ethyl methacrylate), oxypoly gelatin, pectin, polygeline, povidone, propylene carbonate, methyl vinyl ether/maleic anhydride copolymer (PVM/MA), poly(methoxyethyl methacrylate), poly(methoxyethoxyethyl methacrylate), hydroxypropyl cellulose, hydroxy propylmethyl-cellulose (HPMC), sodium carboxymethyl-cellulose (CMC), silicon dioxide, polyvinylpyrrolidone (PVP: povidone), Splenda® (dextrose, maltodextrin and sucralose) or combinations thereof. In specific embodiments, the viscosity-enhancing excipient is a combination of MCC and CMC. In another embodiment, the viscosity-enhancing agent is a combination of carboxymethylated chitosan, or chitin, and alginate. The combination of chitin and alginate with the ophthalmic agents disclosed herein acts as a controlled release formulation, restricting the diffusion of the ophthalmic agents from the formulation. Moreover, the combination of carboxymethylated chitosan and alginate is optionally used to assist in increasing the permeability of the ophthalmic agents in the eye.

In some embodiments is an enhanced viscosity formulation, comprising from about 0.1 mM and about 100 mM of an ophthalmic agent, a pharmaceutically acceptable viscosity agent, and water for injection, the concentration of the viscosity agent in the water being sufficient to provide an enhanced viscosity formulation with a final viscosity from about 100 to about 100,000 cP. In certain embodiments, the viscosity of the gel is in the range from about 100 to about 50,000 cP, about 100 cP to about 1,000 cP, about 500 cP to about 1500 cP, about 1000 cP to about 3000 cP, about 2000 cP to about 8,000 cP, about 4,000 cP to about 50,000 cP, about 10,000 cP to about 500,000 cP, about 15,000 cP to about 1,000,000 cP. In other embodiments, when an even more viscous medium is desired, the biocompatible gel comprises at least about 35%, at least about 45%, at least about 55%, at least about 65%, at least about 70%, at least about 75%, or even at least about 80% or so by weight of the ophthalmic agent. In highly concentrated samples, the biocompatible enhanced viscosity formulation comprises at least about 25%, at least about 35%, at least about 45%, at least about 55%, at least about 65%, at least about 75%, at least about 85%, at least about 90% or at least about 95% or more by weight of the ophthalmic agent.

In one embodiment, the pharmaceutically acceptable enhanced viscosity ophthalmically acceptable formulation comprises at least one ophthalmic agent and at least one gelling agent. Suitable gelling agents for use in preparation of the gel formulation include, but are not limited to, celluloses, cellulose derivatives, cellulose ethers (e.g., carboxymethylcellulose, ethylcellulose, hydroxyethylcellulose, hydroxymethylcellulose, hydroxypropylmethylcellulose, hydroxypropylcellulose, methylcellulose), guar gum, xanthan gum, locust bean gum, alginates (e.g., alginic acid), silicates, starch, tragacanth, carboxyvinyl polymers, carrageenan, paraffin, petrolatum and any combinations or mixtures thereof. In some other embodiments, hydroxypropylmethylcellulose (Methocel®) is utilized as the gelling agent. In certain embodiments, the viscosity enhancing agents described herein are also utilized as the gelling agent for the gel formulations presented herein.

In some embodiments, the ophthalmic gel composition described herein is an in situ gel formulation. In some instances, the in situ gel formation is based on increased pre-corneal residence time of the ophthalmic composition which improves ocular bioavailability, corneal mucoadhesion, lysosomal interaction and ionic gelation, improved corneal absorption, thermal gelation, or a combination thereof. In some instances, the in situ gel formulation is activated by pH, temperature, ion, UV, or solvent exchange.

In some instances, the ophthalmic gel composition comprises an ophthalmic agent and one or more gelling agents. In some instances, the gelling agent includes, but is not limited to, poloxamer (e.g. Poloxamer 407), tetronics, ethyl (hydroxyethyl) cellulose, cellulose acetate phthalate (CAP), carbopol (e.g. Carbopol 1342P NF, Carbopol 980NF), alginates (e.g. low acetyl gellan gum (Gelrite®)), gellan, hyaluronic acid, pluronics (e.g. Pluronic F-127), chitosan, polyvinyl alcohol (PVA), polyvinylpyrrolidone (PVP), dextran, hydroxy propyl methyl cellulose (HPMC), hydroxyethylcellulose (HEC), methylcellulose (MC), thiolated xyloglucan, polymethacrilic acid (PMMA), polyethylene glycol (PEG), pseudolatexes, xyloglucans, or combinations thereof.

In some instances, the in situ gel formation further comprises a permeation enhancer. In some instances, the permeation enhancer includes surfactants (e.g. non-ionic surfactants), benzalkonium chloride, EDTA, surface-active heteroglycosides, calcium chelators, hydroxyl propyl beta cyclodextrin (HP beta CD), bile salts, and the like.

In some embodiments, other gel formulations are useful depending upon the particular ophthalmic agent, other pharmaceutical agent or excipients/additives used, and as such are considered to fall within the scope of the present disclosure. For example, other commercially-available glycerin-based gels, glycerin-derived compounds, conjugated, or crosslinked gels, matrices, hydrogels, and polymers, as well as gelatins and their derivatives, alginates, and alginate-based gels, and even various native and synthetic hydrogel and hydrogel-derived compounds are all expected to be useful in the ophthalmic agent formulations described herein. In some embodiments, ophthalmically acceptable gels include, but are not limited to, alginate hydrogels SAF®-Gel (ConvaTec, Princeton, N.J.), Duoderm® Hydroactive Gel (ConvaTec), Nu-gel® (Johnson & Johnson Medical. Arlington, Tex.); Carrasyn® (V) Acemannan Hydrogel (Carrington Laboratories, Inc., Irving, Tex.); glycerin gels Elta® Hydrogel (Swiss-American Products, Inc., Dallas, Tex.) and K-Y®, Sterile (Johnson & Johnson). In further embodiments, biodegradable biocompatible gels also represent compounds present in ophthalmically acceptable formulations disclosed and described herein.

In some embodiments, the viscosity-enhancing agent is a cellulose-based polymer selected from cellulose gum, alkylcellulose, hydroxyl-alkyl cellulose, hydroxyl-alkyl alkylcellulose, carboxy-alkyl cellulose, or combinations thereof. In some embodiments, the viscosity-enhancing agent is hydroxyl-alkyl alkylcellulose. In some embodiment, the viscosity-enhancing agent is hydroxypropyl methylcellulose.

In certain embodiments, the enhanced viscosity formulation is characterized by a phase transition between room temperature and body temperature (including an individual with a serious fever, e.g., up to about 42° C.). In some embodiments, the phase transition occurs at 1° C. below body temperature, at 2° C. below body temperature, at 3° C. below body temperature, at 4° C. below body temperature, at 6° C. below body temperature, at 8° C. below body temperature, or at 10° C. below body temperature. In some embodiments, the phase transition occurs at about 15° C. below body temperature, at about 20° C. below body temperature or at about 25° C. below body temperature. In specific embodiments, the gelation temperature (Tgel) of a formulation described herein is about 20° C., about 25° C., or about 30° C. In certain embodiments, the gelation temperature (Tgel) of a formulation described herein is about 35° C., or about 40° C. Included within the definition of body temperature is the body temperature of a healthy individual, or an unhealthy individual, including an individual with a fever (up to −42° C.). In some embodiments, the pharmaceutical compositions described herein are liquids at about room temperature and are administered at or about room temperature.

Copolymers polyoxypropylene and polyoxyethylene (e.g. polyoxyethylene-poly oxy propylene triblock copolymers) form thermosetting gels when incorporated into aqueous solutions. These polymers have the ability to change from the liquid state to the gel state at temperatures close to body temperature, therefore allowing useful formulations that are applied to the targeted ocular site. The liquid state-to-gel state phase transition is dependent on the polymer concentration and the ingredients in the solution.

In some embodiments, the amount of thermosetting polymer in any formulation described herein is about 10%, about 15%, about 20%, about 25%, about 30%, about 35% or about 40% of the total weight of the formulation. In some embodiments, the amount of thermosetting polymer in any formulation described herein is about 10%, about 11%, about 12%, about 13%, about 14%, about 15%, about 16%, about 17%, about 18%, about 19%, about 20%, about 21%, about 22%, about 23%, about 24% or about 25% of the total weight of the formulation. In some embodiments, the amount of thermosetting polymer (e.g., Poloxamer 407) in any formulation described herein is about 7.5% of the total weight of the formulation. In some embodiments, the amount of thermosetting polymer (e.g., Poloxamer 407) in any formulation described herein is about 10% of the total weight of the formulation. In some embodiments, the amount of thermosetting polymer (e.g., Poloxamer 407) in any formulation described herein is about 11% of the total weight of the formulation. In some embodiments, the amount of thermosetting polymer (e.g., Poloxamer 407) in any formulation described herein is about 12% of the total weight of the formulation. In some embodiments, the amount of thermosetting polymer (e.g., Poloxamer 407) in any formulation described herein is about 13% of the total weight of the formulation. In some embodiments, the amount of thermosetting polymer (e.g., Poloxamer 407) in any formulation described herein is about 14% of the total weight of the formulation. In some embodiments, the amount of thermosetting polymer (e.g., Poloxamer 407) in any formulation described herein is about 15% of the total weight of the formulation. In some embodiments, the amount of thermosetting polymer (e.g., Poloxamer 407) in any formulation described herein is about 16% of the total weight of the formulation. In some embodiments, the amount of thermosetting polymer (e.g., Poloxamer 407) in any formulation described herein is about 17% of the total weight of the formulation. In some embodiments, the amount of thermosetting polymer (e.g., Poloxamer 407) in any formulation described herein is about 18% of the total weight of the formulation. In some embodiments, the amount of thermosetting polymer (e.g., Poloxamer 407) in any formulation described herein is about 19% of the total weight of the formulation. In some embodiments, the amount of thermosetting polymer (e.g., Poloxamer 407) in any formulation described herein is about 20% of the total weight of the formulation. In some embodiments, the amount of thermosetting polymer (e.g., Poloxamer 407) in any formulation described herein is about 21% of the total weight of the formulation. In some embodiments, the amount of thermosetting polymer (e.g., Poloxamer 407) in any formulation described herein is about 23% of the total weight of the formulation. In some embodiments, the amount of thermosetting polymer (e.g., Poloxamer 407) in any formulation described herein is about 25% of the total weight of the formulation. In some embodiments, the amount of thickening agent (e.g., a gelling agent) in any formulation described herein is about 1%, about 5%, about 10%, or about 15% of the total weight of the formulation. In some embodiments, the amount of thickening agent (e.g., a gelling agent) in any formulation described herein is about 0.5%, about 1%, about 1.5%, about 2%, about 2.5%, about 3%, about 3.5%, about 4%, about 4.5%, or about 5% of the total weight of the formulation.

In an alternative embodiment, the thermogel is a PEG-PLGA-PEG triblock copolymer (Jeong et al, Nature (1997), 388:860-2; Jeong et al, J. Control. Release (2000), 63:155-63; Jeong et al, Adv. Drug Delivery Rev. (2002), 54:37-51). The polymer exhibits sol-gel behavior over a concentration of about 5% w/w to about 40% w/w. Depending on the properties desired, the lactide/glycolide molar ratio in the PLGA copolymer ranges from about 1:1 to about 20:1. The resulting copolymers are soluble in water and form a free-flowing liquid at room temperature, but form a hydrogel at body temperature. A commercially available PEG-PLGA-PEG triblock copolymer is RESOMER RGP t50106 manufactured by Boehringer Ingelheim. This material is composed of a PLGA copolymer of 50:50 poly(DL-lactide-co-glycolide) and is 10% w/w of PEG and has a molecular weight of about 6000.

Additional biodegradable thermoplastic polyesters include AtriGel® (provided by Atrix Laboratories, Inc.) and/or those disclosed, e.g., in U.S. Pat. Nos. 5,324,519; 4,938,763; 5,702,716; 5,744,153; and 5,990,194; wherein the suitable biodegradable thermoplastic polyester is disclosed as a thermoplastic polymer. Examples of suitable biodegradable thermoplastic polyesters include polylactides, polyglycolides, polycaprolactones, copolymers thereof, terpolymers thereof, and any combinations thereof. In some such embodiments, the suitable biodegradable thermoplastic polyester is a polylactide, a polyglycolide, a copolymer thereof, a terpolymer thereof, or a combination thereof. In one embodiment, the biodegradable thermoplastic polyester is 50/50 poly(DL-lactide-co-glycolide) having a carboxy terminal group; is present in about 30 wt. % to about 40 wt. % of the composition; and has an average molecular weight of about 23,000 to about 45,000. Alternatively, in another embodiment, the biodegradable thermoplastic polyester is 75/25 poly (DL-lactide-co-glycolide) without a carboxy terminal group; is present in about 40 wt. % to about 50 wt. % of the composition; and has an average molecular weight of about 15,000 to about 24,000. In further or alternative embodiments, the terminal groups of the poly(DL-lactide-co-glycolide) are either hydroxyl, carboxyl, or ester depending upon the method of polymerization. Poly condensation of lactic or glycolic acid provides a polymer with terminal hydroxyl and carboxyl groups. Ring-opening polymerization of the cyclic lactide or glycolide monomers with water, lactic acid, or glycolic acid provides polymers with the same terminal groups. However, ring-opening of the cyclic monomers with a monofunctional alcohol such as methanol, ethanol, or 1-dodecanol provides a polymer with one hydroxyl group and one ester terminal groups. Ring-opening polymerization of the cyclic monomers with a diol such as 1,6-hexanediol or polyethyleneglycol provides a polymer with only hydroxyl terminal groups.

Since the polymer systems of thermosetting gels dissolve more completely at reduced temperatures, methods of solubilization include adding the required amount of polymer to the amount of water to be used at reduced temperatures. Generally after wetting the polymer by shaking, the mixture is capped and placed in a cold chamber or in a thermostatic container at about 0-10° C. in order to dissolve the polymer. The mixture is stirred or shaken to bring about a more rapid dissolution of the thermosetting gel polymer. The ophthalmic agent and various additives such as buffers, salts, and preservatives are subsequently added and dissolved. In some instances the pharmaceutically agent is suspended if it is insoluble in water. The pD is modulated by the addition of appropriate buffering agents.

Ophthalmic Ointment Composition

An ointment is a homogeneous, viscous, semi-solid preparation, most commonly a greasy, thick oil (e.g. oil 80%-water 20%) with a high viscosity, intended for external application to the skin or mucous membranes. Ointments have a water number that defines the maximum amount of water that it contains. They are used as emollients or for the application of active ingredients to the skin for protective, therapeutic, or prophylactic purposes and where a degree of occlusion is desired. Ointments are used topically on a variety of body surfaces. These include the skin and the mucous membranes of the eye (an eye ointment), vulva, anus, and nose The vehicle of an ointment is known as the ointment base. The choice of a base depends upon the clinical indication for the ointment. The different types of ointment bases are: hydrocarbon bases, e.g. hard paraffin, soft paraffin, microcrystalline wax and ceresine; absorption bases, e.g. wool fat, beeswax; water soluble bases, e.g. macrogols 200, 300, 400; emulsifying bases, e.g. emulsifying wax, cetrimide; vegetable oils, e.g. olive oil, coconut oil, sesame oil, almond oil and peanut oil.

Ointments are formulated using hydrophobic, hydrophilic, or water-emulsifying bases to provide preparations that are immiscible, miscible, or emulsifiable with skin secretions. In some instances, they are also derived from hydrocarbon (fatty), absorption, water-removable, or water-soluble bases. The active agents are dispersed in the base, and later they get divided after the drug penetration into the target sites (e.g. membranes, skins, etc.).

In some embodiments, poly(ethylene-glycols), polyethoxylated castor oils (Cremophor® EL), alcohols having 12 to 20 carbon atoms or a mixture of two or more of said components are effective excipients for dispersing and/or dissolving effective amounts of ophthalmic drugs, in particular of ascomycins and staurosporine derivatives, in an ointment base, in particular in an ointment base substantially comprising oleaginous and hydrocarbon components, and that the resulting ointments are excellently tolerated by the skin and by ocular tissue.

The present disclosure further recognizes that ophthalmic drugs incorporated in the ointment compositions describes herein target the choroid and/or retina in a patient when the compositions are topically administered to the ocular surface, in particular to the sclera of said patient. In some embodiments, an ophthalmic ointment composition includes an ophthalmic drug, an ointment base and an agent for dispersing and/or dissolving said drug in the ointment base, selected from a poly(ethylene-glycol), a polyethoxylated castor oil, an alcohol having 12 to 20 carbon atoms and a mixture of two or more of said components.

In some embodiments, the ointment bases include ophthalmically acceptable oil and fat bases, such as natural wax e.g. white and yellow bees wax, carnauba wax, wool wax (wool fat), purified lanolin, anhydrous lanolin; petroleum wax e.g. hard paraffin, microcrystalline wax; hydrocarbons e.g. liquid paraffin, white and yellow soft paraffin, white petrolatum, yellow petrolatum; or combinations thereof.

The above mentioned oil and fat bases are described in more detail, for instance, in the British Pharmacopoeia, Edition 2001, or the European Pharmacopoeia, 3rd Edition.

The ointment base is present in amounts of about 50 to about 95, preferably of 70 to 90% by weight based on the total weight of the composition.

A preferred ointment base comprises a combination of one or more of one or more natural waxes like those indicated above, preferably wool wax (wool fat), and one or more hydrocarbons like those indicated above, preferably a soft paraffin or a petrolatum, more preferably in combination with liquid paraffin.

A special embodiment of the aforementioned ointment base comprises e.g. 5 to 17 parts by weight of wool fat, and 50 to 65 parts by weight of white petrolatum as well as 20 to 30 parts by weight of liquid paraffin.

The agent for dispersing and/or dissolving the ophthalmic drug in the ointment base is selected from a poly(ethylene-glycol), a polyethoxylated castor oil, an alcohol having 12 to 20 carbon atoms and a mixture of two or more of said components. The agent is preferably used in amounts of 1 to 20 percent, more preferably 1 to 10 percent by weight of the entire semisolid ophthalmic composition.

Alcohols having 12 to 20 carbon atoms include particularly stearyl alcohol ($C_{18}H_{37}OH$), cetyl alcohol ($C_{16}H_{33}OH$) and mixtures thereof. Preferred are so-called cetostearyl alcohols, mixtures of solid alcohols substantially consisting of stearyl and cetyl alcohol and preferably comprising not less than 40 percent by weight of stearyl alcohol and a sum of stearyl alcohol and cetyl alcohol amounting to at least 90 percent by weight, and compositions comprising not less than 80 percent by weight of cetylstearyl alcohol and an emulsifier, in particular sodium cetostearyl sulfate and/or sodium lauryl sulfate, preferably in amounts not less than 7 percent by weight of emulsifier.

Polyethoxylated castor oils are reaction products of natural or hydrogenated castor oils and ethylene glycol. Such products are obtained in known manner, e.g. by reaction of a natural or hydrogenated castor oil or fractions thereof with ethylene oxide, e.g. in a molar ratio of from about 1:30 to about 1:60, with optional removal of free polyethylene glycol components from the product, e.g. in accordance with the methods disclosed in German Auslegeschriften 1,182, 388 and 1,518,819. Especially suitable and preferred is a product commercially available under the trade name Cremophor® EL having a molecular weight (by steam osmometry)=ca. 1630, a saponification no.=ca. 65-70, an acid no.=ca 2, an iodine no.=ca 28-32 and an nD 25=ca. 1.471. Also suitable for use in this category is, for instance. Nikkol® HCO-60, a reaction product of hydrogenated castor oil and ethylene oxide exhibiting the following characteristics: acid no.=ca. 0.3; saponification no.=ca. 47.4; hydroxy value=ca 42.5. pH (5%)=ca 4.6; Color APHA=ca. 40, m.p.=ca. 36.0° C.; Freezing point=ca. 32.4° C.; H2O content (%, KF)=ca. 0.03.

Poly(ethylene-gly cols) are used in some embodiments as the agent for dispersing and/or dissolving the ophthalmic drug in the ointment base according to the present disclosure. Suitable poly(ethylene-gly col)s are typically mixtures of polymeric compounds of the general formula H—(OCH2—CH2)nOH, wherein the index n typically ranges from 4 to 230 and the mean molecular weight from about 200 to about 10000. Preferably n is a number from about 6 to about 22 and the mean molecular weight between about 300 and about 1000, more preferably n ranges from about 6 to about 13 and the mean molecular weight from about 300 to about 600, most preferably n has a value of about 8.5 to about 9 and the relative molecular weight is about 400. Suitable poly(ethylene-glycols) are readily available commercially, for example poly(ethylene-gly cols) having a mean molecular weight of about 200, 300, 400, 600, 1000, 1500, 2000, 3000, 4000, 6000, 8000 and 10000.

The poly(ethylene-gly cols), in particular the preferred types described in the foregoing paragraph, are preferably used in amounts of 1 to 10, more preferably 1 to 5 percent by weight of the entire semisolid ophthalmic composition.

An especially preferred embodiment of the compositions according to the instant disclosure comprises an agent for dispersing and/or dissolving of the drug in the ointment base which is selected from a poly(ethylene-glycol), a polyethoxylated castor oil and preferably a mixture of said components.

Gel/Ointment Viscosity

In some embodiments, the composition has a Brookfield RVDV viscosity of from about 10,000 to about 300,000 cps at about 20° C. and sheer rate of $1s^{-1}$. In some embodiments, the composition has a Brookfield RVDV viscosity of from about 15,000 to about 200,000 cps at about 20° C. and sheer rate of $1s^{-1}$. In some embodiments, the composition has a Brookfield RVDV viscosity of from about 50,000 to about 150,000 cps at about 20° C. and sheer rate of $1s^{-1}$. In some embodiments, the composition has a Brookfield RVDV viscosity of from about 70,000 to about 130,000 cps at about 20° C. and sheer rate of $1s^{-1}$. In some embodiments, the composition has a Brookfield RVDV viscosity of from about 90,000 to about 110,000 cps at about 20° C. and sheer rate of $1s^{-1}$.

In some embodiments, the ophthalmic gel formulation contains a viscosity enhancing agent sufficient to provide a viscosity of between about 500 and 1,000,000 centipoise, between about 750 and 1,000,000 centipoise; between about 1000 and 1,000,000 centipoise; between about 1000 and 400,000 centipoise; between about 2000 and 100,000 centipoise; between about 3000 and 50,000 centipoise; between about 4000 and 25,000 centipoise; between about 5000 and 20,000 centipoise; or between about 6000 and 15,000 centipoise. In some embodiments, the ophthalmic gel formulation contains a viscosity enhancing agent sufficient to provide a viscosity of between about 50,0000 and 1,000,000 centipoise.

In some embodiments, the compositions described herein are low viscosity compositions at body temperature. In some embodiments, low viscosity compositions contain from about 1% to about 10% of a viscosity enhancing agent (e.g., gelling components such as polyoxyethylene-polyoxypropylene copolymers). In some embodiments, low viscosity compositions contain from about 2% to about 10% of a viscosity enhancing agent (e.g., gelling components such as polyoxyethylene-polyoxypropylene copolymers). In some embodiments, low viscosity compositions contain from about 5% to about 10% of a viscosity enhancing agent (e.g., gelling components such as poly oxyethylene-poly oxypropylene copolymers). In some embodiments, low viscosity compositions are substantially free of a viscosity enhancing agent (e.g., gelling components such as poly oxyethylene-poly oxypropylene copolymers). In some embodiments, a low viscosity ophthalmic agent composition described herein provides an apparent viscosity of from about 100 cP to about 10,000 cP. In some embodiments, a low viscosity ophthalmic agent composition described herein provides an apparent viscosity of from about 500 cP to about 10,000 cP. In some embodiments, a low viscosity ophthalmic agent composition described herein provides an apparent viscosity of from about 1000 cP to about 10,000 cP.

In some embodiments, the compositions described herein are viscous compositions at body temperature. In some embodiments, viscous compositions contain from about 10% to about 25% of a viscosity enhancing agent (e.g., gelling components such as polyoxyethylene-poly oxypropylene copolymers). In some embodiments, the viscous compositions contain from about 14% to about 22% of a viscosity enhancing agent (e.g., gelling components such as polyoxyethylene-polyoxypropylene copolymers). In some embodiments, the viscous compositions contain from about 15% to about 21% of a viscosity enhancing agent (e.g., gelling components such as polyoxyethylene-polyoxypropylene copolymers). In some embodiments, a viscous ophthalmic composition described herein provides an apparent viscosity of from about 100,000 cP to about 1,000,000 cP. In some embodiments, a viscous ophthalmic composition described herein provides an apparent viscosity of from about 150,000 cP to about 500,000 cP. In some embodiments, a viscous ophthalmic composition described herein provides an apparent viscosity of from about 250,000 cP to about 500,000 cP. In some of such embodiments, a viscous ophthalmic composition is a liquid at room temperature and gels at about between room temperature and body temperature (including an individual with a serious fever, e.g., up to about 42° C.). In some embodiments, a viscous ophthalmic composition is administered as monotherapy for treatment of an ophthalmic disease or condition described herein.

In some embodiments, the viscosity of the gel formulations presented herein is measured by any means described. For example, in some embodiments, an LVDV-II+CP Cone Plate Viscometer and a Cone Spindle CPE-40 is used to calculate the viscosity of the gel formulation described herein. In other embodiments, a Brookfield (spindle and cup) viscometer is used to calculate the viscosity of the gel formulation described herein. In some embodiments, the viscosity ranges referred to herein are measured at room temperature. In other embodiments, the viscosity ranges referred to herein are measured at body temperature (e.g., at the average body temperature of a healthy human).

Gel/Ointment Dose-To-Dose Uniformity

Typical ophthalmic gels are packaged in eye drop bottles and administered as drops. For example, a single administration (i.e. a single dose) of an ophthalmic gel includes a single drop, two drops, three drops or more into the eyes of the patient. Furthermore, typical ophthalmic ointments are packaged in tubes or other squeezable containers with a dispensing nozzle through which strips of the ointment are delivered. For example, a single administration (i.e. a single dose) of an ophthalmic ointment includes a single strip, or multiple strips into the eyes of the patient. In some embodiments, one dose of the ophthalmic gel described herein is one drop of the gel composition from the eye drop bottle. In some embodiments, one dose of the ophthalmic ointment is one strip of the ointment composition dispensed through the nozzle of a dispersing tube.

In some cases, described herein include ophthalmic gel compositions which provide a dose-to-dose uniform concentrations. In some instances, the dose-to-dose uniform concentration does not present significant variations of drug content from one dose to another. In some instances, the dose-to-dose uniform concentration does provide consistent drug content from one dose to another.

In some cases, described herein include ophthalmic ointment compositions which provide a dose-to-dose uniform concentrations. In some instances, the dose-to-dose uniform concentration does not present significant variations of drug content from one dose to another. In some instances, the dose-to-dose uniform concentration does provide consistent drug content from one dose to another.

In some embodiments, the composition has a dose-to-dose ophthalmic agent concentration variation of less than 50%. In some embodiments, the composition has a dose-to-dose ophthalmic agent concentration variation of less than 40%. In some embodiments, the composition has a dose-to-dose ophthalmic agent concentration variation of less than 30%. In some embodiments, the composition has a dose-to-dose ophthalmic agent concentration variation of less than 20%. In some embodiments, the composition has a dose-to-dose ophthalmic agent concentration variation of less than 10%. In some embodiments, the composition has a dose-to-dose ophthalmic agent concentration variation of less than 5%.

In some embodiments, the dose-to-dose ophthalmic agent concentration variation is based on 10 consecutive doses. In some embodiments, the dose-to-dose ophthalmic agent concentration variation is based on 8 consecutive doses. In some embodiments, the dose-to-dose ophthalmic agent concentration variation is based on 5 consecutive doses. In some embodiments, the dose-to-dose ophthalmic agent concentration variation is based on 3 consecutive doses. In some embodiments, the dose-to-dose ophthalmic agent concentration variation is based on 2 consecutive doses.

A nonsettling formulation should not require shaking to disperse drug uniformly. A "no-shake" formulation is potentially advantageous over formulations that require shaking for the simple reason that patients' shaking behavior is a major source of variability in the amount of drug dosed. It has been reported that patients often times do not or forget to shake their ophthalmic compositions that requires shaking before administering a dose, despite the instructions to shake that were clearly marked on the label. On the other hand, even for those patients who do shake the product, it is normally not possible to determine whether the shaking is adequate in intensity and/or duration to render the product uniform. In some embodiments, the ophthalmic gel compositions and ophthalmic ointment compositions described herein are "no-shake" formulations that maintained the dose-to-dose uniformity described herein.

To evaluate the dose-to-dose uniformity, drop bottles or tubes containing the ophthalmic aqueous compositions, the ophthalmic gel compositions, or ophthalmic ointment compositions are stored upright for a minimum of 12 hours prior to the start of the test. To simulate the recommended dosing of these products, predetermined number of drops or strips are dispensed from each commercial bottles or tubes at predetermined time intervals for an extended period of time or until no product is left in the bottle or tube. All drops and strips are dispensed into tared glass vials, capped, and stored at room temperature until analysis. Concentrations of an ophthalmic agent in the expressed drops are determined using a reverse-phase HPLC method.

Methods of Treatment

Disclosed herein are methods of treating one or more ophthalmic conditions or diseases by administering to an eye of an individual in need thereof an effective amount of an ophthalmic composition described supra. Also disclosed herein are methods of ameliorating or reducing one or more ophthalmic conditions or diseases by administering to an eye of an individual in need thereof an effective amount of an ophthalmic composition described supra.

In some embodiments, the ophthalmic condition or disease includes a condition or disease associated with the eyelid, the lacrimal system, or the orbit (FIG. 1). In some embodiments, the lacrimal system encompasses the orbital structures for tear production and drainage. In some embodiments, the lacrimal system comprises the lacrimal gland responsible for tear production, excretory ducts which convey the fluid to the surface of the eye, lacrimal canaliculi, lacrimal sac, and nasolacrimal duct. In some embodiments, the orbit encompasses the eye and its associated appendages. In some embodiments, an ophthalmic composition described herein is administered to an eye of an individual in need thereof for a condition or disease associated with the eyelid, lacrimal system or the orbit.

In some embodiments, the ophthalmic condition or disease includes a condition or disease associated with the conjunctiva, sclera, cornea, iris, or ciliary body (FIG. 1). Conjunctiva lines the inside of the eyelids and covers the sclera. Sclera, or the white of the eye, is an opaque, fibrous, protective outer layer of the eye. Cornea is the transparent front part of the eye that covers the iris, pupil, and anterior chamber. Iris is a thin, circular structure in the eye responsible for controlling the diameter and size of the pupil and therefore the amount of light reaching the retina. Ciliary body includes the ciliary muscle, which controls the shape of the lens and the ciliary epithelium, which produces the aqueous humor. In some embodiments, an ophthalmic composition described herein is administered to an eye of an individual in need thereof for a condition or disease associated with conjunctiva, sclera, cornea, iris, or ciliary body.

In some embodiments, the ophthalmic condition or disease includes a condition or disease associated with the choroid or retina (FIG. 1). Choroid, also known as choroidea or choroid coat, is the vascular layer of the eye containing connective tissue and is in between the retina and the sclera. Retina is the third and inner coat of the eye and is a light-sensitive tissue layer. In some embodiments, an ophthalmic composition described herein is administered to an eye of an individual in need thereof for a condition or disease associated with choroid or retina.

In some embodiments, the ophthalmic condition or disease includes a condition or disease associated with the lens (FIG. 1). The lens or crystalline lens is a transparent, biconvex structure in the eye that in combination with the cornea helps to refract light to be focused on the retina. In some embodiments, an ophthalmic composition described herein is administered to an eye of an individual in need thereof for a condition or disease associated with the lens.

In some embodiments, the ophthalmic conditions or diseases include, but are not limited to, Acanthamoeba keratitis, Bell's palsy, blepharochalasis, blepharitis, chalazion, cataract, cyclitis, cytomegalovirus (CMV) retinitis, chorioretinal inflammation, conjunctivitis (e.g., allergy related conjunctivitis or conjunctivitis due to infection), neonatal conjunctivitis, corneal neovascularization, corneal ulcer, dermatitis, diabetic retinopathy, dry eye syndrome, dacryoadenitis, dacryostenosis, endophthalmitis, epiphora, episcleritis, eye impetigo, eyelash hypotrichosis, Fuchs' dystrophy (also known as Fuchs' corneal endothelial dystrophy or FCED), glaucoma, hypermetropia, iritis, keratoconjunctivitis, keratoconjunctivitis sicca, macular degeneration (e.g., Stargardt's disease), macular dystrophy, macular edema (e.g., diabetic macular edema), myopia, ocular hypertension, loiasis, ocular rosacea, onchocerciasis (or known as river blindness or Robles disease), optic neuritis and optic neuropathy, keratitis (e.g., bacterial keratitis, fungal keratitis, parasitic keratitis, or viral keratitis), pinguecular and pterygium, production of miosis, scleritis, steroid responsive inflammatory conditions, stye (or hordeolum), temporal arteritis, Thygeson's superficial punctate keratopathy (TSPK), trachoma, organophosphate poisoning, basal cell carcinoma, squamous carcinoma, sebaceous carcinoma, malignant melanoma, orbital lymphoma, uveitis, uveal melanoma, retinoblastoma, medulloepithelioma, or primary intraocular lymphoma. In some embodiments, viral keratitis includes ocular herpes or Herpetic keratitis, or Herpes Simplex dendritic keratitis.

In some embodiments, viruses that cause viral eye infections include Herpes simple virus, Epstein Barr virus, or influenza virus.

In some embodiments, fungi that cause fungal eye infections include *Arthrobotrys oligospora, Aspergillus* versicolar, *Candida, Cladosporium, Cephaliophora irregularis, Exophiala, Fusarium* (e.g., *Fusarium solani*), *Phoma,* or *Scedosporium* (e.g., *Scedosporium prolificans*).

In some embodiments, bacteria that cause bacterial eye infections include *Chlamydia trachomatis, N. meningitidis, Staphylococcus aureus, S. epidermidis, S. pneumoniae, Streptococcus* spp., or *Pseudomonas aeruginosa.*

In some embodiments, parasites that cause eye infections include Demodex, Leishmania, nematode such as *Loa loa, Simulium, Toxoplasma gondii,* or *Toxocara.*

In some embodiments, the ophthalmic condition or disease refers to a condition or disease that requires surgery. In some embodiments, one or more of the ophthalmic compositions is administered before, during, or after surgery, or for surgery-related complications. Exemplary surgeries include laser eye surgery, cataract surgery, glaucoma surgery, canaloplasty, refractive surgery, corneal surgery, vitrectomy, eye muscle surgery, and oculoplastic surgery. In some embodiments, surgery-related complications include postoperative increased intraocular pressure and postoperative ocular inflammation.

In some embodiments, the ophthalmic condition or disease refers to a condition or disease that requires aid of a diagnostic agent for visualization. In some embodiments, one or more of the ophthalmic compositions is administered as a diagnostic agent for visualization.

In some embodiments, an ophthalmic composition is administered as part of a normal or routine eye examination procedure. In some embodiments, the normal or routine eye examination procedure is an eye exam. In some embodiments, an ophthalmic composition comprising a mydriatic agent is administered for dilation of the pupil during an eye exam.

In some embodiments, the ophthalmic aqueous formulations described herein are packaged in eye drop bottles and administered as drops. For example, a single administration (i.e. a single dose) of an ophthalmic aqueous formulation includes a single drop, two drops, three drops or more into the eyes of the patient. In some embodiments, the ophthalmic gel formulations described herein are packaged in eye drop bottles and administered as drops. For example, a single administration (i.e. a single dose) of an ophthalmic gel includes a single drop, two drops, three drops or more into the eyes of the patient. In some embodiments, the ophthalmic ointment formulations described herein are packaged in tubes or other squeezable containers with a dispensing nozzle through which strips of the ointment are delivered. For example, a single administration (i.e. a single dose) of an ophthalmic ointment includes a single strip, or multiple strips into the eyes of the patient. In some embodiments, one dose of the ophthalmic aqueous formulation described herein is one drop of the aqueous composition from the eye drop bottle. In some embodiments, one dose of the ophthalmic gel described herein is one drop of the gel composition from the eye drop bottle. In some embodiments, one dose of the ophthalmic ointment is one strip of the ointment composition dispensed through the nozzle of a dispersing tube.

In some embodiments of the disclosed method, the ophthalmic composition is stored below room temperature prior to first use. In some embodiments of the disclosed method, the ophthalmic composition is stored at between about 2° C. to about 10° C. prior to first use. In some embodiments of the disclosed method, the ophthalmic composition is stored at about 2° C., about 3° C. about 4° C., about 5° C., about 6° C., about 7° C. about 8° C., about 9° C., or about 10° C. prior to first use. In some embodiments of the disclosed method, the ophthalmic composition is stored at between about 4° C. to about 8° C. prior to first use.

In some embodiments of the disclosed method, the ophthalmic composition is stored at room temperature after first use. In some embodiments of the disclosed method, the ophthalmic composition is stored at between about 16° C. to about 26° C. after to first use. In some embodiments of the disclosed method, the ophthalmic composition is stored at about 16° C., about 17° C., about 18° C., about 19° C., about 20° C., about 21° C., about 22° C., about 23° C. about 24° C. about 25° C., or about 26° C. after to first use.

In some embodiments, the ophthalmic aqueous formulations are administered as follows: the lower lid of the eye to be administered was pulled down and a predetermined amount of the aqueous formulation (e.g. 1-3 drops) is applied to the inside of the eyelid. The ophthalmic tip of the dispensing mechanism does not touch any surface to avoid contamination and/or injury.

In some embodiments, the ophthalmic gel formulations are administered as follows: the lower lid of the eye to be administered was pulled down and a predetermined amount of gel (e.g. 1-3 drops) is applied to the inside of the eyelid. The ophthalmic tip of the dispensing mechanism does not touch any surface to avoid contamination and/or injury.

In some embodiments, the ophthalmic ointment formulations are administered as follows: the lower lid of the eye to be administered was pulled down and a small amount of ointment (approximately 0.25 inches) was applied to the inside of the eyelid. The ophthalmic tip of the dispensing mechanism does not touch any surface to avoid contamination and/or injury.

In some embodiments, the ophthalmic composition is administered at predetermined time intervals over an extended period of time. In some embodiments, the ophthalmic composition is administered once a day. In some embodiments, the ophthalmic composition is administered once every day. In some embodiments, the ophthalmic composition is administered every other day. In some embodiments, the ophthalmic composition is administered over 1 week, 2 weeks, 1 month, 2 months, 3 months, 6 months, 1 year, 2 years, 3 years, 4 years, 5 years, 6 years, 7 years, 8 years, 9 years, 10 years, 11 years, or 12-15 years. In some embodiments, the ophthalmic composition is administered only once.

In some embodiments, the ophthalmic composition is administered in doses having a dose-to-dose ophthalmic agent concentration variation of less than 50%, less than 40%, less than 30%, less than 20%, less than 10%, or less than 5%.

The number of times a composition is administered to an individual in need thereof depends on the discretion of a medical professional, the disorder, the severity of the disorder, and the individual's response to the formulation. In some embodiments, a composition disclosed herein is administered once to an individual in need thereof with a mild acute condition. In some embodiments, a composition disclosed herein is administered more than once to an individual in need thereof with a moderate or severe acute condition. In the case wherein the patient's condition does not improve, upon the doctor's discretion the administration of an ophthalmic agent is administered chronically, that is, for an extended period of time, including throughout the duration of the patient's life in order to ameliorate or otherwise control or limit the symptoms of the patient's disease or condition.

In the case wherein the patient's condition does not improve, upon the doctor's discretion the administration of the ophthalmic agent is administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the ophthalmic agent is given continuously; alternatively, the dose of drug being administered is temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday is from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's ophthalmic conditions has occurred, a maintenance ophthalmic agent dose is administered if necessary. Subsequently, the dosage or the frequency of administration, or both, is optionally reduced, as a function of the symptoms, to a level at which the improved disease, disorder or condition is retained. In certain embodiments, patients require intermittent treatment on a long-term basis upon any recurrence of symptoms.

The amount of ophthalmic agent that will correspond to such an amount will vary depending upon factors such as the particular compound, disease condition and its severity, according to the particular circumstances surrounding the case, including, e.g., the specific ophthalmic agent being administered, the route of administration, the condition being treated, the target area being treated, and the subject or host being treated. The desired dose is presented in a single dose or as divided doses administered simultaneously (or over a short period of time) or at appropriate intervals.

In some embodiments, the initial administration is a particular ophthalmic agent and the subsequent administration a different formulation or ophthalmic agent.

Kits/Articles of Manufacture

The disclosure also provides kits for treating one or more ophthalmic conditions or diseases described herein. Such kits generally will comprise one or more of the ophthalmic compositions disclosed herein, and instructions for using the kit. The disclosure also contemplates the use of one or more of the ophthalmic compositions, in the manufacture of medicaments for abating, reducing, or ameliorating the symptoms of one or more of the ophthalmic conditions or diseases described herein.

In some embodiments, kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. In other embodiments, the containers are formed from a variety of materials such as glass or plastic.

The articles of manufacture provided herein contain packaging materials. Packaging materials for use in packaging pharmaceutical products are also presented herein. See, e.g., U.S. Pat. Nos. 5,323,907, 5,052, 558 and 5,033, 252. Examples of pharmaceutical packaging materials include, but are not limited to, drop bottles, tubes, pumps, bags, vials, containers, syringes, bottles, and any packaging material suitable for a selected formulation and intended mode of administration and treatment. A wide array of ophthalmic compositions provided herein are contemplated as are a variety of treatments for any disease, disorder, or condition that benefits by controlled release administration of an ophthalmic agent to the eye.

In some embodiments, a kit includes one or more additional containers, each with one or more of various materials (such as rinses, wipes, and/or devices) desirable from a commercial and user standpoint for use of a formulation described herein. Such materials also include labels listing contents and/or instructions for use and package inserts with instructions for use. A set of instructions is optionally included. In a further embodiment, a label is on or associated with the container. In yet a further embodiment, a label is on a container when letters, numbers or other characters forming the label are attached, molded or etched into the container itself; a label is associated with a container when it is present within a receptacle or carrier that also holds the container, e.g., as a package insert. In other embodiments a label is used to indicate that the contents are to be used for a specific therapeutic application. In yet another embodiment, a label also indicates directions for use of the contents, such as in the methods described herein.

In certain embodiments, the ophthalmic compositions are presented in a dispenser device which contains one or more unit dosage forms containing a compound provided herein. In a further embodiment, the dispenser device is accompanied by instructions for administration. In yet a further embodiment, the dispenser is also accompanied with a notice associated with the container in form prescribed by a governmental agency regulating the manufacture, use, or sale of pharmaceuticals, which notice is reflective of approval by the agency of the form of the drug for human or veterinary administration. In another embodiment, such notice, for example, is the labeling approved by the U.S. Food and Drug Administration for prescription drugs, or the approved product insert. In yet another embodiment, compositions containing a compound provided herein formulated in a compatible pharmaceutical carrier are also prepared, placed in an appropriate container, and labeled for treatment of an indicated condition.

Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include," "includes," and "included." is not limiting.

As used herein, ranges and amounts is expressed as "about" a particular value or range. About also includes the exact amount. Hence "about 5 μg" means "about 5 μg" and also "5 μg." Generally, the term "about" includes an amount that is expected to be within experimental error.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

The terms "subject" and "individual", as included herein, are used interchangeably. None of the terms are to be interpreted as requiring the supervision of a medical professional (e.g., a doctor, nurse, physician's assistant, orderly, hospice worker).

Examples

Example 1—Ophthalmic Formulations

Exemplary compositions for preparation of ophthalmic formulations are described in Tables 1-5.

TABLE 1

Aqueous Solution Formulation

| Ingredient | Quantity (mg/g) | Concentration (wt %) |
|---|---|---|
| Ophthalmic agent | 0.01-200 | 0.001-20 (wt %) |
| Buffer agent and/or pD adjusting agent (e.g., borates and/or DCl) | — | q.s. for pD = 4-8 |
| Preservative (e.g. benzalkonium chloride, cetrimonium sodium perborate, etc.) | — | q.s. to prevent the growth of or to destroy microorganism introduced into the solution |
| Tonicity and/or Osmolarity adjustor (e.g. NaCl, mannitol, etc) | — | q.s. to 0.5-2.0 wt % |
| Deuterated Water | — | q.s. to 100 wt % |

TABLE 2

Aqueous Solution Formulation

| Ingredient | Quantity (mg/g) | Concentration (wt %) |
|---|---|---|
| Ophthalmic agent | 0.01-50 | 0.001-5 (wt %) |
| Buffer agent and/or pD adjusting agent (e.g., borates and/or DCl) | — | q.s. for pD = 4-8 |
| Preservative (e.g. benzalkonium chloride, cetrimonium sodium perborate, etc.) | — | q.s. to prevent the growth of or to destroy microorganism introduced into the solution |
| Tonicity and/or Osmolarity adjustor (e.g. NaCl, mannitol, etc) | — | q.s. to 0.5-2.0 wt % |
| Deuterated Water | — | q.s. to 100 wt % |

TABLE 3

Cellulose Gel Formulation

| Ingredient | Quantity (mg/g) | Concentration (wt %) |
|---|---|---|
| Ophthalmic agent | 0.01-200 | 0.001-20 (wt %) |
| Viscosity enhancing agent (e.g. hydroxypropyl methylcellulose) | 10-50 | 1-5 (wt %) |
| Buffer agent and/or pD adjusting agent (e.g., sodium acetate and/or DCl) | — | q.s. for pD = 4-8 |
| Stabilizer (e.g. EDTA, cyclodextrin, etc.) | — | q.s. for low degradation of ophthalmic agent |
| Osmolarity modifier (e.g. NaCl) | — | q.s. 150-500 mOsm/L |
| Deuterated Water | — | q.s. to 100 wt % |

TABLE 4

Thermosetting Gel Formulation

| Ingredient | Quantity (mg/g) | Concentration (wt %) |
|---|---|---|
| Ophthalmic agent | 0.01-200 | 0.001-20 (wt %) |
| Viscosity enhancing agent (e.g. poloxamer 407) | 100-250 | 10-25 (wt %) |
| Buffer agent and/or pD adjusting agent (e.g., sodium acetate and/or DCl) | — | q.s. for pH = 4.2-7.9 |
| Stabilizer (e.g. EDTA, cyclodextrin, etc.) | — | q.s. for low degradation of ophthalmic agent |
| Osmolarity modifier (e.g. NaCl) | — | q.s. 150-500 mOsm/L |
| Deuterated Water | — | q.s. to 100 wt % |

TABLE 5

Ointment Formulation

| Ingredient | Quantity (g) for 1000 mL solution | Concentration in 1000 mL aqueous solution |
|---|---|---|
| Ophthalmic agent | 0.01-200 | 0.001-20 (wt %) |
| Dispersing agent (e.g. polyethyleneglycol, and/or polyethoxylated castor oil and/or C12-C20 alcohol | 10-200 | 1-20 (wt %) |
| Buffering agent pD adjusting agent (e.g. DCl) | — | q.s. for pD = 4-8 |
| Stabilizer (e.g. EDTA, cyclodextrin, etc.) | — | q.s. for low degradation of ophthalmic agent |
| Osmolarity modifier (e.g. NaCl) | — | q.s. 150-500 mOsm/L |
| Ointment base (e.g. wool wax and/or petrolatum and/or liquid paraffin) | — | q.s. to 100 wt % |

Example 2—Preparation of an Aqueous Solution Formulation Containing 0.01% an Ophthalmic Agent in $D_2O$ Stock 1% Solution In a 100 mL solution, 1 gram of an ophthalmic agent, and 0.77 g of NaCl (and other ingredients/components preferably in their dry state) are added along with a quantity sufficient to equal 100 mL sterile deuterated water for injection. The solution is mixed in an appropriately sized beaker with a stir bar on a hot plate until all of the solid powders have dissolved and the solution has become clear with no visible particles. Next, the stir bar is removed, and the solution is poured into a filter bottle and vacuum filtered through a 0.22 micron pothyethersulfone membrane filter into a sterile bottle. The filter top is removed from the sterile stock bottle and the stock bottle is capped for storage with a sterile bottle cap.

Diluted 0.01% Solution 0.3 mL of the 1% solution is combined with a quantity sufficient to achieve 30 mL total of sterile 0.9% Sodium Chloride For Injection USP. The solution is thoroughly mixed. The pD of the solution is recorded. A 0.22 micron filter is placed on the tip of the syringe and the solution is aliquoted into separate sterile containers.

Example 3—Stability Analysis

Five 0.01% ophthalmic solutions are prepared from the 1% ophthalmic stock solution (preparation as described in Example 2). The pD of the five solutions are 4.5, 5, 5.5, 6, and 6.5 for solutions 1-5, respectively. Each solution is thoroughly mixed. A 0.22 micron filter is placed on the tip of the syringe and the solution is aliquoted into separate sterile containers according to Table 6.

TABLE 6

Container Filling Outline

| Type of Container | Volume of 0.01% Ophthalmic Drug Product in Container | Total Containers Filled |
|---|---|---|
| Sterile Eyedroppers | 5-mL | 12 |
| Sterile Glass Vials | 5-mL | 12 |

The samples are then stored at different conditions for stability analysis. The samples are analyzed at different time points up to 2 months. The storage conditions include, 4WC with 75% relative humidity (RH)(samples were transferred from 2-8° C. condition after 3 days), 25° C. with 60% RH, and 60° C. The time points are 1 week, 2 weeks, 1 month, and 2 months. At each of the time point, one plastic eyedropper (LDPE plastic) and one glass vial from each of the stored condition are removed and allowed to equilibrate to ambient conditions. Once equilibrated, both the plastic eyedropper and the glass vials are inverted 3 times. The solution in the eyedroppers is transferred to an HPLC vial in a drop wise fashion through the dropper. The solution in the glass vial is aliquoted into an HPLC vial using a glass Pasteur pipette. The samples are then tested for purity and potency using the UPLC method listed in Table 7.

TABLE 7

UPLC Method Parameters

| Parameter | Condition |
|---|---|
| Column | EMD, Hiber HR PuropherSTAR C-18, 100 × 2.1 mm, 2 μm |
| Mobile Phase/Diluent | 87:13, 50 mM Potassium Phosphate: Acetonitrile, pH 3.5 |
| Flow | Isocratic |
| Flow Rate | 0.5 mL/min |
| Detection Wavelength | 210 nm |
| Column Temperature | 30 ± 3° C. |
| Autosampler Temperature | 5 ± 3° C. |
| Run Time | 6.0 minutes |
| Injection Volume | 10 μL |
| Needle Wash Solution | 90/10 Water: Acetonitrile |

Arrhenius based shelf life predictions are calculated. These predictions are based on an assumption that the degradation is first order (linear).

Example 4—Dose Uniformity (10-Dose

To evaluate the dose-to-dose uniformity, drop bottles containing the ophthalmic aqueous composition are stored upright for a predetermined period of time (e.g. 12 hours) prior to the start of the test. To simulate the recommended dosing of the product, 10 drops of the aqueous composition are dispensed from each bottle at predetermined time intervals (e.g. consecutively, every 1 minute, every 10 minutes, every hour or every 24 hours). All drops are dispensed into tared glass vials, capped, and stored at room temperature until analysis. Concentrations of an ophthalmic agent in the expressed drops are determined using a reverse-phase HPLC method.

Example 5—Dose Uniformity (5-Dose

To evaluate the dose-to-dose uniformity, drop bottles containing the ophthalmic aqueous composition are stored upright for a predetermined period of time (e.g. 12 hours) prior to the start of the test. To simulate the recommended dosing of the product, 5 drops of the aqueous composition are dispensed from each bottle at predetermined time intervals (e.g. consecutively, every 1 minute, every 10 minutes, every hour or every 24 hours). All drops are dispensed into tared glass vials, capped, and stored at room temperature until analysis. Concentrations of an ophthalmic agent in the expressed drops are determined using a reverse-phase HPLC method.

Example 6—Dose Uniformity (2-Dose

To evaluate the dose-to-dose uniformity, drop bottles containing the ophthalmic aqueous composition are stored upright for a predetermined period of time (e.g. 12 hours) prior to the start of the test. To simulate the recommended dosing of the product, 2 drops of the aqueous composition are dispensed from each bottle at predetermined time intervals (e.g. consecutively, every 1 minute, every 10 minutes, every hour or every 24 hours). All drops are dispensed into tared glass vials, capped, and stored at room temperature until analysis. Concentrations of an ophthalmic agent in the expressed drops are determined using a reverse-phase HPLC method.

Example 7—Effect of D on Ophthalmic Acceptance in Guinea Pigs

A cohort of guinea pigs is administered 50 µL of ophthalmic formulations having different pD values described herein. For example, ophthalmic formulations comprising $H_2O$ or deuterated water (e.g., $D_2O$) are administered to the animals. Animal behavior is recorded at predetermined time intervals to evaluate the acceptance of the ophthalmic formulations Example 8—In vivo Rabbit Eye Irritation Test The exemplary compositions disclosed herein are subjected to rabbit eye irritation test to evaluate their safety profile. The test composition are tested for eye irritation test in New Zealand Rabbits (see for example Abraham M H, et al, Draize rabbit eye test compatibility with eye irritation thresholds in humans: a quantitative structure-activity relationship analysis. Toxicol Sci. 2003 December; 76(2):384-91. Epub 2003 Sep. 26, see also Gettings S D et al., A comparison of low volume. Draize and in vitro eye irritation test data. III. Surfactant-based formulations. Food Chem Toxicol, 1998 March; 36(3):209-31). The study involves single ocular administration into the right eye and the same volume of its placebo in the left eye of each of the three rabbits. Rabbits are examined immediately and after instillation of the compositions for 4, 24, 48 and 72 hours post instillation to note the signs/symptoms of eye irritation, if any. The test compositions show no sign of irritancy in cornea, iris and conjunctivae of the rabbit eyes.

Example 9—Safety and Efficacy Studies of Ophthalmic Aqueous Formulation

A clinical trial is performed to investigate the efficacy and safety of ophthalmic aqueous formulations described herein in patents. In some cases, the study is open-label, single blind, or double blind study. Patient selection criteria includes an ophthalmic condition of interest, and additional factors such as age, sex, and/or health conditions.

The patients are randomized to receive 5%, 1%, or 0.1% of an ophthalmic aqueous formulation formulated in deuterated water (e.g., $D_2O$) once nightly in one or both eyes. Allocation ratio is defined based on the patient population.

The patients are evaluated on day 0 (baseline), day 14, day 30, and then at 2, 3, 4, 5, 6, 8, 10, 12, 18, 20, 24, and 36 months.

The primary outcome is condition or disease progression over the time period of the study. Safety is assessed by adverse events including allergic reactions, irritation, or development of blurring of vision in one or both eyes.

Example 10—Preparation of an Ointment Formulation

An ophthalmic agent is mixed with the dispersing agent (e.g. polyethyleneglycol) under heating and sonication and this mixture is further thoroughly mixed with a molten ointment base (e.g. a mixture of wool wax, white petrolatum, and liquid paraffin). The mixture is placed in a pressure vessel, and sterilized at 125 T for 30-45 minutes and cooled to room temperature. In another embodiment, autoclaving is conducted under nitrogen. The resulting ophthalmic ointment is aseptically filled into pre-sterilized containers (e.g. tubes).

While preferred embodiments of the present disclosure have been shown and described herein, such embodiments are provided by way of example only. Various alternatives to the embodiments described herein are optionally employed in practicing the disclosure. It is intended that the following claims define the scope of the disclosure and that methods and structures within the scope of these claims and their equivalents be covered thereby.

What is claimed is:

1. A method of treating an ophthalmic condition or disease comprising administering an ophthalmic composition to a subject in need thereof, the ophthalmic composition comprising:
   (i) about 0.015 wt % to about 1 wt % pilocarpine or a pharmaceutically acceptable salt of pilocarpine, and
   ii deuterated water, wherein the ophthalmic composition comprises at least 95% deuterated water;
   wherein the composition comprises a pD of about 4 to about 8; wherein the composition comprises at least about 80% pilocarpine based on initial concentration after at least about one week under storage conditions.

2. The method of claim 1, wherein the ophthalmic composition comprises at least one of: about 85%, about 90%, about 95%, about 97%, about 98%, or about 99% of the pilocarpine or the pharmaceutically acceptable salt of pilocarpine based on an initial concentration after an extended period of time under a storage condition, wherein the extended period of time is one of: about 1 week, about 2 weeks, about 3 weeks, about 1 month, about 2 months, about 3 months, about 4 months, about 5 months, about 6 months, about 8 months, about 10 months, about 12 months, about 18 months, about 24 months, about 36 months, about 4 years, or about 5 years.

3. The method of claim 2, wherein the storage condition has a storage temperature of about 16° C. to about 30° C. or about 20° C. to about 25° C.

4. The method of claim 1, wherein the ophthalmic composition comprises about 0.015 wt % to about 0.1 wt % of pilocarpine or a pharmaceutically acceptable salt of pilocarpine.

5. The method of claim 1, wherein the ophthalmic composition further comprises ethylenediaminetetraacetic acid (EDTA).

6. The method of claim 1, wherein the ophthalmic composition further comprises an osmolarity adjusting agent, a preservative, a buffering agent, a tonicity adjusting agent, a pD adjusting agent, a viscosity-enhancing agent, or a combination thereof.

7. The method of claim 6, wherein the osmolarity adjusting agent is sodium chloride.

8. The method of claim 6, wherein the preservative is selected from benzalkonium chloride, cetrimonium, sodium perborate, stabilized oxychloro complex, polyquaternium-1, chlorobutanol, edetate disodium, polyhexamethylene biguanide, or combinations thereof.

9. The method of claim 6, wherein the buffering agent is selected from borates, borate-polyol complexes, phosphate buffering agents, citrate buffering agents, acetate buffering agents, carbonate buffering agents, organic buffering agents, amino acid buffering agents, or combinations thereof.

10. The method of claim 1, wherein the ophthalmic composition has a pD of one of: about 4.5 to about 7.5, about 5 to about 7.0, or about 6 to about 7.0.

11. The method of claim 1, wherein the ophthalmic composition is stored below room temperature prior to first use or is stored at between about 2° C. to about 10° C. prior to first use.

12. The method of claim 1, wherein the ophthalmic composition is stored below room temperature after first use, is stored at between about 2° C. to about 10° C. after first use, or is stored at between about 16° C. to about 26° C. after first use.

13. The method of claim 1, wherein the ophthalmic composition comprises less than 5% $H_2O$.

14. A method of treating an ophthalmic condition or disease comprising administering an ophthalmic composition to a subject in need thereof, the ophthalmic composition comprising:
(i) about 0.015 wt. % to about 1 wt. % pilocarpine or a pharmaceutically acceptable salt of pilocarpine, tropicamide or a pharmaceutically acceptable salt of tropicamide, and
(ii) deuterated water, wherein the ophthalmic composition comprises at least 95% deuterated water;
wherein the composition comprises a pD of about 4 to about 8; wherein the composition comprises at least about 80% pilocarpine based on initial concentration after at least about one week under storage conditions.

15. The method of claim 14, wherein the tropicamide or the pharmaceutically acceptable salt of tropicamide is present in the ophthalmic composition at a concentration about 0.001 wt % to about 20 wt %, about 0.010 wt % to about 0.1 wt %, or about 0.025 wt % to about 0.1 wt % of the total weight of the ophthalmic composition.

16. The method of claim 14, wherein the tropicamide or the pharmaceutically acceptable salt of tropicamide is present in the ophthalmic composition at a concentration of at least about 0.02 wt %, 0.5 wt %, or 1.0 wt % of the total weight of the ophthalmic composition.

17. The method of claim 14, wherein the ophthalmic composition further comprises an osmolarity adjusting agent, a preservative, a buffering agent, a tonicity adjusting agent, a pD adjusting agent, a viscosity-enhancing agent, or a combination thereof.

18. The method of claim 14, wherein the ophthalmic composition is stored below room temperature prior to first use or is stored at between about 2° C. to about 10° C. prior to first use.

19. The method of claim 14, wherein the ophthalmic composition is stored below room temperature after first use, is stored at between about 2° C. to about 10° C. after first use, or is stored at between about 16° C. to about 26° C. after first use.

20. The method of claim 1, wherein the ophthalmic composition further comprises a preservative, a buffering agent, and an osmolarity adjusting agent.

* * * * *

UNITED STATES PATENT AND TRADEMARK OFFICE
CERTIFICATE OF CORRECTION

| | | |
|---|---|---|
| PATENT NO. | : 12,168,017 B2 | Page 1 of 1 |
| APPLICATION NO. | : 17/335490 | |
| DATED | : December 17, 2024 | |
| INVENTOR(S) | : Gregory I. Ostrow et al. | |

It is certified that error appears in the above-identified patent and that said Letters Patent is hereby corrected as shown below:

On the Title Page

Item (71) delete "Applicant: Sydnexis, Inc., Del Mar, CO (US)" and insert --Applicant: Sydnexis, Inc., Del Mar, CA (US)--

In the Claims

In Column 74, Line 33: Claim 1, please replace "ii" with --(ii)--

Signed and Sealed this
Twenty-ninth Day of July, 2025

Coke Morgan Stewart
*Acting Director of the United States Patent and Trademark Office*